United States Patent [19]

Kiyokawa et al.

[11] Patent Number: 5,420,128

[45] Date of Patent: May 30, 1995

[54] PYRIMIDINE DERIVATIVES, METHOD OF MANUFACTURING THE SAME, AND ANDROGEN INHIBITOR

[75] Inventors: Hiroshi Kiyokawa, Nara; Satoshi Yamada; Keisuke Miyajima, both of Otsu; Kinji Hashimoto, Naruto; Masatoshi Inai, Itano; Makoto Inoue, Naruto; Kunihiko Tatsumi, Otsu; Takeshi Yamauchi, Kyoto; Kazunobu Kurisu; Yoshifumi Chone, both of Naruto, all of Japan

[73] Assignee: Otsuka Pharmaceutical Co., Ltd., Tokyo, Japan

[21] Appl. No.: 854,619

[22] PCT Filed: Oct. 7, 1991

[86] PCT No.: PCT/JP91/01367

§ 371 Date: Jun. 9, 1992

§ 102(e) Date: Jun. 9, 1992

[87] PCT Pub. No.: WO92/06096

PCT Pub. Date: Apr. 16, 1992

[30] Foreign Application Priority Data

Oct. 9, 1990 [JP] Japan .................. 2-270970
Oct. 19, 1990 [JP] Japan .................. 2-282745
Aug. 29, 1991 [JP] Japan .................. 3-218927

[51] Int. Cl.⁶ .............. A61K 31/53; A61K 31/505; C07D 487/04; C07D 231/38
[52] U.S. Cl. .................... 514/246; 514/258; 514/267; 544/250; 544/281; 544/220
[58] Field of Search ............ 544/250, 281, 220; 514/246, 267, 258

[56] References Cited

U.S. PATENT DOCUMENTS

| | | | |
|---|---|---|---|
| 3,865,824 | 2/1975 | Kobe et al. | 260/248 |
| 3,910,907 | 10/1975 | O'Brien et al. | 260/310 |
| 3,995,039 | 11/1976 | Rooney et al. | 260/249.5 |
| 4,021,556 | 5/1977 | Springer | 424/251 |
| 4,824,834 | 4/1989 | Fujii et al. | 544/113 |
| 4,997,940 | 3/1991 | Vinogradoff | 544/281 |
| 5,032,592 | 7/1991 | Hughes | 514/256 |
| 5,137,887 | 8/1992 | Hashimoto | 514/246 |

FOREIGN PATENT DOCUMENTS 269859 6/1988 Japan .
1359563 10/1974 United Kingdom .

OTHER PUBLICATIONS

Abstract for JP-1-79184 (1989).
Abstract for JP-1-9971 (1989).
Derwent Abstract 89-057722/08 for JP-1-9971 (no date).

Primary Examiner—Mark L. Berch
Attorney, Agent, or Firm—Sughrue, Mion, Zinn, Macpeak & Seas

[57] ABSTRACT

The invention discloses a pyrimidien derivative expressed in Formula [I]:

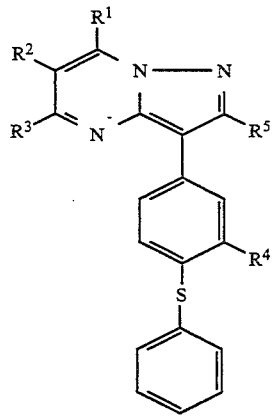

where $R^1$ denotes a hydrogen atom or hydroxyl group, $R^2$ denotes a hydrogen atom, lower alkoxycarbonyl group, lower alkoxy group, halogen atom, lower alkyl group, cycloalkyl group with 3 to 8 carbon atoms, lower alkoxycarbonyl lower alkyl group, carboxyl group, carboxy lower alkyl group, group: —CONHR⁶ ($R^6$ represents a hydrogen atom, a phenyl group, which may possess halogen atom, or lower alkyl group), cyano group, phenyl group which may possess a group se- (Abstract continued on next page.)

lected from the group consisting of hydroxyl group, halogen atom, lower alkyl group, lower alkoxy group and phenylthio group as a substituent, phenyl lower alkyl group which may possess a group selected from the group consisting of hydroxyl group and lower alkoxy group as a substituent on a phenyl ring, lower alkanoyloxy lower alkyl group, benzoyl group, lower alkanoyl group which may possess a halogen atom, or hydroxy lower alkyl group which may possess a group selected from the group consisting of phenyl group and halogen atom as a substituent, $R^3$ denotes a hydrogen atom, hydroxyl group, lower alkyl group, cycloalkyl group with 3 to 8 carbon atoms, halogen lower alkyl group, or phenyl group, $R^4$ denotes a hydrogen atom, lower alkyl group, or lower alkoxy group, and $R^5$ denotes a hydrogen atom, lower alkyl group, lower alkoxy lower alkyl group, or halogen lower alkyl group; provided that $R^2$ and $R^3$ may be bonded to each other to form a lower alkylene group with 3 to 5 carbon atoms, or its pharmaceutically available salt. This derivative is excellent in therapeutic effects of benign prostatic hypertrophy, prostatic carcinoma, female hairiness, male baldness or pimple as an androgen inhibitor.

18 Claims, No Drawings

PYRIMIDINE DERIVATIVES, METHOD OF MANUFACTURING THE SAME, AND ANDROGEN INHIBITOR

FIELD OF THE INVENTION

The present invention relates to novel pyrimidine derivatives which inhibit expression of action of androgen, method of manufacturing the same, and androgen inhibitor.

BACKGROUND OF THE INVENTION

Androgen (male hormone) is mainly synthesized in the testes of adult males, and possesses the actions for maintaining the functions of the reproductive organ and accessory reproductive organs (prostate, seminal gland), spermatogenesis, etc. If the balance of androgen and estrogen (female hormone) is broken and the action of androgen is encouraged, it is known to induce prostatic hypertrophy, prostatic carcinoma, female hairiness, male baldness or pimple. Hypertrophy of the prostate is observed in about 30% of male of 60 years or elder, and symptoms of benign prostatic hypertrophy (BPH) such as dysuria are noted in half of them.

Varieties of androgen and known to include testosterone, androstenedione, dehydroepiandrosterone, and others. It is also known that 85% of androgens synthesized in the tests of the adult men is testosterone.

The testosterone is transformed, in the cells of the prostate, into 5α-dihydrotestosterone (5α-DHT) by 5α-reductase, and is bound with a receptor to get into the nucleus, and activates the genes, thereby expressing the actions as mentioned above.

As substances inhibiting expression of such actions of androgens, for example, chlormadinone acetate, flutamide, and hydroxyflutamide are known. However, the androgen activity inhibiting actions by these compounds were not sufficiently satisfactory, the therapeutic effects on benign prostatic hypertrophy, prostatic carcinoma, female hairiness, male baldness or pimple were not sufficient.

It is hence a primary object of the invention to provide novel compounds excellent in inhibitory action of expression of actions of androgens, and excellent in therapeutic effects of benign prostatic hypertrophy, prostatic carcinoma, female hairiness, male baldness or pimple.

DISCLOSURE OF THE INVENTION

The present inventors, as a result of intensive research in order to achieve the above object, obtained a new finding that the pyrimidine derivatives expressed in Formula [I] and their pharmaceutically available salts are excellent in the effect of inhibiting the expression of action of androgens, and completed the invention.

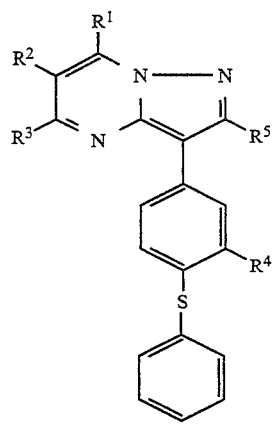

[where $R^1$ denotes a hydrogen atom or a hydroxyl group, $R^2$ denotes a hydrogen atom, lower alkoxycarbonyl group, lower alkoxy group, halogen atom, lower alkyl group, cyclocalkyl group with 3 to 8 carbon atoms, lower alkoxycarbonyl lower alkyl group, carboxyl group, carboxy lower alkyl group, group: $—CONHR^6$ ($R^6$ is hydrogen atom, phenyl group which may possess a halogen atom, or lower alkyl group), cyano group, phenyl group which may possess a group selected from the group consisting of hydroxyl group, halogen atom, lower alkyl group, lower alkoxy group and phenylthio group as substituent, phenyl lower alkyl group which may possess a group selected from the group consisting of hydroxyl group and lower alkoxy group as substituent on phenyl ring, lower alkanoyloxy lower alkyl group, benzoyl group, lower alkanoyl group which may possess a halogen atom, or hydroxy lower alkyl group which may possess a group selected from the group consisting of phenyl group and halogen atom as substituent, $R^3$ denotes a hydrogen atom, hydroxyl group, lower alkyl group, cycloalkyl group with 3 to 8 carbon atoms, halogen lower alkyl group, or phenyl group, $R^4$ denotes a hydrogen atom, lower alkyl group, or lower alkoxy group, and $R^5$ denotes a hydrogen atom, lower alkyl group, lower alkoxy lower alkyl group, or halogen lower alkyl group; provided that, $R^2$ and $R^3$ may be bound to each other to form lower alkylene group with 3 to 5 carbon atoms.]

The pyrimidine derivatives [I] of the invention and the pharmaceutically available salts are novel compounds not found in literature, and possess a strong inhibitory action on bonding of receptor in cell and 5α-DHT, bonding of receptor in cell and mibolerone, etc.

Therefore, the pyrimidine derivatives [I] of the invention and their pharmaceutically available salts are capable of inhibiting the expression of actions of androgen, and present excellent pharmaceutical effects in benign prostatic hypertrophy, prostatic carcinoma, female hairiness, male baldness, pimple or others induced by promotion of actions of androgens.

The invention also presents an androgen inhibitor possessing the compounds expressed in Formula [II] as an active ingredient.

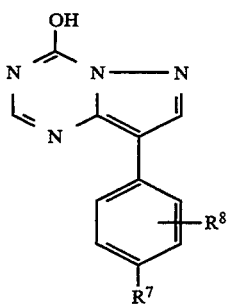

[II]

[where $R^7$ denotes a phenylthio group which may possess 1 to 3 substituents selected from the group consisting of halogen atom, lower alkyl group and lower alkoxy group as substituent on phenyl ring, phenyl lower alkylthio group which may possess 1 to 3 substituents selected from the same group as above on phenyl group, or group:

—SO$_2$NHR$^9$ (where $R^9$ is a cycloalkyl group, a pyridyl group or a phenyl group which may possess 1 to 3 groups selected from the group consisting of halogen atom, cyano group and lower alkyl group as substituent on phenyl ring), and $R^8$ denotes a hydrogen atom, lower alkoxy group, lower alkyl group or halogen atom.]

The compounds expressed in Formula [II] possess, same as the compounds expressed in Formula [I], the activity to inhibit the bonding of receptor in cell and 5-DHT, bonding of receptor in cell and mibolerone, and others. Therefore, the androgen inhibitors containing the compounds expressed in Formula [II] also inhibit the expression of actions of androgens, and present excellent therapeutic effects on benign prostatic hypertrophy, prostatic carcinoma, female hairiness, male baldness, pimple or others induced by promotion of actions of androgens.

Examples of lower alkyl group in Formulae [I] and [II] include alkyl groups with 1 to 6 carbon atoms such as methyl, ethyl, butyl, propyl, isopropyl, butyl, t-butyl, pentyl, hexyl and the like.

Examples of lower alkoxycarbonyl group are alkoxycarbonyl group with 1 to 6 carbon atoms in the alkoxy portion, such as methoxycarbonyl, ethoxycarbonyl, propoxycarbonyl, isopropoxycarbonyl, butoxycarbonyl, t-butoxycarbonyl, pentyloxycarbonyl, hexyloxycarbonyl and the like.

Examples of lower alkoxy group are alkoxy groups with 1 to 6 carbon atoms, such as methoxy, ethoxy, propoxy, isopropoxy, butoxy, t-butoxy, pentyloxy, hexyloxy and the like.

Halogen atoms include chlorine, bromine, iodine, and fluorine.

Examples of cycloalkyl groups are cycloalkyl groups with 3 to 8 carbon atoms, such as cyclopropyl, cyclobutyl, cyclopentyl, cyclohexyl, cyclooctyl and the like.

Examples of lower alkoxycarbonyl lower alkyl group are alkoxycarbonylalkyl groups with 1 to 6 carbon atoms in the alkoxy portion and 1 to 6 carbon atoms in alkyl portion, such as methoxycarbonylmethyl, methoxycarbonylethyl, ethoxycarbonylmethyl, ethoxycarbonylethyl, propoxycarbonylmethyl, propoxycarbonylethyl, isopropoxycarbonylmethyl, butoxycarbonylmethyl, t-butoxycarbonylmethyl, pentyloxycarbonylmethyl, hexyloxycarbonylmethyl, 1-ethyl-2-methoxycarbonylbutyl, hexyloxycarbonylhexyl and the like.

Examples of carboxy lower alkyl group are carboxy lower alkyl groups with 1 to 6 carbon atoms in the alkyl portion, such as carboxymethyl, carboxyethyl, 3-carboxypropyl, 1-methyl-2-carboxyethyl, 4-carboxybutyl, 1,1-dimethyl-2-carboxyethyl, 5-carboxypentyl, 6-carboxyhexyl group and the like.

Examples of phenyl group which may possess a halogen atom include 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-fluorophenyl, 4-fluorophenyl, 2,4-dichlorophenyl, 2,3-dichlorphenyl, 3,5-dichlorophenyl, 2,6-dichlorophenyl, 2,4-dibromophenyl, 2,3-dibromophenyl, 3,5-dibromophenyl, 2,4-diiodophenyl, 3,5-diiodophenyl, 2,4-difluorophenyl, 3,5-difluorophenyl, 2,3,4-trichlorophenyl, 3,4,5-trichlorophenyl, 2,3,4-tribromophenyl, 3,4,5-tribromophenyl, 2,3,4-triiodophenyl, 3,4,5-triiodophenyl, 2,3,4-trifluorophenyl, 3,4,5-trifluorophenyl and the like.

Examples of phenyl group which may possess a group selected from the group consisting of hydroxyl group, halogen atom, lower alkyl group, lower alkoxy group and phenylthio group as substituent include phenyl; 2-hydroxyphenyl, 3-hydroxyphenyl, 4-hydroxyphenyl, 3,4-dihydroxyphenyl, 3,4,5-trihydroxyphenyl; 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2,4-dichlorophenyl, 3,5-dichlorophenyl, 2-bromo-4-chlorophenyl, 3,4,5-trichlorophenyl; o-tolyl, m-tolyl, p-tolyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 4-t-butylphenyl, 2-pentylphenyl, 3-pentylphenyl, 4-pentylphenyl, 2-hexylphenyl, 3-hexylphenyl, 4-hexylphenyl, 2,4-dimethylphenyl, 3,5-dimethylphenyl, 2,4-dibutylphenyl, 3,5-dibutylphenyl, 3,4,5-trimethylphenyl, 2,3,4-trimethylphenyl; 2-methoxyphenyl, 3-methoxyphenyl, 4-methoxyphenyl, 2-ethoxyphenyl, 3-ethoxyphenyl, 3-t-butoxyphenyl, 4-ethoxyphenyl, 4-hexyloxyphenyl, 2,3-dipropoxyphenyl, 3-chloro-4-ethylphenyl; 2-hydroxy-3-pentylphenyl, 3-methyl-4-bromo-5-methoxyphenyl; phenylthiophenyl, and other phenyl groups which may possess 1 to 4 substituents selected from the group consisting of hydroxyl group, halogen atom, alkyl group with 1 to 6 carbon atoms, alkoxy group with 1 to 6 carbon atoms, and phenylthio group.

Examples of phenyl lower alkyl group which may possess a group selected from the group consisting of hydroxyl group and lower alkoxy group as substituent on phenyl ring may include benzyl, a-methylbenzyl, phenethyl, trityl, 3-phenylpropyl, phenyhexyl; 2-hydroxyphenylmethyl, 3-hydroxyphenylmethyl, 4-hydroxyphenylmethyl, 2-(2-hydroxyphenyl)ethyl, 2-(3-hydroxyphenyl)ethyl, 2-(4-hydroxyphenyl)ethyl, 3-(4hydroxyphenyl)hexyl, 3-(3,4-dihydroxyphenyl)propyl; 2-methoxyphenylmethyl, 3-methoxyphenylmethyl, 4-methoxyphenylmethyl, 4-ethoxyphenylmethyl, 3-propoxyphenylbutyl, 2-butoxyphenylhexyl, 4-hexyloxyphenylpropyl, 2,4-dibutoxyphenylpropyl, 3,5-dimethoxyphenylmethyl, 3,5-diethoxyphenylbutyl, 2,3,4-trimethoxyphenylmethyl, and other phenyl lower alkyl group with 1 to 6 carbon atoms in the alkyl portion which may possess 1 to 3 groups selected from the group consisting of hydroxyl group and alkoxy group with 1 to 6 carbon atoms at substituent on phenyl ring.

Examples of lower alkanoyloxy lower alkyl group may include acetoxymethyl, 2-acetoxyethyl, propionyloxymethyl, 2-propionyloxyethyl, 1-hexanoyloxy-2-methylpentyl, and other groups possessing lower alkanoyl portion with 2 to 6 carbon atoms and lower alkyl portion with 1 to 6 carbon atoms.

Examples of hydroxy lower alkyl group may include hydroxymethyl, 2-hydroxyethyl, 1,1-dimethyl-2-hydroxyethyl, 3-hydroxypropyl, 4-hydroxybutyl, 2-hydroxybutyl, 5-hydroxypentyl, 1-hydroxypentyl, 6-hydroxyhexyl, and other groups possessing lower alkyl portion with 1 to 6 carbon atoms.

Examples of halogen lower alkyl group include monochloromethyl, monobromomethyl, monoiodomethyl, monofluoromethyl, dichloromethyl, dibromomethyl, diiodomethyl, difluoromethyl, trichloromethyl, tribromomethyl, triiodomethyl, trifluoromethyl, monochlorethyl, monobromoethyl, monofluoroethyl, dichlorobutyl, dibromobutyl, diiodobutyl, difluorobutyl, chlorohexyl, bromohexyl, iodohexyl, fluorohexyl, and other alkyl groups with 1 to 6 carbon atoms substituting 1 to 3 halogen atoms.

Examples of lower alkoxy lower alkyl group include methoxymethyl, methoxyethyl, methoxybutyl, methoxyhexyl, ethoxymethyl, propoxyethyl, isopropoxymethyl, methoxypropyl, butoxyethyl, t-butoxyhexyl, pentyloxyethyl, hexyloxymethyl, hexyloxypropyl, and other lower alkoxy lower alkyl groups with 1 to 6 carbon atoms in both alkoxy portion and alkyl portion.

Examples of lower alkanoyl group which may possess halogen atom may include acetoxy, propionyl, butylyl, hexanoyl, monochloroacetyl, dichloroacetyl, trichloroacetyl, bromoacetyl, dibromoacetyl, tribromoacetyl, monoiodoacetyl, triiodoacetyl, monofluoroacetyl, difluoroacetyl, trifluoroacetyl, 3-chloropropionyl, 2,3-dichloropropionyl, 3,3,3-trichloropropionyl, 4-chlorobutylyl, 4-chloropentanoyl, 6-chlorohexanoyl, 3-fluoropropionyl, 4-fluorobutylyl, and other alkanoyl groups with 2 to 6 carbon atoms which may possess 1 to 3 halogen atoms.

Examples of lower alkyl group which may possess a group selected from the group consisting of phenyl group and halogen atom as substituent include hydroxymethyl, 1-hydroxyethyl, 2-hydroxyethyl, 2-hydroxy-1,1-dimethylethyl, 3-hydroxypropyl, 3-hydroxy-2-methylpropyl, 1-hydroxybutyl, 3-hydroxybutyl, 4-hydroxybutyl, 3-hydroxypentyl, 5-hydroxypentyl, 1-hydroxyhexyl, 3-hydroxyhexyl, 5-hydroxyhexyl, 6-hydroxyhexyl, α-hydroxybenzyl, 2-phenyl-2-hydroxyethyl, 2,2-diphenyl-1-hydroxyethyl, 2,2,2-triphenyl-1-hydroxyethyl, 3-phenyl-1-hydroxypropyl, 3,3-diphenyl-2-hydroxypropyl, 4-phenyl-2-hydroxypentyl, 5-phenyl-5-hydroxypentyl, 6,6,6-triphenyl-1-hydroxyhexyl, 1-phenyl-6-hydroxyhexyl; 1-hydroxy-2-chloroethyl, 1-chloro-2hydroxyethyl, 2-hydrox-2-chloroethyl, 1-hydroxy-2,2-dichloroethyl, 1-hydroxy-2,2,2-trichloroethyl, 1-hydroxy-2-bromoethyl, 1-bromo-2-hydroxyethyl, 1-hydroxy-2,2-dibromoethyl, 1-hydroxy-2,2,2-tribromoethyl, 2-hydroxy-2-iodoethyl, 1-hydroxy-2,2-diiodoethyl, 1-hydroxymethyl-2,2,2-triiodoethyl, 1-fluoro-2hydroxyethyl, 1-hydroxy-2,2,2-trifluoroethyl, 2-hydroxy-3chloropropyl, 2-hydroxy-3-dichloropropyl, 1-chloro-3-hydroxypropyl, 1-hydroxy-2,3-dibromopropyl, 2,2-dibromo-3-hydroxypropyl, 2-iodo-3-hydroxypropyl, 1-fluoro-3-hydroxypropyl, 2-hydroxy-3,3,3-trifluoropropyl, 2-hydroxymethyl-3,3,3-trifluoropropyl, 2-chloro-2-methyl-3-hydroxypropyl, 3-hydroxy-4-chlorobutyl, 2-hydroxy-4-bromobutyl, 2-hydroxy-3,4-dichlorobutyl, 2-hydroxy-4,4-difluoropentyl, 4-hydroxy-5-chloropentyl, 3-hydroxy-4-bromopentyl, 2-hydroxy-5-iodopentyl, 4-hydroxy-6-chlorohexyl, chlorohexyl, 3-hydroxy-4,4-dichlorohexyl, 3,4-dichloro-6-hydroxyhexyl, 3-hydroxy-6-fluorohexyl, 5,5-difluoro-6-hydroxyhexyl, 1-hydroxy-2-chloro-3-phenylpropyl, 1-hydroxy-3-phenyl-4-bromobutyl, and other groups with 1 to 6 carbon atoms in the alkyl portion which may possess 1 to 3 phenyl groups or halogen atoms.

Examples of phenylthio group which may possess 1 to 3 substituents selected from the group consisting of halogen atom, lower alkyl group and lower alkoxy group as substituent on phenyl ring may include phenylthio, 2-chlorophenylthio, 3-chlorophenylthio, 4-chlorophenylthio, 2-bromophenylthio, 3-bromophenylthio, 4-bromophenylthio, 4-fluorophenylthio, 4-iodophenylthio, 2,4-dibromophenylthio, 2,6-dibromophenylthio, 2,4,6-tribromophenylthio, 2-methylphenylthio, 3-methylphenylthio, 4-methylphenylthio, 2-ethylphenylthio, 4-ethylphenylthio, 3-propylphenylthio, 4-(t-butyl)phenylthio, 4-pentylphenylthio, 4-hexylphenylthio, 2,4-dimethylphenylthio, 2,6-dimethylphenylthio, 2-methyl-4-ethylphenylthio, 2,4,6-trimethylphenylthio, 2-methoxyphenylthio, 3-methoxyphenylthio, 4-methoxyphenylthio, 2-ethoxyphenylthio, 4-ethoxyphenylthio, 3-propoxyphenylthio, 4-(t-butoxy)phenylthio, 4-pentyloxyphenylthio, 4-hexyloxyphenylthio, 2,6-dimethoxyphenylthio, 2-methoxy-4-ethoxyphenylthio, 2,4,6-trimethoxyphenylthio, 2-chloro-4-methylphenylthio, 2-6-dibromo-4-methylphenylthio, 2-chloro-4-methoxyphenylthio, 2,6-dichloro-4-methoxyphenylthio, 2-bromo-4-methoxyphenylthio, 2,6-dibromo-4-methoxyphenylthio, 2,6-dibromo-4-ethoxyphenylthio, and other phenylthio groups which may possess alkyl group with 1 to 6 carbon atoms and alkoxy group with 1 to 6 carbon atoms.

Examples of phenyl lower alkylthio groups which may possess 1 to 3 substituents selected from the group consisting of halogen atom, lower alkyl group and lower alkoxy group as substituent on phenyl ring may include phenylmethylthio, 2-chlorophenylmethylthio, 3-chlorophenylethylthio, 4-chlorophenylpropylthio, 2-bromophenylbutylthio, 3-bromophenyl-t-butylthio, 4-bromophenylpentylthio, 4-fluorophenylhexylthio, 4-iodophenylmethylthio, 2,4-dibromophenylmethylthio, 2,6-dibromophenylmethylthio, 2,4,6-tribromophenylmethylthio, 2-methyphenylmethylthio, 1,3-dimethylphenylethylthio, 4-methylphenylisopropylthio, 2-ethylphenylmethylthio, 4-ethylphenylethylthio, 3-propylphenylmethylthio, 4-(t-butyl) phenylethylthio, 4-pentylphenylpropylthio, 4-hexylphenylmethylthio, 2,4-dimethylphenylmethylthio, 2,6-dimethylphenylethylthio, 2-methyl-4-ethylphenylethylthio, 2,4,6-trimethylphenylmethylthio, 2-methoxyphenylmethylthio, 3-methoxyphenylethylthio, 4-methoxyphenylmethylthio, 2-ethoxyphenylmethylthio, 4-ethoxyphenylethylthio, 3-propoxyphenylethylthio, 4-(t-butoxy)phenylpropylthio, 4-pentyloxyphenylmethylthio, 4-hexyloxyphenylmethylthio, 2,6-dimethoxyphenylethylthio, 2-methoxy-4-ethoxyphenylpropylthio, 2,4,6-trimethoxyphenylmethylthio, 2-chloro-4-methylphenylethylthio, 2,6-dibromo-4-methylphenylmethylthio, 2-chloro-4-methoxyphenylpropylthio, 2,6-dichloro-4-methoxyphenylmethylthio, 2-bromo-4-methoxyphenylmethylthio, 2,6-dibromo-4-methoxyphenylethylthio, 2,6- dibromo-4-ethoxyphenylmethyl thio group, and other phenyl lower alkylthio groups which may possess 1 to 3 substituents selected from the group consisting of halogen atom, alkyl group with 1 to 6 carbon atoms, and alkoxy group with 1 to 6 carbon atoms as substituent on phenyl ring, with 1 to 6 carbon atoms in the lower alkyl group portion.

Examples of substituent expressed in a formula:

$$-SO_2NHR^9$$

(where $R^9$ is as defined above) may include cyclopropylsulfamoyl group, cyclobutylsulfamoyl group, cyclopentylsulfamoyl group, cyclohexylsulfamoyl group, cyclooctylsulfamoyl group, and other cycloalkyl groups of which $R^9$ is 3 to 8 carbon atoms, pyridylsulfamoyl group, phenylsulfamoyl group, 4-chlorophenylsulfamoyl, 4-cyanophenylsufamoyl, 4-methylphenylsulfamoyl, 4-isopropylphenylsulfamoyl, 4-bromophenylsulfamoyl, 4-methoxyphenylsulfamoyl, 3-methylphenylsulfamoyl, 4-methylphenylsulfamoyl, 2-methylphenylsulfamoyl, 2-bromophenylsulfamoyl, 3-bromophenylsulfamoyl, 2-bromophenylsulfamoyl, 3-chlorophenylsulfamoyl, 4-iodophenylsulfamoyl, 3,5-dibromophenylsulfamoyl, 3,5-dichlorophenylsulfamoyl, 3,5-diiodophenylsulfamoyl, 2-ethylphenylsulfamoyl, 3-ethylphenylsulfamoyl, 4-propylphenylsulfamoyl, 2-butylphenylsulfamoyl, 2-propylphenylsulfamoyl, 3,5-dimethylphenylsulfamoyl, 3,5-diethylphenylsulfamoyl, 3-methyl-5-ethylphenylsulfamoyl, 3,5-dibromo-4-methylphenylsulfamoyl, 3,5-dichloro-4-ethylenephenylsulfamoyl, and other groups of which $R^9$ may possess 1 to 3 substituents selected from the group consisting of halogen atom, cyano group, and alkyl group with 1 to 6 carbon atoms as substituent on phenyl ring.

The compounds expressed in Formula [I] may include the following:
3-(4-phenylthiophenyl)pyrozolo[1,5-a]pyrimidine,
7-hydroxy-3-(4-phenylthiophenyl)pyrazolo[1,5-a]pyrimidine,
5-hydroxy-3-(4-phenylthiophenyl)pyrazolo[1,5-a]pyrimidine,
6-ethoxycarbonyl-3-(4-phenylthiophenyl)pyrazolo[1,5-a]pyrimidine,
6-ethoxycarbonyl-7-hydroxy-3-(4-phenylthiophenyl)pyrazolo[1,5-a]pyrimidine,
6-methoxy-7-hydroxy-3-(4-phenylthiophenyl)pyrazolo[1,5-a]pyrimidine,
6-fluoro-7-hydroxy-3-(4-phenylthiophenyl)pyrazolo[1,5-a]pyrimidine,
6-chloro-5-ethyl-7-hydroxy-3-(4-phenylthiophenyl)pyrazolo[1,5-a]pyrimidine,
6-phenyl-7-hydroxy-3-(4-phenylthiophenyl)pyrazolo[1,5-a]pyrimidine,
6-methyl-7-hydroxy-3-(4-phenylthiophenyl)pyrazolo[1,5-a]pyrimidine,
6-cyclohexyl-7-hydroxy-3-(4-phenylthiophenyl)pyrazolo[1,5-a]pyrimidine,
6-phenetyl-7-hydroxy-3-(4-phenylthiophenyl)pyrazolo[1,5-a]pyrimidine,
6-benzyl-7-hydroxy-3-(4-phenylthiophenyl)pyrazolo[1,5-a]pyrimidine,
6-(2-methoxyphenylmethyl)-7-hydorxy-3-(4-phenylthiophenyl)pyrazolo[1,5-a]pyrimidine,
6(3,5-dimethoxyphenylmethyl)-7-hydroxy-3-(4-phenylthiophenyl)pyrazolo[1,5-a]pyrimidine,
6-ethoxycarbonylmethyl -7-hydroxy-3-(4-phenylthiophenyl)pyrazolo[1,5-a]pyrimidine,
6-ethoxycarbonylpropyl -7-hydroxy-3-(3-methoxy-4-phenylthiophenyl)pyrazolo[1,5-a]pyrimidine,
6-carboxy-7-hydroxy-3-(3-methoxy-4-phenylthiophenyl)pyrazolo[1,5-a]pyrimidine,
6-carboxyethyl-7-hydroxy-3-(3-methoxy-4phenylthiophenyl)pyrazolo[1,5-a]pyrimidine,
6-carboxy-7-hydroxy-3-(4-phenylthiophenyl)-pyrazolo[1,5-a]pyrimidine,
6-carbamoyl-7-hydroxy-2-methyl-3-(4-phenylthiophenyl)pyrazolo[1,5-a]pyrimidine,
6-(N-phenylcarbamoyl)-7-hydroxy-3-(4-phenylthiophenyl)pyrazolo[1,5-a]pyrimidine.
6-(N-3,4,5-trichlorophenyl)carbamoyl-7-hydroxy-3-(4-phenylthiophenyl)pyrazolo[1,5-a]pyrimidine,
6-(N-ethyl)carbomoyl-7-hydroxy-3-(4-phenylthiophenyl)pyrazolo[1,5-a]pyrimidine,
6-cyano-7-hydroxy-3-(4-phenylthiophenyl)-pyrazolo[1,5-a]pyrimidine,
6-ethoxycarbonyl-5-hydroxy-3-(4-phenylthiophenyl)pyrazolo[1,5-a]pyrimidine,
5,7-dihydroxy-3-(4-phenylthiophenyl)pyrazolo[1,5-a]pyrimidine,
6-methoxycarbonyl-3-(4-phenylthiophenyl)-pyrazolo[1,5-a]pyrimidine,
5-hydroxy-6-methoxycarbonyl-3-(4-phenylthiophenyl)pyrazolo[1,5-a]pyrimidine,
5-isopropyl-6-isopropoxycarbonyl-3-(4-phenylthiophenyl)pyrazolo[1,5-a]pyrimidine,
5-hydroxy-6-hexyloxycarbonyl-3-(4-phenylthiophenyl)pyrazolo[1,5-a]pyrimidine,
7-hydorxy-5-cyclohexyl-3-(4-phenylthiophenyl)pyrazolo[1,5-a]pyrimidine,
6-hexyloxycarbonyl-3-(4-phenylthiophenyl)pyrazolo[1,5-a]pyrimidine,
7-hydroxy-3-(3-methoxy-4-phenylthiophenyl)-pyrazolo[1,5-a]pyrimidine,
7-hydroxy-6-ethoxycarbonyl-3-(3-methoxy-4-phenylthiophenyl)pyrazolo[1,5-a]pyrimidine,
7-hydroxy-3-(3,5-dimethoxy-4-phenylthiophenyl)-pyrazolo[1,5-a]pyrimidine,
3- ( 2-ethoxy-4-phenylthiophenyl)pyrazolo [1,5-a]pyrimidine,
7-hydroxy- 2-methyl -3-(4-phenylthiophenyl)-pyrazolo[1,5-a]pyrimidine,
7-hydroxy-6-ethoxycarbonyl-2-methyl-3-(4-phenylthiophenyl)pyrazolo[1,5-a]pyrimidine,
7-hydroxy-2-methoxymethyl-3-(4-phenylthiophenyl)pyrazolo[1,5-a]pyrimidine,
7-hydroxy-2-trifluoromethyl-3-(4-phenylthiophenyl)pyrazolo[1,5-a]pyrimidine,
5-methyl-2-ethoxymethyl-3-(3-methoxy-4-phenylthiophenyl)pyrazolo[1,5-a]pyrimidine,
7-hydroxy-6-ethoxycarbonyl-2-methoxymethyl-3-(4-phenylthiophenyl)pyrazolo[1,5 -a]pyrimidine,
7-hydroxy-6-ethoxycarbonyl-2-trifluoromethyl-3-(4-phenylthiophenyl)pyrazolo[1,5-a]pyrimidine,
5,7-dihydroxy-6-ethoxycarbonyl-3-(4-phenylthiophenyl)pyrazolo[1,5-a]pyrimidine,
5,7-dihydroxy-6-butoxycarbonyl-3-(4-phenylthiophenyl)pyrazolo[1,5-a]pyrimidine,
5,7-dihydroxy-6-t-butoxycarbonyl-3-(4-phenylthiophenyl)pyrazolo[1,5-a]pyrimidine,
5,7-dihydroxy-6-hexyloxycarbonyl-3-(4-phenylthiophenyl)pyrazolo[1,5-a]pyrimidine,
7-hydroxy-5-methyl-3-(4-phenylthiophenyl)-pyrazolo[1,5-a]pyrimidine,
7-hydroxy-5-cyclopropyl-3-(4-phenylthiophenyl)pyrazolo[1,5-a]pyrimidine, 7-hydroxy-5-chloromethyl-3-(4-phenylthiophenyl)-pyrazolo[1,5-a]pyrimidine,
7-hydroxy-5-phenyl-3-(4-phenylthiophenyl)-pyrazolo[1,5-a]pyrimidine,
5H-6,7-dihydro-8-hydroxy-3-(4-phenylthiophenyl)cyclopenta[d]pyrazolo[1,5-a]pyrimidine,
5-ethyl-3-(4-phenylthiophenyl)pyrazolo[1,5-a]pyrimidine,
7-hydroxy-5-trifluoromethyl-3-(4-phenylthiophenyl)-pyrazolo[1,5-a]pyrimidine,
5-methyl-6-ethoxycarbonyl-3-(4-phenylthiophenyl)-pyrazolo[1,5-a]pyrimidine,
6-acetyl-7-hydroxy-3-(4-phenylthiophenyl)-pyrazolo[1,5-a]pyrimidine,
6-benzoyl-7-hydroxy-3-(4-phenylthiophenyl)-pyrazolo[1,5-a]pyrimidine,
7-hydroxy-3-(4-phenylthiophenyl)-6-trifluoroacetyl-pyrazolo[1,5-a]pyrimidine,
7-hydroxy-6-(1-hydroxyethyl)-3-(4-phenylthiophenyl)-pyrazolo[1,5-a]pyrimidine,
7-hydroxy-6-(α-hydroxybenzyl)-3-(4-phenylthiophenyl)pyrazolo[1,5-a]pyrimidine,
7-hydroxy-6-(1-hydroxy-2,2,2-trifluoroethyl)-3-(4-phenylthiophenyl)pyrazolo[1,5-a]pyrimidine,
7-hydroxy-6-(3-bromo-4-methoxyphenyl)-3-(4-phenylthiophenyl)pyrazolo[1,5-a]pyrimidine, Typical examples of the compounds expressed in Formula [II] are shown in Table 1.

TABLE 1

| No. | $R^7$ | $R^8$ |
|---|---|---|
| 1 | 4-S—C₆H₅ | H |
| 2 | 2-CH₃-C₆H₄-S- (4-S) | H |
| 3 | 4-S—C₆H₄—CH₃ (4-) | H |
| 4 | 3-CH₃-C₆H₄-S- (4-S) | H |
| 5 | 4-S—CH₂—C₆H₅ | 3-CH₃ |
| 6 | 2-CH₃-C₆H₄-S- (4-S) | 3-CH₃ |
| 7 | 3-CH₃-C₆H₄-S- (4-S) | 3-CH₃ |
| 8 | 4-S—C₆H₄—CH₃ | 3-CH₃ |
| 9 | 3-OCH₃-C₆H₄-S- (4-S) | 3-CH₃ |
| 10 | 4-S—C₆H₄—OCH₃ | 3-CH₃ |
| 11 | 4-SO₂NH—C₆H₅ | H |
| 12 | 4-SO₂NH—C₆H₄—CH₃ | H |
| 13 | 4-SO₂NH—C₆H₄—C₂H₅ | H |
| 14 | 3-C₂H₅-C₆H₄-NHSO₂- (4-) | H |
| 15 | 2-C₂H₅-C₆H₄-NHSO₂- (4-) | H |
| 16 | 4-SO₂NH—C₆H₄—CH(CH₃)₂ | H |
| 17 | 4-SO₂NH—C₆H₄—C(CH₃)₃ | H |
| 18 | 4-SO₂NH—C₆H₄—CN | H |
| 19 | 4-SO₂NH—C₆H₄—Cl | H |

TABLE 1-continued

| No. | R⁷ | R⁸ |
|---|---|---|
| 20 | 4-SO₂NH–(3,4,5-trichlorophenyl) | H |
| 21 | 4-SO₂NH–cyclooctyl | H |
| 22 | 4-SO₂NH–(pyridin-3-yl) | H |
| 23 | 4-SO₂NH–(4-tert-butylphenyl) | 3-CH₃ |
| 24 | 4-SO₂NH–(4-bromophenyl) | 3-CH₃ |
| 25 | 4-S–phenyl | 3-OCH₃ |
| 26 | 4-S–phenyl | 3-Cl |
| 27 | 4-SO₂NH–phenyl | 3-CH₃ |
| 28 | 4-S–(3,4-diethylphenyl) | H |
| 29 | 4-S–(3,4,5-trimethylphenyl) | H |
| 30 | 4-S–(3,4,5-triethylphenyl) | H |
| 31 | 4-S–(3,4-dimethoxyphenyl) | H |
| 32 | 4-S–(2,4-dimethoxyphenyl) | H |
| 33 | 4-S–(2,3,4-trimethoxyphenyl) | H |
| 34 | 4-S–(4-ethoxyphenyl) | H |
| 35 | 4-S–(3-propoxyphenyl) | H |
| 36 | 4-S–phenyl | 3-OC₂H₅ |
| 37 | 4-S–(2-methylphenyl) | 3-OCH₃ |
| 38 | 4-S–(4-methylphenyl) | 3-OC₃H₇ |
| 39 | 4-S–phenyl | 2-OC₃H₇ |
| 40 | 4-S–CH₂–phenyl | 2-OCH₃ |
| 41 | 4-SO₂NH–phenyl | 3-Br |
| 42 | 4-SO₂NH–(4-methylphenyl) | 3-I |

TABLE 1-continued
| No. | R⁷ | R⁸ |
|---|---|---|
| 43 | 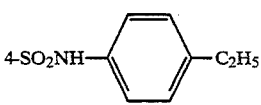 4-SO₂NH–C₆H₄–C₂H₅ | 3-F |
| 44 | 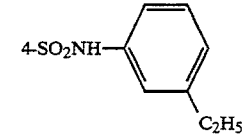 4-SO₂NH–C₆H₄–C₂H₅ | 2-Br |
| 45 | 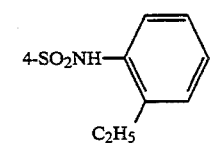 4-SO₂NH–C₆H₄–C₂H₅ | 2-I |
| 46 | 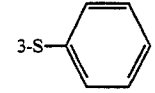 3-S–C₆H₅ | 4-CH(CH₃)₂ |
| 47 | 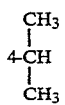 2-S–C₆H₃(Cl)(CH₃) | 3-Cl |
| 48 | 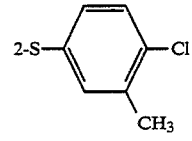 2-S–C₆H₃(C₂H₅)(Br) | 3-Br |
| 49 | 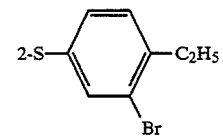 3-S–C₆H₂(CH₃)₂(F) | 2-Cl |
| 50 | 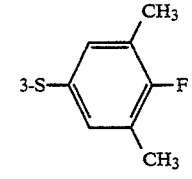 3-S–C₆H₂(C₂H₅)₃ | 2-Br |
| 51 | 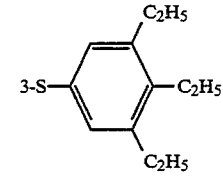 4-S–C₆H₄–OCH₃ | H |
| 52 | 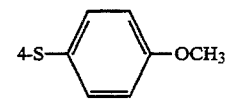 4-S–C₆H₃(OCH₃)(CH₃) | H |
| 53 | 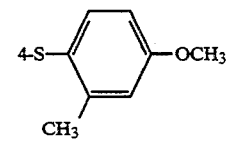 4-S–C₆H₃(CH₃)(OCH₃) | H |
| 54 | 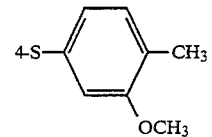 4-S–C₆H₃(OCH₃)(CH₃) | H |
| 55 | 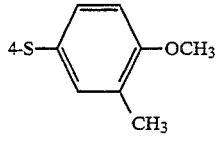 4-S–CH₂–C₆H₄–OCH₃ | H |
| 56 | 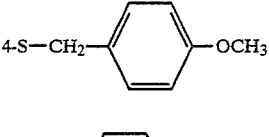 4-S–C₆H₄–C₂H₅ | H |
| 57 | 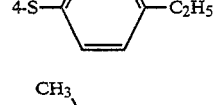 4-S–C₆H₃(CH₃)(C₂H₅) | H |
| 58 | 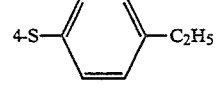 4-S–C₆H₃(C₂H₅)(CH₃) | H |
| 59 | 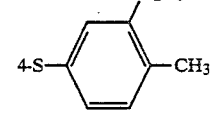 4-S–C₆H₃(CH₃)(C₂H₅) | H |
| 60 | 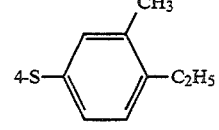 4-S–CH₂–C₆H₄–C₂H₅ | H |
| 61 | 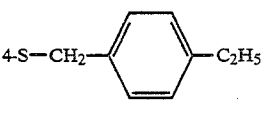 4-SO₂NH–C₆H₅ | H |
| 62 | 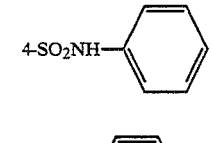 4-SO₂NH–C₆H₄–CH₃ | H |
| 63 | 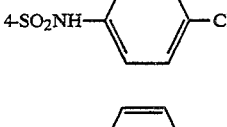 4-SO₂NH–C₆H₄–C₂H₅ | H |
| 64 | 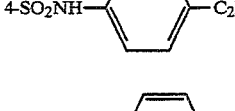 4-SO₂NH–C₆H₄–C₂H₅ | H |

TABLE 1-continued

| No. | R⁷ | R⁸ |
|-----|----|----|
| 65 | 4-SO₂NH–(phenyl with 2-C₂H₅) | H |
| 66 | 4-SO₂NH–(phenyl with 3-CN, 4-CH(CH₃)₂) | H |
| 67 | 4-SO₂NH–(phenyl with 3-CN, 4-C(CH₃)₃) | H |
| 68 | 4-SO₂NH–(phenyl with 3-CN, 4-CN) | H |
| 69 | 4-SO₂NH–(phenyl with 3-CN, 4-Cl) | H |
| 70 | 4-SO₂NH–(phenyl with 3-Cl, 4-CN, 5-Cl) | H |
| 71 | 4-SO₂NH–cyclohexyl | H |
| 72 | 4-SO₂NH–(2-pyridyl) | 3-CH₃ |
| 73 | 4-SO₂NH–(phenyl with 3-C(CH₃)₃, 4-CN) | 3-CH₃ |
| 74 | 4-SO₂NH–(phenyl with 3-Br, 4-CN) | 3-CH₃ |
| 75 | 4-S–(phenyl with 4-C₂H₅) | 3-OCH₃ |
| 76 | 4-S–(phenyl with 4-CH₃) | 3-Cl |
| 77 | 4-SO₂NH–(phenyl with 4-CN) | 3-CH₃ |
| 78 | 4-S–(phenyl with 3-C₂H₅, 4-C₂H₅) | 3-OCH₃ |
| 79 | 4-S–(phenyl with 2-CH₃, 3-CH₃, 4-CH₃) | 2-CH₃ |
| 80 | 4-S–(phenyl with 2-C₂H₅, 3-C₂H₅, 4-C₂H₅) | 3-OC₂H₅ |

The compounds of the invention expressed in Formula [I] may be manufactured in various methods, for example, in the method illustrated in the following reaction schemes 1 to 20.

Reaction scheme 1

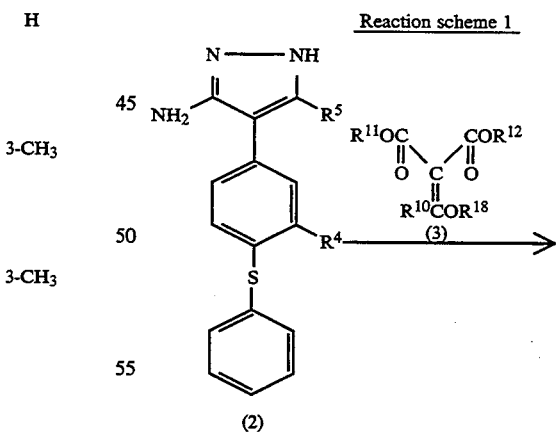

Reaction scheme 1 -continued

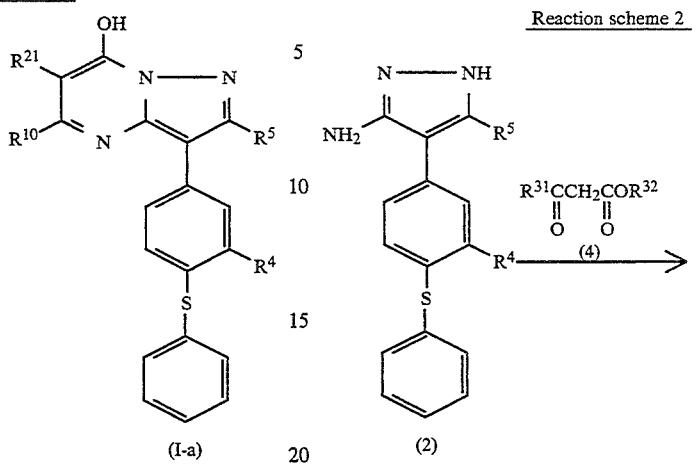

(I-a)

(wherein $R^{21}$ denotes a lower alkoxycarbonyl group, $R^{11}$, $R^{12}$ and $R^{18}$ indicate same or different, lower alkyl groups, $R^{10}$ denotes a hydrogen atom or lower alkyl group, and $R^4$ and $R^5$ are same as defined above.)

This reaction is to obtain the compound of the invention expressed in Formula (I-a) by reaction of the compound expressed in Formula (2) and the compound expressed in Formula (3) in the presence of an acid without solvent or in a proper solvent.

Examples of the solvent may include pyridine, chloroform, dichloromethane or other halogenated hydrocarbons, dioxane, tetrahydrofuran (THF) or other ethers, benzene, toluene or other aromatic hydrocarbons, N,N-dimethylformamide (DMF), dimethylsulfoxide (DMSO), acetonitrile or other non-protic polar solvents. Examples of acids may include Lewis acids such as anhydrous aluminium chloride, stannic chloride, titanium tetrachloride, boron trichloride, boron trifluorideethylether complex and zinc chloride, inorganic acids such as phosphoric acid, hydrochloric acid, nitric acid and sulfuric acid, and organic acids such as trichloroacetic acid, trifluoroacetic acid, methansulfonic acid and acetic acid.

The molar ratio of the compound (3) to the compound (2) may be at least an equimolar amount, or preferably 1:1 to 1.5:1. The molar ratio of the acid to the compound (2) is 1:1 to 50:1, preferably 1:1 to 20:1. The reaction is usually performed at 50° to 150° C., preferably 80° to 120° C., and is terminated in about 1 to 6 hours.

In this reaction, as the byproduct of the compound expressed in Formula (1-a), a compound of which hydroxyl group portion of pyrimidine ring in Formula (I-a) is either hydrogen atom or lower alkyl group and $R^{10}$ portion is hydroxyl group is obtained at the same time. They are separated by various known methods, for example, by making use of the difference in solubility of solvents such as alcohols.

Reaction scheme 2

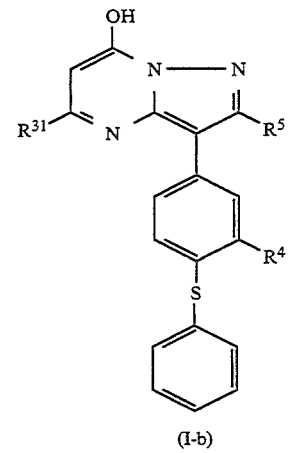

(I-b)

(where $R^{31}$ and $R^{32}$ are same or different, lower alkyl groups, and $R^4$ and $R^5$ are same as defined above.)

This reaction is to obtain the compound of the invention expressed in Formula (I-b) by reaction of the compound expressed in Formula (2) and the compound expressed in Formula (4) in the presence of an acid without solvent or in a proper solvent.

Examples of solvent and acid used in the reaction may be same as exhibited in Reaction scheme 1.

The molar ratio of the compound (4) and compound (2) may be at least an equimolar amount, preferably 1 to 1.5 times. The molar ratio of the acid to the compound (2) may be 1:1 to 100:1, preferably 1:1 to 50:1. The reaction is usually performed at 50° to 150° C., preferably 80° to 120° C., and is terminated in about 1 to 5 hours.

Reaction scheme 3

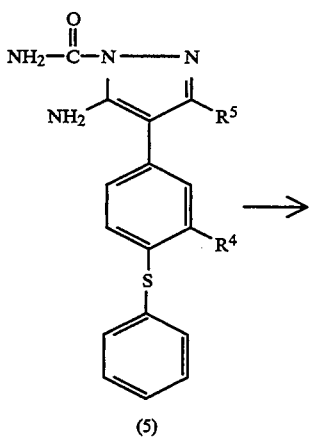

(5)

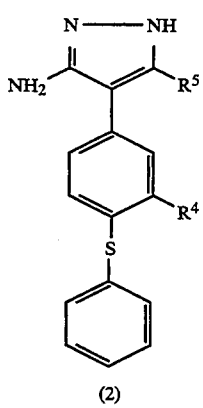

(2)

(where $R^4$ and $R^5$ are same as defined above.)

This reaction is to obtain the compound expressed in Formula (2) from the compound expressed in Formula (5) in the presence of a base without solvent or in a proper solvent.

The base used in the reaction may include, for example, alkali metal hydroxide such as sodium hydroxide and potassium hydroxide, alkali metal carbonate such as sodium carbonate and potassium carbonate, alkali metal hydrogencarbonate such as sodium hydrogencarbonate and potassium hydrogencarbonate, and other inorganic bases.

As the solvent, any solvents may be used so far as not to affect the reaction, including, for example, lower aliphatic alcohol such as methanol and ethanol, and mixed solvent of lower aliphatic alcohol and water. When such mixed solvent is used, the mixing rate of the lower aliphatic alcohol and water may be in a range of 1:1 to 10:1.

The molar ratio of the basic compound to the compound (5) is 1 to 50 times, preferably 1:1 to 20:1. The reaction temperature is room temperature to 100° C., preferably 30 to 100° C. The reaction time is about 10 to 120 minutes.

Reaction scheme 4

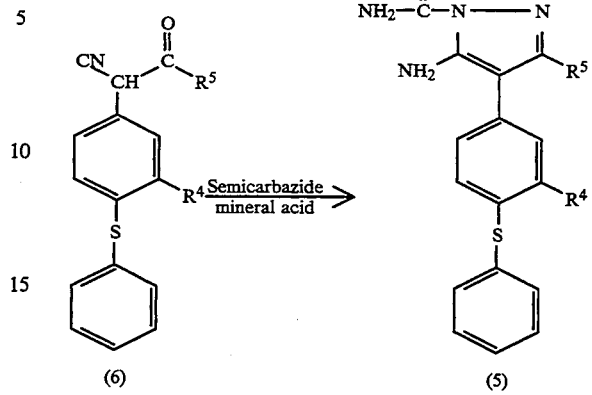

(6)                                    (5)

(where $R^4$ and $R^5$ are same as defined above.)

This reaction is to obtain the compound expressed in Formula (5) by reaction of the compound expressed in Formula (6) with semicarbazide mineral acid salt by dropping in ice-chilled at least by an equimolar amount, preferably in a molar ratio of 1:1 to 1.2:1, and then continuing to react at room temperature for about 4 to 15 hours.

The solvent used in the reaction may be any material so far as not to affect the reaction, including, for example, lower aliphatic alcohol such as methanol and ethanol, and mixed solvent of lower aliphatic alcohol and water. In the case of mixed solvent, the mixing rate of lower aliphatic alcohol and water may be in a range of about 1:1 to 10:1.

Reaction scheme 5

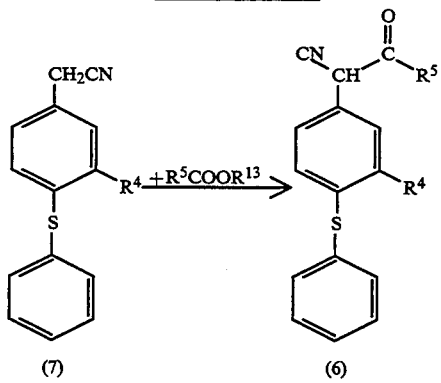

(7)                                    (6)

(where $R^{13}$ denotes a lower alkyl group, and $R^4$ and $R^5$ are same as defined above.)

This reaction is to obtain the compound of Formula (6) by reaction of the acetonitrile derivative expressed in Formula (7) and a specific ester.

If ethyl formate is used as the ester, the group $R^5$ is a hydrogen atom. Examples of formic ester may include methyl formate, ethyl formate and the like.

The reaction is performed in an inert solvent. Examples available as inert solvent may include aromatic hydrocarbons such as benzene, toluene and xylene, ethers such as diethylether, tetrahydrofuran and dioxane, N,N-dimethylformamide, dimethylsulfoxide, and the like. The molar ratio of the ester to the compound (7) may be at least an equimolar amount, preferably 1.05:1 to 1.20:1. The reaction is first performed in ice-chilled state for about 5 to 20 minutes, then at room temperature for about 4 to 15 hours, preferably. In order to progress the reaction sufficiently, sodium alkoxide such as sodium methoxide, or metal hydride such as sodium hydride should be preferably added to the ester by at least an equimolar amount.

The reaction product is obtained by using column chromatogrphy after the usual treatments.

Reaction scheme 6

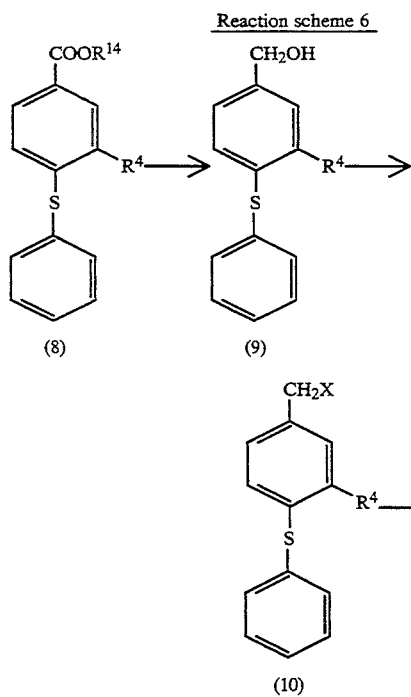

(where X denotes a halogen atom, $R^{14}$ denotes a lower alkyl group, and $R^4$ is same as defined above.)

This reaction is to obtain the compound expressed in Formula (9) by reducing the compound expressed in Formula (8) by using a hydrogenation reducing agent, obtain the compound expressed in Formula (10) by reaction of the compound expressed in Formula (9) with a halogenation agent, and obtain the compound (7) which is the starting material of Reaction scheme 5 by reaction of the compound (10) by a cyanide compound.

The reaction to obtain compound (9) from compound (8) is performed in a proper solvent. Examples of such solvent may include ethers such as diethylether, tetrahydrofuran, dioxane and diglyme; aliphatic hydrocarbons such as hexane and heptane; and aromatic hydrocarbons such as benzene and toluene. Examples of hydrogenation reducing agent used in the reaction may include lithium aluminium hydride, aluminum hydride, diisopropyl aluminium hydride, lithium borohydride, sodium borohydride-aluminium chloride, diborane and the like. Hydrogenation reducing agent and the compound (8) is present in a molar ratio of at least 0.5:1, preferably 0.6:1 to 1.2:1. The reaction is usually carried out at 0° to 100° C., or preferably about 0° to 50° C., and is terminated in about 30 minutes to 10 hours.

The reaction to obtain compound (10) from compound (9) is performed without solvent or in a proper solvent. Examples of the solvent used in this reaction may include ethers such as diethylether, tetrahydrofuran and dioxane, halogenated hydrocarbons such as methylene chloride, chloroform and dichloroethane, and aromatic hydrocarbons such as benzene and toluene. The halogenating agent used in the reaction may include, for example, halogenated thionyl such as thionyl chloride and thionyl bromide, hydrogen halide such as hydrogen chloride, hydrogen bromide and hydrogene iodide, and phosphorus halide such as phosphorus trichloride and phosphorus tribromide. The molar ratio of the halogenating agent to the compound (9) is at least an equimolar amount, preferably 1:1 to 1.3:1. The reaction is performed at 0° to 100° C., or preferably 0° to 50° C., and is terminated in about 30 minutes to 5 hours.

The reaction to obtain compound (7) from compound (10) is performed in a proper solvent. Examples of the solvent used in the reaction may include lower alcohol such as methanol, ethanol and propanol, non-protic polar solvent such as acetone, N,N-dimethylformamide (DMF), dimethylsulfoxide (DMSO) and hexamethylphosphate triamide (HMPA), and mixed solvents of them and water. Cyanide compounds used in the reaction may include potassium cyanide, sodium cyanide, silver cyanide, copper cyanide, calcium cyanide and the like. The molar ratio of cyanide compound to the compound (10) is at least an equimolar amount, preferably 1:1 to 1.3:1. The reaction is performed at room temperature to 150° C., preferably room temperature to 100° C., and is terminated in about 1 to 24 hours.

Reaction scheme 7

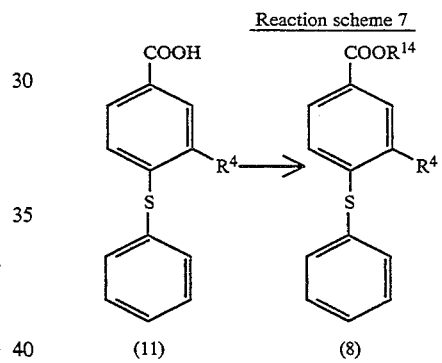

(where $R^{14}$ and $R^4$ are same as defined above.)

This reaction is to obatin the compound expressed in Formula (8) which is the starting material of Reaction scheme 6, by esterifying the compound expressed in Formula (11) in 5 ordinary reaction.

The esterification is carried out, for example, by reacting the compound (11) with an alcohol expressed in a formula:

$$R^{14}-OH$$

(where $R^{14}$ is same as defined above) in the presence of a catalyst. As the catalyst, a general catalyst for esterification is used, for example, inorganic acid such as hydrogen chloride, concentrated sulfuric acid, phosphoric acid, polyphosphoric acid, boron trifluoride and perchloric acid; organic acid such as trifluoroacetic acid, trichloromethanesulfonic acid, naphthalenesulfonic acid, p-toluenesulfonic acid, benzenesulfonic acid and ethanesulfonic acid; acid anhydrides such as trichloromethanesulfonic acid anhydride and trifluoromethane sulfonic acid anhydride, thionyl chloride, etc. Besides, a cationic exchange resin (acid type) may be also used. The esterification is done without solvent or in the presence of a proper solvent. The available solvents are any solvent generally used in esterification, such as aromatic hydrocarbons such as benzene, toluene and xylene, halogenated hydrocarbons such as dichloromethane, dichloroethane and chloroform, and ethers such as diethylether, tetrahydrofuran and dioxane. The molar ratio of the acid to the compound (11) is 1:1 to 100:1, preferably 10:1 to 30:1. The reaction temperature is $-20°$ C. to $200°$ C., preferably $0°$ to $150°$ C.

Incidentally, the compound (8) may be also obtained by the method of reaction of the alkali metal salt of compound (11) (for example, sodium salt, potassium salt) with a halide compound expressed in a formula:

$$R^{14}-X$$

(where $R^{14}$ is same as defined above), the method of reaction of compound (11) with diazoalkane such as diazomethane, diazoethane and diazopropane, or the method of reaction with an alcohol expressed in a formula:

$$R^{14}-OH$$

(where $R^{14}$ is same as defined above) after converting the carboxyl group of compound (11) into a reactive group (acid chloride or anhydride), among others. These esterifications may be done according to the conventional method.

Reaction scheme 8

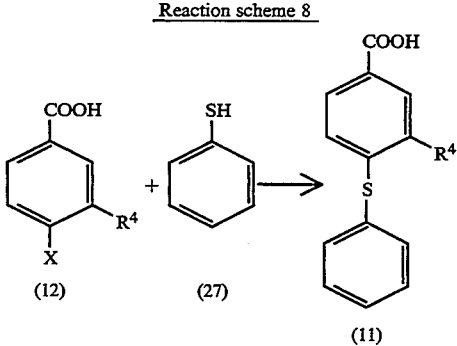

(11)

(where X and $R^4$ are same as defined above.)

This reaction is to obtain the compound expressed in Formula (11) which is the starting material for Reaction scheme 7, by the reaction of the benzoic acid derivative expressed in Formula (12) and phenylthio derivative expressed in Formula (27). This reaction is performed in the presence f a base such as sodium hydroxide and potassium hydroxide in a proper solvent. Examples of available solvent are N,N-dimethylformamide (DMF), N,N-dimethylacetamide, dimethyl sulfoxide (DMSO), hexamethyl phosphoric triamide (HMPA), and other nonprotic polar solvent.

The molar ratio of the compound (27) to the compound (12) is equimolar, preferably slightly in excess. The basic compound may be used at least 2 times mol or preferaly in excess slightly to the compound (12) in order to form the salt of compound (12) and compound (27). The reaction is performed at room temperature to $180°$ C., and is terminated in about 30 minutes to 24 hours.

Reaction scheme 9

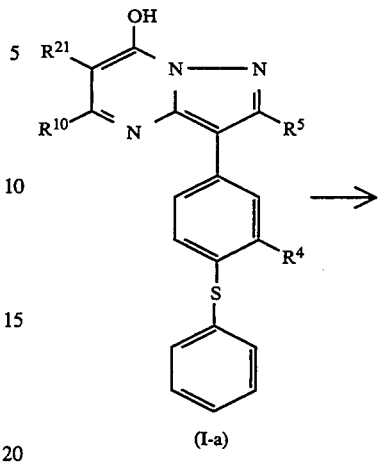

(I-a)

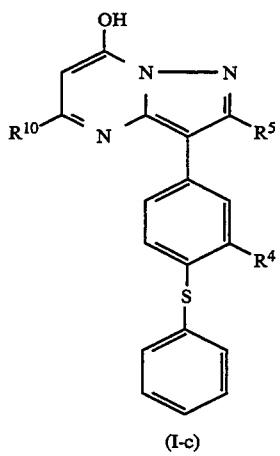

(I-c)

(where $R^{10}$, $R^4$, $R^5$ and $R^{21}$ are same as defined above.)

This reaction is to obtain the compound expressed in Formula (1-c) by dissociating the lower alkoxycarbonyl group expressed by group $R^{21}$ from the compound (1-a) obtained in Reaction scheme 1. The reaction is performed in the presence of an acid without solvent or in a proper solvent.

As the solvent, any solvent may be used so far as not to adversely affect the reaction, including, for example, ethers such as diethylether, tetrahydrofuran and dioxane, halogenated hydrocarbons such as dichloromethane, dichloroethane, chloroform and carbon tetrachloride, aromatic hydrocarbons such as benzene, toluene and xylene, amines such as pyridine, pyperidine and triethylamine, aliphatic hydrocarbons such as hexane and heptane, alcohols such as methanol, ethanol and propanol, non-protic polar solvents such as dimethylformamide, hexamethyl phosphoric triamide (HMPA) and dimethylsulfoxide (DMSO), carbon disulfide, water, etc.

The available acids are as those presented in Reaction scheme 1.

The molar ratio of acid or base to the compound (1-a) is 1:1 to 200:1, preferably 1:1 to 100:1. The reaction is performed at room temperature to $200°$ C., preferably $50°$ to $200°$ C., and is terminated in 5 minutes to 5 hours, preferably 10 minutes to 3 hours.

Reaction scheme 10

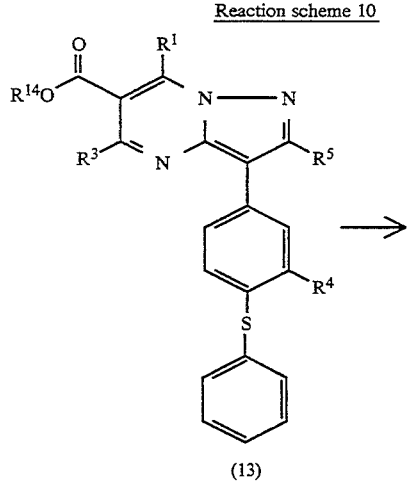

(13)

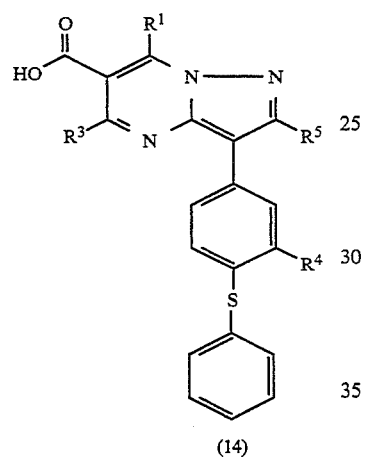

(14)

(where $R^1$, $R^3$, $R^4$, $R^5$ and $R^{14}$ are same as defined above)

This reaction is to obtain the compound expressed in Formula (14) by hydrolysis of the compound expressed in Formula (13). The reaction is performed in the presence of a basic compound or an acidic compound in a proper inert solvent. Examples of inert solvent include alcohols such as methanol and ethanol, and ethers such as dimethylether, diethylether, tetrahydrofurane, dioxane and anisol. Examples of basic compound include trialkylamine such as triethylamine and tributylamine, organic base such as pyridine, picoline, 1,5-diazabicyclo[4.3.0]non-5-ene, 1,4-diazabicyclo[2.2.2]octane and 1,8-diazabicyclo[5.4.0]undec-7-ene, alkali metal hydroxide such as sodium hydroxide and potassium hydroxide, alkali metal carbonate such as sodium carbonate and potassium carbonate, alkali metal hydrogencarbonate such as sodium hydrogencarbonate and potassium hydrogencarbonate. Examples of acidic compound include Lewis acid such as anhydrous aluminium chloride, stannic chloride, titanium tetrachloride and boron trichloride, inorganic acid such as hydrochloric acid, hydrobromic acid, nitric acid and sulfuric acid, organic acid such as trichloroacetic acid, trifluoroacetic acid, methansulfonic acid, acetic acid and formic acid, and cationic exchange resin (acid type) ion exchange resin. The molar ratio of the basic compounds or acidic compounds to the compound (13) is 1:1 to 100:1, preferably 1:1 to 20:1. The reaction is performed at −20° C. to 100° C., preferably −10° to 80° C., for about 30 minutes to 48 hours, preferably 1 to 24 hours.

Reaction scheme 11

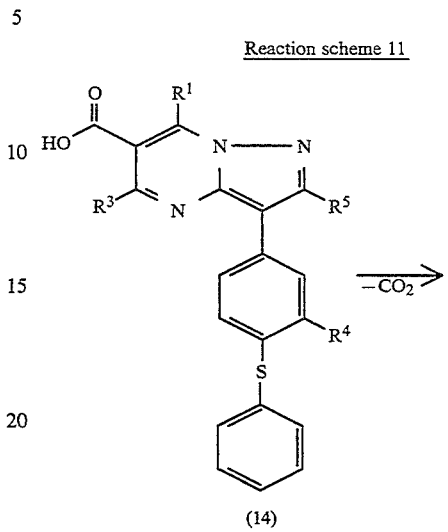

(14)

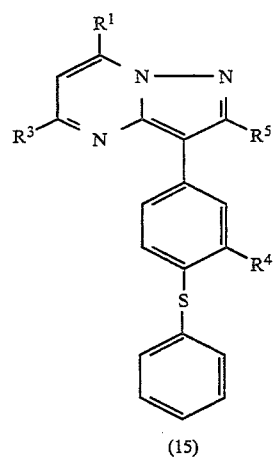

(15)

(where $R^1$ $R^3$ $R^4$ and $R^5$ are same as defined above.)

This reaction is to obtain the compound expressed in Formula (15) by decarboxylation from the compound expressed in Formula (14) obtained in Reaction scheme 10. The reaction is performed in the presence of a basic compound without solvent or putting the compound (14) in a proper solvent. The reaction may be performed in a sealed tube if necessary. Examples of basic compound may include aniline, N,N-dimethylaniline, N,N-diethylaniline, N-methylaniline, N-ethylaniline, pyridine, α-picoline, β-picoline, γ-picoline, 2,3-lutidine, 2,4-lutidine, 2,5-lutidine, 2,6-lutidine, 3,4-lutidine, 3,5-lutidine, triethylamine, diethylamine, ethylamine, methylamine, ammonia, etc.

The reaction is performed at 0° to 150° C., preferably 30° to 100° C., for about 10 minutes to 12 hours, or preferably about 30 minutes to 6 hours.

Reaction scheme 12

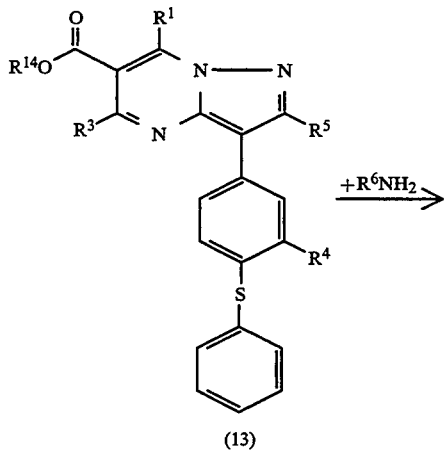

(13)

+R⁶NH₂ →

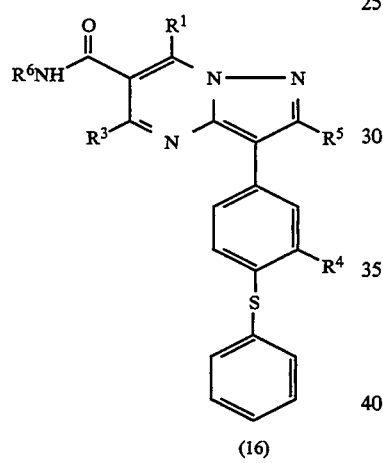

(16)

(where $R^1$, $R^3$, $R^4$, $R^5$ $R^6$ and $R^{14}$ are same as defined above.)

This reaction is to obtain the compound expressed in Formula (16) by reaction of the compound expressed in Formula (13) with amine $R^6NH_2$. The reaction is performed without solvent or in a proper solvent. When, for example, aniline is used as amine, the product is the compound (16) of which $R^2$ in Formula [I] is N-phenyl-carbamoyl group. The molar ratio of the amine to the compound (13) is 1:1 to 100:1, preferably 10:1 to 50:1.

The reaction is performed at 0° to 200° C., preferably 100° to 180° C., for about 10 minutes to 5 hours, preferably about 30 minutes to 3 hours.

Reaction scheme 13

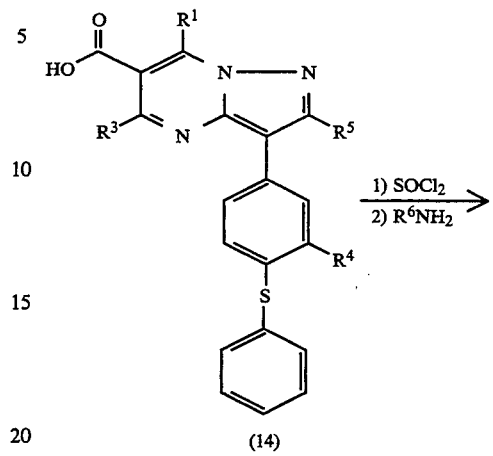

(14)

1) SOCl₂
2) R⁶NH₂
→

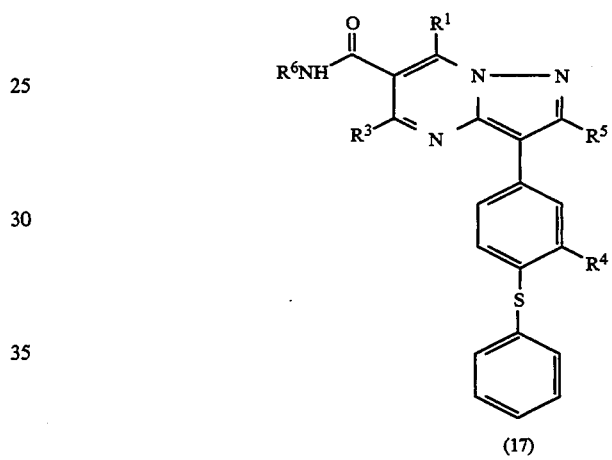

(17)

(where $R^1$, $R^3$, $R^4$, $R^5$ and $R^6$ are same as defined above.)

This reaction is to obtain the compound expressed in Formula (17) possessing the group: R⁶NHCO— by transforming the carboxyl group of the compound expressed in Formula (14) into chloroformyl group by thionyl chloride, and reacting with amine R⁶ NH₂. The reaction is performed without solvent or in a proper solvent.

The molar ratio of thionyl chloride to the compound (14) is 1:1 to 100:1, preferably 2:1 to 10:1. The reaction is performed at −10° to 100° C., preferably −5° to 25° C., for about 5 minutes to 10 hours, preferably about 10 minutes to 3 hours. Instead of thionyl chloride, meanwhile, phosphorus trichloride, phosphorus pentachloride or the like may be used.

The molar ratio of the amine to the product transforming the carboxyl group into chloroformyl is 1:1 to 50:1, preferably 1:1 to 3:1. The reaction is performed at −10° to 100° C., or preferably −5° to 25° C., for about 5 minutes to 20 hours, preferably about 10 minutes to 3 hours.

Reaction scheme 14

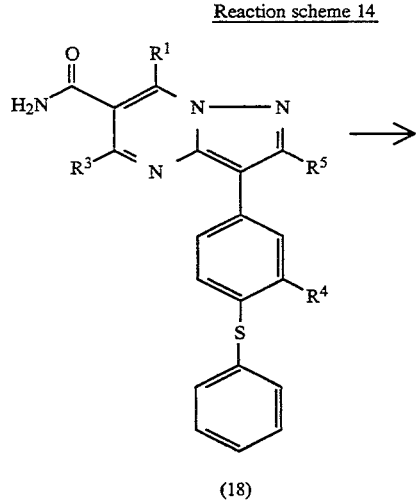

(18)

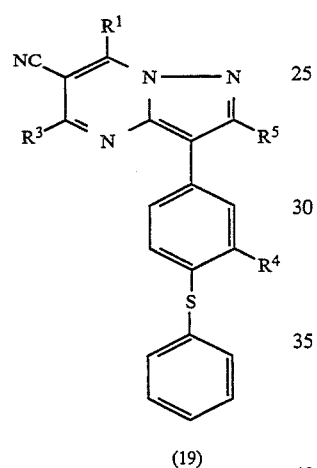

(19)

(where $R^1$, $R^3$, $R^4$ and $R^5$ are same as defined above.)

This reaction is to obtain the compound expressed in Formula (19) by transforming the carbamoyl group of the compound expressed in Formula (18) into cyano group by thionyl chloride. The reaction is performed without solvent or in a proper solvent.

The molar ratio of thionylchloride to the compound (18) is 1:1 to 50:1, preferably 2:1 to 10:1. The reaction is performed at $-10°$ to $100°$ C., preferably $0°$ C. to room temperature, for about 5 minutes to 20 hours, preferably about 10 minutes to 5 hours.

The available solvents are same as listed, for example, in Reaction scheme 1. Instead of thionyl chloride, phosphorus pentachloride, phosphoryl chloride, phosphorus pentoxide or the like may be used.

Reaction scheme 15

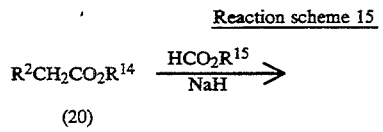

(20)

-continued
Reaction scheme 15

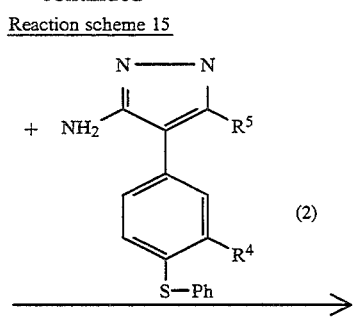

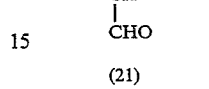

(21)

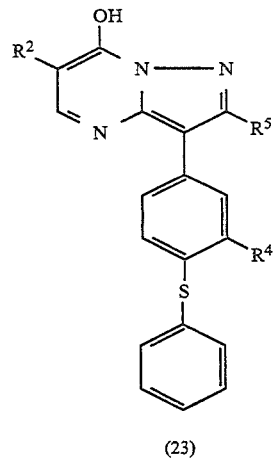

(23)

(where $R^2$, $R^4$, $R^5$ and $R^{14}$ are same as defined above Ph denotes a phenyl group, and $R^{15}$ indicated a lower alkyl group.)

This reaction is to obtain the compound (21) in which a formyl group is introduced at α-position thereof by reaction of ester compound expressed in Formula (20) with formic ester, and obtain the compound of the invention expressed in Formula (23) by reacting the compound (21) with a compound expressed in Formula (2).

The reaction for introducing formyl group is performed in the presence of sodium hydride in a proper inert solvent. The molar ratio of formic ester to the ester (20) is 1:1 to 5:1, preferably 1:1 to 2:1. The molar ratio of sodium hydride to the ester compounds is 1:1 to 5:1, preferably 1:1 to 2:1. The available solvents are same as listed in Reaction scheme 1, for example. The reaction is performed at $0°$ to $100°$ C., preferably $0°$ to $40°$ C., for about 1 to 48 hours, preferably about 5 to 24 hours.

The produced compound (21) may be used in the next reaction with the compound (2) by isolating or without isolating from the reaction solution. The molar ratio of the compound (2) to the compound (21) is 0.1:1 to 1:1, preferably 0.5:1 to 1:1. The reaction is performed at $30°$ to $120°$ C., or preferably $80°$ to $120°$ C., for about 30 minutes to 10 hours, preferably about 3 to 5 hours.

Reaction scheme 16

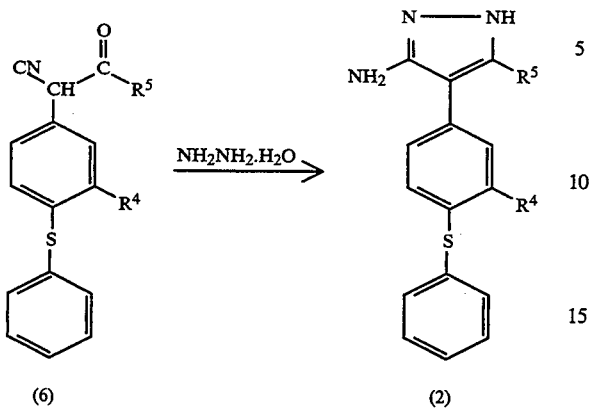

(where $R^4$ and $R^5$ are same as defined above.)

This reaction is to obtain the compound expressed in Formula (2) directly from the compound expressed in Formula (6). That is, the compound (6) is reacted with hydrazine $NH_2NH_2.H_2O$ or its dihydrochloride or sulfate in the presence of acetic acid or mineral acid. This hydrazine is used at a molar ratio of 1:1 to 2:1, and the reaction may be performed at room temperature to 100° C. The molar ratio of acetic acid or mineral acid to hydrazine $NH_2NH_2.H_2O$ is 1:1 to 2:1.

Reaction scheme 17

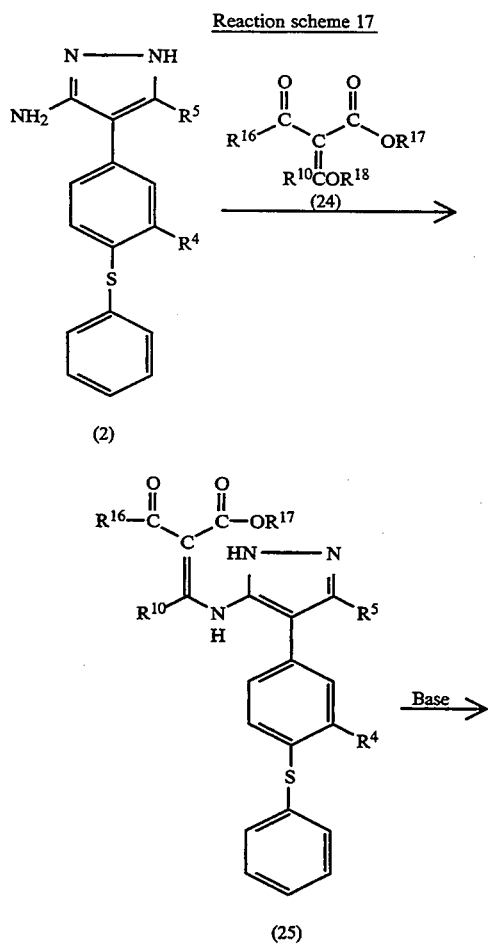

-continued
Reaction scheme 17

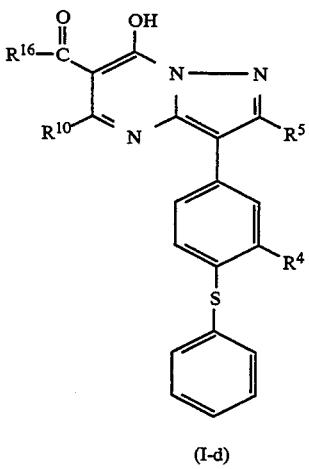

(where $R^{10}$, $R^4$ and $R^5$ are same as defined above, and $R^{16}$, $R^{17}$ and $R^{18}$ are same or different lower alkyl groups.)

This reaction is to obtain the compound expressed in Formula (I-d) from the compound expressed in Formula (2) by way of the compound expressed in Formula (25). The reaction from the compound (2) to the compound (25) is basically same as in Reaction scheme 1. That is, the compound (2) and compound (24) react with each other in the presence of an acid without solvent or in a proper solvent to precipitate the compound (25). The available solvent and acid and the ratio of compound (2) to compound (24) may be same as in Reaction scheme 1. The reaction is performed usually at room temperature to 140° C., preferably room temperature to 80° C., and is terminated in 5 minutes to 2 hours.

After reaction, the produced compound (25) is isolated from the reaction solution, washed, and is caused to react in the presence of a base in a solvent to obtain the compound (I-d). Examples of solvent include lower aliphatic alcohols such as methanol, ethanol and isopropanol, ethers such as dioxane and tetrahydrofuran (THF), aromatic hydrocarbons such as benzene and toluene, and non-protic polar solvents such as N,N-dimethylformamide (DMF) and dimethylsulfoxide (DMSO).

Examples of available base include sodium ethoxide, other sodium alkoxide, sodium hydride and others. The molar ratio of the base to the compound (25) is an equimolar amount, preferably 1:1 to 3:1. The reaction is done usually at 0° to 100° C., preferably 0° to 50° C., and is terminated in about 1 to 72 hours, or preferably 10 to 48 hours.

Reaction scheme 18

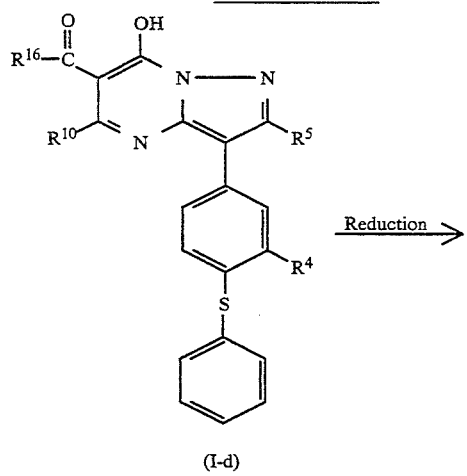

(I-d)

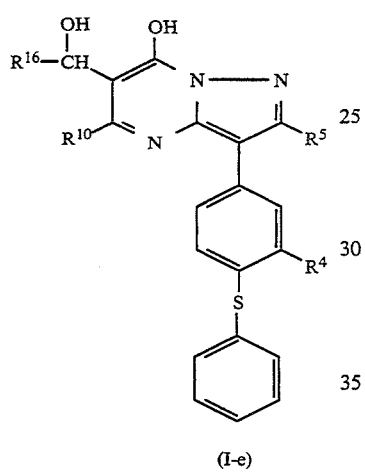

(I-e)

(where $R^4$, $R^5$, $R^{10}$ and $R^{16}$ are same as defined above.)

This reaction is to obtain the compound expressed in Formula (I-e) by reducing the compound expressed in Formula (I-d). The reaction is performed in the presence of a reducing agent in a proper solvent. Examples of available solvent include lower aliphatic alcohol such as methanol, ethanol and isopropanol, ethers such as diethyleneglycol dimethylether, aromatic hydrocarbons such as benzene and toluene, non-protic polar solvents such as N,N-dimethylformamide (DMF) and dimethylsulfoxide (DMSO), and water.

Examples of the reducing agent may include lithium aluminium hydride, sodium borohydride, diborane and aluminium isobutylhydride. When sodium borohydride is used as reducing agent, a preferable solvent to be used is a mixed solvent of lower aliphatic alcohol such as methanol and ethanol with water. The mixing rate of lower aliphatic alcohol and water is preferred to be about 1:1 to 10:1. For stabilization of sodium borohydride, moreover, it is desired to add a base. Such base may be, for example, alkali metal hydroxide such as sodium hydroxide and potassium hydroxide. The molar ratio of base to sodium borohydride is 1:1 to 50:1, preferably 1:1 to 10:1.

The reaction is carried out at 0° to 150° C., preferably 30° to 100° C., and is terminated in about 30 minutes to 5 hours.

Reaction scheme 19

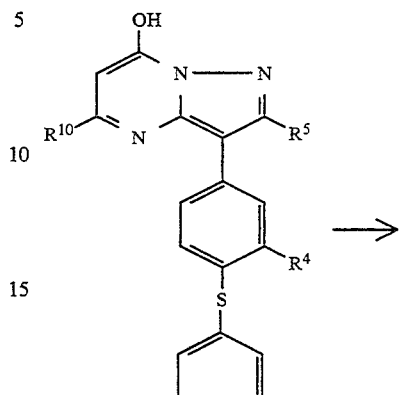

(I-c)

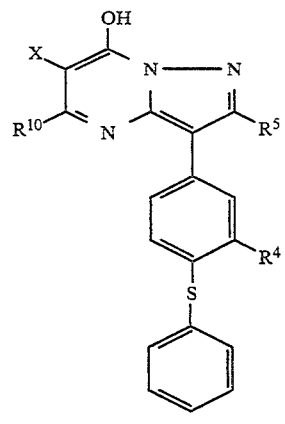

(I-f)

(where X denotes a halogen atom, and $R^{10}$, $R^4$ and $R^5$ are same as defined above.)

This reaction is to obtain the compound expressed in Formula (I-f) by reacting the compound expressed in Formula (I-c) with halogenating agent without solvent or in a proper solvent.

Examples of the solvent may be same as used in Reaction scheme 1. The halogenating agent may include N-bromosuccinimide, N-chlorosuccinimide, N-bromocaprolactam, 1,3-dibromo-5,5-dimethyl hydrantoin, bromine, chlorine, and sulfuryl chloride.

The molar ratio of halogenating agent to the compound expressed in Formula (I-c) is 1:1 to 2:1, preferably 1:1 to 1.5:1.

The reaction is performed at 0° to 50° C., preferably 0° C. to room temperature, and is terminated in about 30 minutes to 5 hours.

Reaction scheme 20

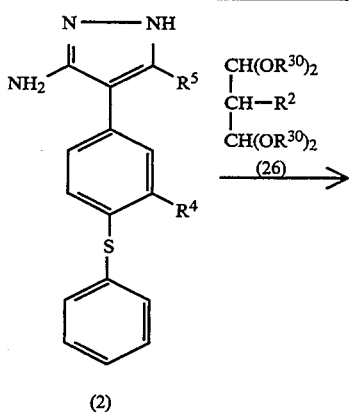

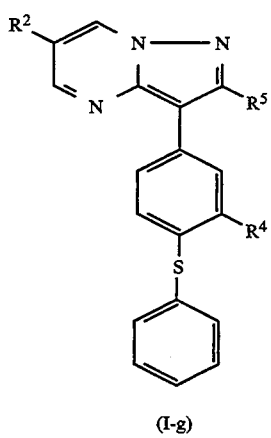

(where R³⁰ is a lower alkyl group, and R², R⁴ and R⁵ are same as defined above.)

This reaction is to obtain the compound expressed in Formula (I-g) by reaction of the compound in Formula (2) with acetal derivative of malondialdehyde expressed in Formula (26).

As the solvent, any solvent shown in Reaction scheme 1 may be used. The molar ratio of the compound (26) to the compound (2) is 1:1, preferably 1:1 to 20:1.

The reaction is carried out at 50° to 150° C., preferably 80° to 130° C., and is terminated in about 2 to 24 hours.

The compound expressed in Formula [I] easily forms a salt by reacting with a pharmaceutically available acid. Such acid may include, for example, inorganic acids such as hydrochloric acid, sulfuric acid, phosphoric acid and hydrobromic acid, and organic acids such as oxalic acid, maleic acid, fumaric acid, malic acid, tartaric acid, citric acid, benzoic acid, acetic acid, p-toluenesulfonic acid and ethansulfonic acid.

The compound [I] of the invention includes, naturally optical isomers, syn-isomers and anit-isomers. These isomers may be isolated by conventional splitting methods, such as the method of using optical resolving agent and the method of using enzyme.

The compound expressed in Formula [II] may be prepared in various methods, for example, those shown in the following Reaction scheme 21 to 26.

Reaction scheme 21

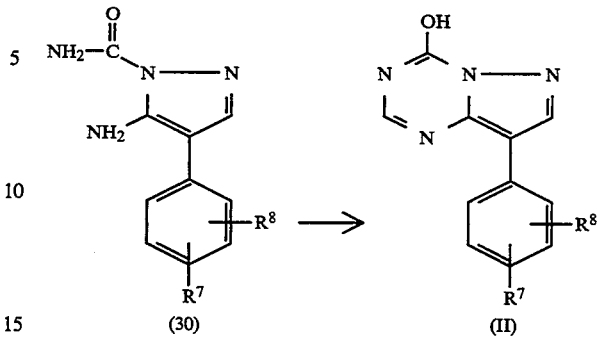

(where R⁷ and R⁸ are same as defined above.)

The compound of the invention expressed in Formula [II] is obtained by reacting the compound in Formula (30) with alkyl orthoformate such as methyl orthoformate and ethyl orthoformate. The reaction may be performed in a solvent which does not adversely affect the reaction, and the solvent is not always necessary because the alkyl orthoformate functions also as the solvent.

The reaction is performed by using alkyl orthoformate about 1 to 15 times mol of the compound of Formula (30), at 80 to 120° C. generally, and is terminated in about 20 minutes to 15 hours.

When using a solvents in this reaction, for example, nonprotic polar solvents such as N,N-dimethylformamide, dimethylsulfoxide and hexamethylphosphoric triamide, or their mixed solvent may be used. When using N,N-dimethylformamide as the solvent, this reaction is terminated in about 20 minutes to 2 hours.

Reaction scheme 22

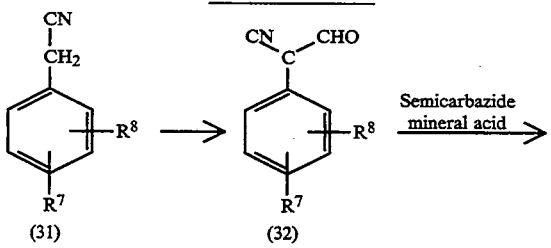

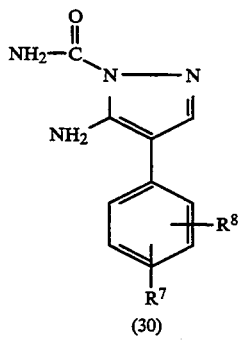

(where R⁷ and R⁸ are same as defined above.)

This reaction is to obtain the compound of Formula (32) by reaction of acetonitrile derivative in Formula (31) with formic ester, and prepare the compound of Formula (30) by reacting this compound (32) with semicarbazide mineral acid salt such as hydrochloride and sulfate of semicarbazide.

The solvent used in the reaction of the compound in Formula (31) and formic ester is the solvent not affecting the reaction, including aromatic hydrocarbons such as benzene, toluene and xylene, N,N-dimethylformamide, dimethylsulfoxide, and others. The molar ratio of the formic ester such as methyl formate and ethyl formate to the compound of Formula (31) is at least an equimolar amount, and preferably 1.05:1 to 1.25:1. The reaction is preferably carried out at 0° C. for 5 to 20 minutes, and then at room temperature for about 4 to 12 hours. In order to progress the reaction sufficiently, it is desired to perform in the presence of sodium alkoxide such as sodium methoxide at least an equimolar amount to the formic ester. After reaction is completed, water is added and the water layer is separated, and the pH is adjusted to 3 to 4 by using mineral acid such as hydrochloric acid, thereby obtaining the precipitated solid of Formula (32).

To the obtained compound of Formula (32), in ice-chilled state, semicarbazide mineral acid salt is dropped at least by an equimolar amount, preferably 1 to 1.2 times mol, and at room temperature the reaction is allowed to continue for about 4 to 15 hours to obtain the compound of Formula (30). The solvent used in this reaction may be any solvent not affecting the reaction, including, for example, lower aliphatic alcohol such as methanol and ethanol, and mixed solvent of such lower aliphatic alcohol with water. When using the mixed solvent, the mixing rate of the lower aliphatic alcohol and water is in a range of 1:1 to 10:1.

Reaction scheme 23

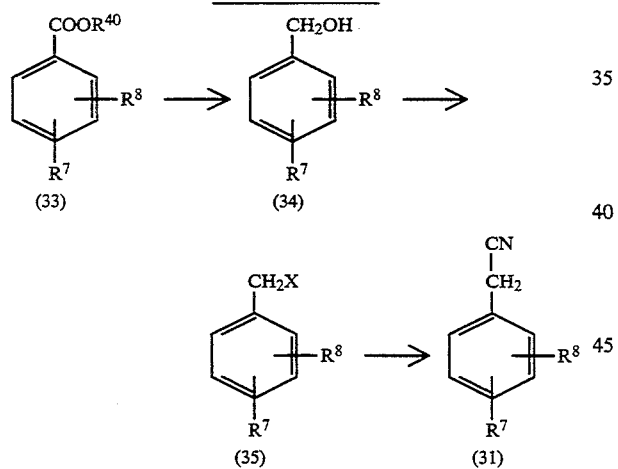

(where $R^{40}$ denotes a lower alkyl group, X indicates a halogen atom, and $R^7$ and $R^8$ are same as defined above.)

This reaction is to obtain the compound expressed in Formula (34) by reducing the compound expressed in Formula (33) by using a alkali metal hydride reducing agent, obtain the compound expressed in Formula (35) by reacting of this compound of Formula (35) with a halogenating agent, and obtain the compound expressed in Formula (31) which is the starting material of Reaction scheme 22 by reaction of this compound with a cyan compound.

The reaction for obtaining the compound (34) from the compound (33) is performed in a proper solvent. Examples of such solvent include ethers such as diethylether, tetrahydrofuran, dioxane and diglyme, aliphatic hydrocarbons such as hexane and heptane, and aromatic hydrocarbons such as benzene and toluene.

The alkali metal hydride reducing agent used in the reaction may include, for example, aluminium lithium hydride, aluminium hydride, aluminium diisopropyl hydride, lithium borohydride, sodium borohydride-aluminum chloride, diborane. The molar ratio of the alkali metal hydride reducing agent to the compound of Formula (34) is at least 0.5:1, preferably about 0.6:1 to 1.2:1. This reaction is usually carried out at 0° to 100° C., or preferably 0° to 50° C., and is terminated in about 30 minutes to 10 hours.

The reaction is carried out in proper solvent or without solvent, to obtain the compound(35). Examples of the solvent used in the reaction include ethers such as diethylether, tetrahydrofuran and dioxane, halogenated hydrocarbons such as methylene chloride, chloroform and dichloroethane, and aromatic hydrocarbons such as benzene and toluene. The halogenating agent used in the reaction is, for example, thionyl halide such as thionyl chloride and thionyl bromide, hydrogen halide such as hydrogen chloride, hydrogen bromide and hydrogen iodide, and phosphorus trihalide such as phosphorus trichloride and phosphorus tribromide. The molar ratio of the halogenating agent to the compound (35) is at least an equimolar amount, preferably 1:1 to 1.3:1. This reaction is carried out at 0° to 100° C., preferably about 0° to 50° C., and is terminated in about 30 minutes to 5 hours.

The reaction to obtain the compound expressed in Formula (31) from the compound expressed in Formula (35) is carried out in a proper solvent. The solvent used in the reaction may include, for example, lower aliphatic alcohol such as methanol, ethanol and propanol, non-protic polar solvent such as N,N-dimethylformamide, dimethylsulfoxide and hexamethylphosphoric triamide, and mixed solvents of them with water. The cyanide compound used in the invention may include, for example, potassium cyanide, sodium cyanide, sliver cyanide, copper cyanide, and calcium cyanide. The molar ratio of cyan agent to the compound (35) is at least an equimolar amount, preferably 1:1 to 1.3:1. The reaction is carried out at room temperature to 150° C., preferably at room temperature to 100° C., and is terminated in about 1 to 5 hours.

Reaction scheme 24

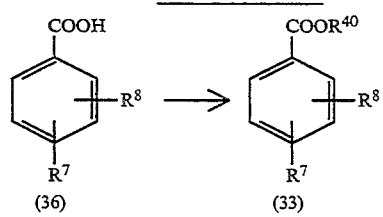

(where $R^7$, $R^8$ and $R^{40}$ are same as defined above.)

This reaction is to obtain the compound expressed in Formula (33) by reacting of the compound expressed in Formula (36) by ordinary esterifying method.

The esterification is performed by reacting of the compound of Formula (36), for example, in the presence of a catalyst, with an alcohol expressed in the formula:

$R^{40}$—OH (where $R^{40}$ is same as defined above), and the catalyst to be used may be any catalyst generally used in esterification. Practical examples thereof include inorganic acids such as hydrogen chloride, concentrated sulfuric acid, phosphoric acid, polyphosphoric acid, boron trifluoride and perchloric acid, organic acids such as trifluoroacetic acid, trichloromethanesulfonic acid, naphthalenesulfonic acid, p-toluensulfonic acid, benzenesulfonic acid and ethanesulfonic acid, acid anhydrides such as trichloromethanesulfonic anhydride and trifluoromethansulfonic anhydride, thionyl chloride, and others. Besides, a action exchange resin (acid type) may be also used. The esterification is performed in a proper solvent or without solvent. As the solvent, any solvent generally used in esterification may be used, including, for example, aromatic hydrocarbons such as benzene, toluene and xylene, halogenated hydrocarbons such as dichloromethane, dichloroethane and chloroform, and ethers such as diethylether, tetrahydrofuran and dioxane. The molar ratio of the acid to the compound (36) is 1:1 to 100:1, preferably 10:1 to 30:1. The reaction temperature is −20° to 200° C., preferably 0° to 150° C.

The compound of Formula (33) may be also obtained by a method of reaction of an alkali metal salt (for example, sodium salt, potassium salt) of the compound of Formula (34) with a halide compound expressed in the formula:

$R^{40}-X$ (where $R^{40}$ and X are same as defined above), a method of reaction of the compound of Formula (36) with diazoalkane such as diazomethane, diazoethane and diazopropane, or a method of reaction of the compound of Formula (36), after being transformed into a reactive derivative in its carboxy group, with an alcohol expressed in the formula:

$R^{40}-OH$ (where $R^{40}$ is same as defined above). These esterifications may be performed according to the conventional procedures.

Reaction scheme 25

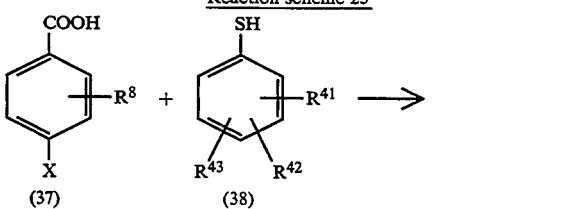

(37) (38)

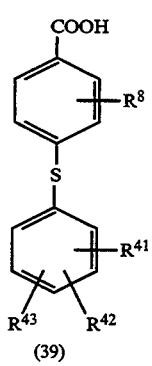

(39)

(where $R^8$ and X are same as defined above, $R^{41}$, $R^{42}$, $R^{43}$ are same or different hydrogen atom, lower alkyl group, lower alkoxy group or halogen atom.)

This reaction is to obtain the compound expressed in Formula (39) by reacting of the benzoic acid derivative of Formula (37) with phenylthio derivative of Formula (38). The reaction is performed in the presence of a base such as sodium hydroxide in a proper solvent. The available solvent includes methanol, ethanol and other lower alcohols.

The rate of the compound of Formula (37) is at least an equimolar amount, preferably in a slight excess. The base should be used at least twice the molar amount of the compound of Formula (37) or slightly in excess preferably in order to form salts of the compound (37) and the compound (38).

The reaction is usually performed at room temperature to 180° C., and is terminated in about 30 minutes to 24 hours.

Reaction scheme 26

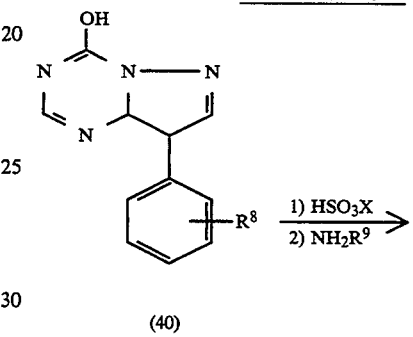

(40)

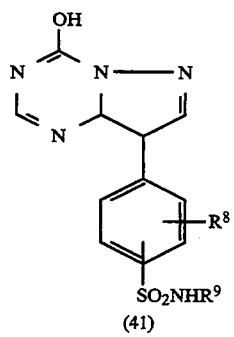

(41)

where $R^8$, $R^9$ and X are same as defined above.)

This reaction is to obtain the compound expressed in Formula (41) by reacting the halogenosulfonic acid compound with the compound expressed in Formula (40) to introduce the sulfonic acid group, and then treating to the ordinary amide forming reaction.

The halogensulfonic acid used in the reaction may include chlorosulfonic acid and bromosulfonic acid.

In the reaction, for example, to the compound expressed in Formula (40), the halogenosulfonic acid is used about 20 to 25 times molar amounts to react, at about 80° C., for 1 to 3 hours, the halogenosulfonic acid is introduced on the phenyl ring.

Of the compounds expressed in Formula [II], the compounds possessing a basic group may easily form salts by acting with a pharmaceutically available acid, or the compounds possessing an acidic group, with a pharmaceutically available basic compound. Examples of the acid may include inorganic acids and organic acids shown in the compound of Formula [I]. The basic compounds may be, for example, metal hydroxides such as sodium hydroxide, potassium hydroxide and calcium hydroxide, alkali metal carbonates or bicarbonate such as sodium carbonate, sodium hydrogencarbonate and potassium hydrogencarbonate, and the like.

The compounds expressed in Formula [II] naturally contain optical isomers. These isomers may be separated by the customary resolving methods as mentioned above.

The compound [I] or [II] of the invention is generally used in an ordinary pharmaceutical form. The dosage form is prepared by using general fillers, thickeners, binders, humidifiers, disintegrators, surfactants, lubricants, diluents, or vehicles. As pharmaceutical preparations, various forms may be selected depending on the therapeutic purposes, and typical examples include tablets, pills, powders, liquids, suspensions, emulsions, granules, capsules, suppositories, injections (liquid, suspension, etc.), lotion, cream, ointment and other external applications. When forming into tablets, any conventionally used carriers may be used, including, for example, vehicles such as lactose, sucrose, sodium chloride, glucose, urea, starch, calcium carbonate, kaolin, crystal cellulose and silici acid; binders such as water, ethanol, propanol, simple syrup, glucose solution, starch solution, gelatin solution, caboxymethylcellulose, shellac, methylcellulose, potassium phosphate and polyvinyl pyrrolidone; disinfectants such as dry starch, sodium aliginate, agar powder, laminaran powder, sodium hydrogencarbonate, calcium carbonate, polyoxyethylenesorbitan fatty acid ester, sodium lauryl sulfate, monoglyceride stearate, starch and lactose; disintegration inhibitors such as sucrose, stearin, cocoa butter and hydrogenated oil; absorption promoters such as quaternary ammonium base and sodium lauryl sulfate; moisturizers such as glycerin and starch, adsorbents such as starch, lactose, kaolin, bentonite and colloidal silic acid; and lubricants such as refined talc, stearate, boric acid powder and polyethyleneglycol. The tablets may be presented in ordinary forms of coated tablets as required, such as sugar coated tablet, gelatine encapsulated tablet, enteric coated tablet, film coated tablet, double tablet, and multilayer tablet.

When forming into pills, any conventionally used carriers may be used, including, for example, vehicles such as glucose, lactose, starch, cacao fat, hard vegetable oil, kaolin and talc; binders such as powdered gum arabic, powdered tragacanth, gelatin and ethanol; and disintegrators such as laminaran and agar. When forming into suppositores, any conventionally used carriers may be used, including, for example, polyethylene glycol, cacao fat, higher alcohol, higher alcohol esters, gelatin and semisynthetic glyceride. When forming into injections, the liquids, emulsions and suspensions should be sterilized, and should be isotonic with the blood, and to form into such forms as liquids, emulsions or suspensions, all diluents customarily used in the field may be used, including, for example, water, ethyl alcohol, propylene glycol, ethoxy isostearyl alcohol, polyoxy isostearyl alcohol, and polyoxyethylene sorbitan fatty acid ester. In this case, salt, glucose or glycerin enough to adjust the isotonic solution may be contained in the pharmaceutical preparations, and ordinary dissolution aids, buffers, and analgesics may be contained in the therapeutic drugs, together with, if necessary, coloring matter, preservative, perfume, flavor, sweetener or other medicines. To form in paste, cream or gel form, white vaseline, paraffin, glycerin, cellulose derivative, polyethylene glycol, silicon, bentonite or others may be used as the diluent.

The content of the pyrimidine derivative [I] of the invention or its salt to be contained in the pharmaceutical preparation is not particularly limited but may be selected in a wide range, but is generally in a range of 1 to 70% by weight of the whole composition. The content of the compound expressed in Formula [II] in the pharmaceutical preparation may be also in a range of 1 to 70% by weight of the whole composition.

The method of administration of the pharmaceutical preparations according to the invention is not particularly limited, and they may be administered in proper methods depending on the dosage form, age, sex or other conditions of patients, degree of symptoms, and others. For example, tablets, pills, liquids, suspensions, emulsions, granules and capsules are administered orally.

Injections are intravenously administered either alone or in a mixture with ordinary replenisher such as glucose and amino acid. Furthermore, as required, they are administered alone intramuscularly, intradermally, subcutaneously or intraperitoneally. Suppositories are rectally administered. The lotion, cream ointment and other external applications are topically applied.

The dose of the pharmaceutical preparations is properly selected depending on the route of administration, age, sex and other conditions of patients, degree of symptoms and others, and usually the daily dose of the compound of the invention per 1 kg of body weight is 1 to 100 mg, and preferably 5 to 20 mg, which may be divided in two to four portions a day.

Industrial Applicability

The pyrimidine derivative of the invention expressed in Formula [I] and its pharmaceutically available salt possess the activity to inhibit the expression of actions of androgen and are hence available preferably for treatment of benign prostatic hypertrophy, prostatic carcinoma, female hairiness, male baldness or pimple induced by promotion of androgen actions as androgen inhibitors.

The androgen inhibitor of the invention containing the compound expressed in Formula [II] also possesses the activity for inhibiting the expression of actions of androgen, and is hence available, same as the compound of Formula [I], preferably for treatment of benign prostatic hypertrophy, prostatic carcinoma, female hairiness, male baldness or pimple.

EXAMPLES

The invention is further described below while referring to some of the embodiments thereof together with reference examples.

Reference Example 1

3-Amino-4-(4-phenylthiophenyl)pyrazole

To a stirred suspension of 2.79 g of sodium methoxide in 100 ml of toluene at 0° C., was added a mixture of 8.97 g of 4-phenylthiophenylacetonitrile, 3.83 g of ethyl formate and 50 ml of toluene. Ice-cooling was stopped in 20 minutes, and further 2 hours later, iced water was added, and the water layer was separated.

The organic layer was washed twice in 100 ml each of aqueous solution of 0.5N sodium hydroxide. The water layer and washing solution were combined, and the pH was adjusted to 3 to 4 with concentrated hydrochloric acid, and the solution was stirred in ice-cooling. One hour later, the precipitate was filtered off, washed in water, and α-formyl-4-phenylthiophenylacetonitrile was obtained.

The obtained α-formyl-4-phenylthiophenylacetonitrile was, without being dried, added to the mixture of 50 ml of methanol and 10 ml of water, together with 4.43 g of semicarbazide hydrochloride, and the mixture was stirred for 10 minutes in ice-cooling. Stopping ice-cooling and letting stand for 19 hours, the solution was stirred at room temperature for 1 hour while keeping the pH at 9 to 10 by using aqueous solution of 5N sodium hydroxide. At this time, the temperature of the reaction solution was kept under 25° C. Adding 200 ml of water to the reaction solution, the mixture was stirred for 30 minutes in ice-cooling, and the precipitate was filtered. The obtained precipitate was added to 15 ml of aqueous solution of 5N sodium hydroxide and 150 ml of methanol, and the mixture was heated and refluxed for 25 minutes. Stopping heating, 300 ml of water was added, and the mixture was stirred for 30 minutes in ice-cooling, and the precipitate was washed in water and dried, and 8.53 g of the title compound was obtained.

mp: 120°~121° C.

NMR (DMSO-$d_6$) δ: 7.74 (s, 1H), 7.2~7.6 (m, 10H), 6.69 (bs, 2H)

Reference Example 2

α-Acetyl-4-phenylthiophenylacetonitrile

To a stirred suspension of 144 mg of 60% sodium hydride, in 10 ml of tetrahydrofuran at 0° C. under nitrogen atmosphere was added a mixture of 396 mg of ethyl acetate, 675 mg of 4-phenylthiophenylacetonitrile and 5 ml of tetrahydrofuran. Thirty minutes later, the ice bath was removed. Seventeen hours later, the tetrahydrofuran was distilled off in vacuo, and 10 ml of 2N hydrochloric acid and 20 ml of dichloromethane were added and separated, and the water layer was further extracted twice in 20 ml of dichloromethane. The organic layer and extract were combined, and dried by anhydrous magnesium sulfate, and concentrated in vacuo, and the residue was isolated and refined by silica gel chromatography (the eluent was a mixed solvent of hexane:ethyl acetate at a (v/v) rate of 4:1), and 587 mg of the title compound was obtained.

NMR (CDCl$_3$) δ: 7.26~7.38 (m, 9H), 4.63 (s,1H), 2.25 (s, 3H)

Reference Example 3

α-Fluoroacetyl-4-phenylthiophenylacetonitrile

The title compound was obtained in the same procedure as in Reference Example 2.

NMR (CDCl$_3$) δ: 7.23~7.45 (m, 9H), 5.36 (d, J=46.2 Hz, 2H), 4.63 (s, 1H)

Reference Example 4

α-Trifluoroacetyl-4-phenylthiophenylacetonitrile

The title compound was obtained in the same procedure as in Reference Example 2.

NMR (CDCl$_3$) δ: 7.20~7.35 (m, 9H), 4.16 (s, 1H)

Reference Example 5

3-Amino-5-methyl-4-(4-phenylthiophenyl)pyrazole

A mixture of 520 mg of α-acetyl-4-phenylthiophenylacetonitrile, 217 mg of semicarbazide hydrochloride, 15 ml of methanol and 3 ml of water was stirred at 0° C. for 10 minutes. Removing the ice bath, 40 hours later, the mixture was stirred at room temperature for 1 hour while keeping the pH at 9 to 10 by using aqueous solution of 2N sodium hydroxide. Adding 50 ml of water, the mixture was stirred for 30 minutes in ice-cooling, and the precipitate was filtered. It was directly added to the mixed solution of 5 ml of aqueous solution of 2N sodium hydroxide and 50 ml of methanol, and the mixture was stirred for 4 hours at room temperature, and then 80 ml of water was added, and the mixture was stirred for 30 minutes in ice-cooling, then the precipitate was filtered, Washed in water and dried, thereby obtaining 500 mg of the title compound.

NMR (CDCl$_3$) δ: 7.23~7.44 (m, 10H), 5.01 (bs, 2H), 2.27 (s, 3H)

Reference Example 6

3-Amino-5-methoxymethyl-4-(4-phenylthiophenyl)-pyrazole

Using the compound obtained in Reference Example 3, the title compound was obtained in the same procedure as in Reference Example 5.

NMR (CDCl$_3$) δ: 7.26~7.48 (m, 10H), 5.76 (bs, 2H), 4.46 (s, 2H), 3.36 (s, 3H)

Reference Example 7

3-Amino-4-(4-phenylthiophenyl)-5-trifluoromethyl pyrazole

A mixture of 410 mg of a-trifluoroacetyl-4-phenylthiophenylacetonitrile, 77 mg of hydrazine hydrate, 1 ml of acetic acid and 10 ml of benzene was heated and refluxed while dehydrating azeotropically. One hour later, by cooling, 15 ml of 6N hydrochloric acid was added to distribute into organic layer and water layer, and the water layer was further extracted twice in 20 ml of ethyl acetate, and was combined with the organic layer, and the combined organic layer was dried with anhydrous magnesium sulfate, and concentrated in vacuo, thereby obtaining 400 mg of the title compound as crude product. This product was used for the next step without further purification.

Example 1

6-Ethoxycarbonyl-7-hydroxy-3-(4-phenylthiophenyl)-pyrazolo[1,5-a]pyrimidine

A mixture of 2.97 g of 3-amino-4-(4-phenylthiophenyl)pyrazole obtained in Reference Example 1, 2.16 g of ethoxymethylenemalonic diethylester, and 20 ml of acetic acid was stirred for 2 hours while heating at 90° to 110° C. in a heating bath, and 0.21 g of ethoxymethylenemalonic diethylester was added, and the heating bath was removed 10 minutes later to allow to cool. The precipitate was filtered, washed in methanol and dried, and 1.69 g of the title compound was obtained.

mp: 251°~252.5° C.

NMR (DMSO-$d_6$) δ: 8.37 (s, 1H), 8.26 (s, 1H), 7.63 (d, J=8. 13 Hz, 2H), 7.42 (d, J=8.13 Hz, 2H), 7.38 (s, 5H), 4.27 (q, J=7.03 Hz, 2H), 1.31 (t, J=7.03 Hz 3H)

Example 2

6-Ethoxycarbonyl-5-hydorxy-3-(4-phenylthiophenyl)-pyrazolo[1,5-a]pyrimidine

Using 8.53 g of 3-amino-4-(4-phenylthiophenyl)pyrazole, the reaction was performed same as in Example 1, and the precipitate was washed in ethanol. The obtained filtrate and ethanol washing solution were let stand at room temperature for 20 hours, the precipitate was filtered, and washed in ethanol and dried, thereby obtaining 0.45 g of the title compound.

mp: 206°~207.5° C.

NMR (DMSO-d₆) δ: 9.07 (s, 1H), 8.37 (s, 1H), 7.70 (d, J=8.57 Hz, 2H), 7.36 (d, J=8.13 Hz, 2H), 7.34 (s, 5H), 4.27 (q, J=7.03 Hz, 2H), 1.31 (t, J=7.03 Hz 3H)

Example 3

7-Hydroxy-3-(4-phenylthiophenyl)pyrazolo[1,5-a]pyrimidine

A mixture of 3.91 g of 6-ethoxycarbonyl-7-hydroxy-3-(4-phenylthiophenyl)-pyrazolo[1,5-a]pyrimidine obtained in Example 1 and 30 ml of 85% phosphoric acid was heated in a heating bath to 170° C., and stirred for 30 minutes, and the mixture gradually developed foams, and the foams were about to cease, the reaction solution turned to a dark red color. Stopping the heating bath, 200 ml of water was added, and after letting stand for 30 minutes while ice-cooling, the precipitate was filtered, washed in water and dried, and 2.55 g of the title compound was obtained.

mp: 232°-236° C.
(Refining by silica gel column)
NMR (DMSO-₆) δ: 8.22 (s, 1H), 7.81 (d, J=7.4 Hz, 1H), 7. 61 (d, J=8. 57 HZ, 2H), 7.40 (d, J=8.57 Hz, 2H), 7. 29~7. 41 (m, 5H), 5. 79 (d, J=7.47 Hz; 1H)

Example 4

5-Hydroxy-3-(4-phenylthiophenyl)pyrazolo[1,5-a]pyrimidine

In the same manner as in Example 3 except that 0.39 g of 6-ethoxycarbonyl-5-hydroxy-3-(4-phenylthiophenyl)-pyrazolo[1,5-a]pyrimidine obtained in Example 2 and 5 ml of 85% phosphoric acid were used, 0.16 g of the title compound was obtained.

mp: 214°-216° C.
(Purified by silica gel column chromatography)
NMR (DMSO-d₆) δ: 8.57 (d, J=7.92 Hz, 1H), 8.20 (s, 1H), 7.72 (d, J=8.13 Hz, 2H), 7.36 (d, 2H, J=8.13 Hz, 2H), 7.27~7.42 (m, 5H), 6.12 (d, J=7.91 Hz, 1H)

Example 5

7-Hydroxy-5,methyl-3-(4-phenylthiophenyl)-pyrazolo[1,5-a]pyrimidine

A mixture of 0.34 g of 3-amino-4-(4-phenylthiophenyl)pyrarzole; 0,165 g of ethyl acetoacetate and 2 ml of acetic acid was heated at 100° to 110° C. and stirred. Two hours later, the reaction mixture was concentrated in vacuo, and 20 ml of ethanol was added to the residue, which was concentrated in vacuo. To the residue obtained by repeating the same operation, 20 ml of etyl acetate was added to solidify the mixture. The solid matter was filter and washed in ethyl acetate and dried, and 0.31 g of the title compound was obtained.

mp: 233°~234° C.
NMR (DMSO-d₆) δ: 8.09 (s, 1H), 7.59 (d, J=8.57 Hz, 2H), 7.39 (d, J=8.13 Hz, 2H), 7.36 (s, 5H), 5.65 (s, 1H), 2.50(s, 3H)

Example 6

7-Hydroxy-5-ethyl-3-(4-phenylthiophenyl)-pyrazolo[1,5-a]pyrimidine

The title compound was obtained according to the procedure of Example 5.

mp: 222°~224° C.
NMR (CD₃ OD-CDCl₃) δ: 7.90 (s, 1H), 7.30~7.40 (m, 9H), 5.71 (s, 1H), 2.70 (q, J=7.42 Hz, 2H), 1.32 (t, J=7.42 Hz, 3H)

Example 7

7-Hydroxy-5-isopropyl-3-(4-phenylthiophenyl)-pyrazolo[1,5-a]pyrimidine

The title compound was obtained according to the procedure of Example 5.

mp: 260°~261° C. (decomposed)
NMR (CD₃ OD-CDCl₃) δ: 7.91 (s, 1H), 7.30~7.37 (m, 9H), 5.75 (s, 1H), 2.95 (Heptet, J=6.93 Hz, 1H), 1.33 (d, J=6.93 Hz, 6H)

Example 8

7-Hydroxy-5-cyclopropyl-3-(4-phenylthiophenyl)-pyrazolo[1,5-a]pyrimidine

The title compound was obtained according to the procedure of Example 5.

mp: 238°~241° C. (decomposed)
NMR (CD₃ OD-CDCl₃) δ: 7.92 (s, 1H), 7.32~7.41 (m, 9H), 5.37 (s, 1H), 1.91~2.01 (m, 1H), 1.11~1.19 (m, 2H), 0.91~0.98 (m, 2H)

Example 9

7-Hydroxy-5-chloromethyl-3-(4-phenylthiophenyl)-pyrazolo[1,5-a]pyrimidine

The title compound was obtained according to the procedure of Example 5.

mp: 190°~191° C.
NMR (CD₃ OD-CDCl₃) δ: 7.97 (s, 1H), 7.28~7.43 (m, 9H), 5.95 (s, 1H), 4.54 (s, 2H)

Example 10

7-Hydroxy-5-phenyl-3-(4-phenylthiophenyl)-pyrazolo[1,5-a]pyrimidine

The title compound was obtained according to the procedure of Example 5.

mp: 253°~255° C. (decomposed)
NMR (CD₃ OD-CDCl₃) δ: 8.02 (s, 1H), 7.69 (d, J=8.56 Hz, 2H), 7.28~7.57 (m, 12H) , 6.09 (s, 1H)

Example 11

5H-6,7-Dihydro-8-hydroxy-3-(4-phenylthiophenyl)cyclopenta[d]pyrazolo[1,5-a]pyrimidine The title compound was obtained according to the procedure of Example 5.

mp: 274° C. (decomposed)
NMR (CD₃ OD-CDCl₃) δ: 7.92 (s, 1H), 7.25~7.43 (m, 9H), 2.96~3.02 (m, 2H), 2.81~2.87 (m, 2H), 2.14~2.20 (m, 2H)

Example 12

9-Hydroxy-3-(4-phenylthiophenyl)-5,6,7,8-tetrahydropyrazolo[5,1-b]quinazoline

The title compound was obtained according to the procedure of Example 5.

mp: 271°~272° C.
NMR (DMSO-d₆) δ: 8.11 (s, 1H), 7.59 (d, J=8.2 Hz, 2H), 7.3~7.5 (m, 7H), 2.7~2.8 (m, 2H), 2.4~2.5 (m, 2H), 1.6~1.8 (m, 4H)

Example 13

7-Hydroxy-5-trifluoromethyl-3-(4-phenylthiophenyl)-pyrazolo[1,5-a]pyrimidine

In an 8 ml acetic acid solution of 1.07 g of 3-amino-4-(4phenylthiophenyl)pyrazole, 0.6 ml of ethyl 4,4,4-trifluoroacetoacetate was added and stirred for 2 hours at 100° C. After allowing to cool, ether was added, and the precipitate was filtered and dried, and the title compound was obtained (200 mg, 13%).

mp: 270°~273° C.

NMR (DMSO-d$_6$) δ: 8.93 (s, 1H), 8.73 (d, J=8.35 Hz, 2H), 7.42 (d, J=8.35 Hz, 2H), 7.34 (s, 5H), 6.32 (s, 1H)

Example 14

7-Hydroxy-6-ethoxycarbonyl-3-(3-methoxy-4-phenylthiophenyl)pyrazolo[1,5-a]pyrimidine The title compound was obtained according to the procedure of Example 1.

mp: 256°~258° C.

NMR (DMSO-d$_6$) δ: 8.36 (s, 1H), 8.30 (s, 1H), 7.13~7.39 (m, 8H), 4.26 (q, J=7.04 Hz, 2H), 3.91 (s, 3H), 1.29 (t, J=7.04 Hz, 3H)

Example 15

7-Hydroxy-3-(3-methoxy-4-penylthiophenyl)-pyrazolo[1,5-a]pyrimidine

The title compound was obtained according to the procedure of Example 3.

mp: 220°~260° C.

NMR (DMSO-d$_6$) δ: 8.25 (s, 1H), 7.80 (d, J=6.81 Hz, 1H), 7.03~7.44 (m, 8H), 5.69 (d, J=6.81 Hz, 1H), 3.88 (s, 3H)

Example 16

7-Hydroxy-6-ethoxycarbonyl-2-methyl-3-(4-phenylthiopheny)pyrazolo[1,5-a]pyrimidine The title compound was obtained according to the procedure of Example 1.

NMR (CDCl$_3$) δ: 8.28 (s, 1H), 7.42 (bs, 9H), 4.24 (q, J=7.03 Hz, 2H), 2.33 (s, 3H), 1.32 (t, J=7.04 Hz, 3H)

Example 17

7-Hydroxy-6-ethoxycarbonyl-2-methoxymethyl-3-(4-phenylthiophenyl)pyrazolo[1,5-a]pyrimidine The title compound was obtained according to the procedure of Example 1.

NMR (DMSO-d$_6$) δ: 8.32 (s, 1H), 7.27~7.63 (m, 9H), 4.47 (s, 2H), 4.25 (q, J=7.03 Hz, 2H), 3.26 (s, 3H), 1.28 (t, J=7.03 Hz, 3H)

Example 18

7-Hydroxy-2-methyl-3-(4-phenylthiophenyl)-pyrazolo[1,5-a]pyrimidine

The title compound was obtained according to the procedure of Example 3.

mp: 218°~235° C.

NMR (DMS O-d$_6$) δ: 7.69 (d, J=7.26 Hz, 1H), 7.36~7.47 (m, 9H), 5.71 (d, J=7.25 Hz, 1H), 2.32 (s, 3H)

Example 19

7-Hydroxy-2-methoxymethyl-3-(4-phenylthiophenyl)-pyrazolo[1,5-a]pyrimidine

The title compound was obtained according to the procedure of Example 3.

mp: 164°–167° C.

Example 20

7-Hydroxy-6-ethoxycarbonyl-3-(4-phenylthiophenyl)-2-trifluoromethylpyrazolo[1,5-a]pyrimidine The title compound was obtained according to the procedure of Example 1.

NMR (DMSO-d$_6$) δ: 8.40 (s, 1H), 7.31~7.45 (m, 9H), 4.26 (q, J=7.03 Hz, 2H), 1.29 (t, J=7.04 Hz, 3H)

Example 21

7-Hydroxy-6-methoxy-3-(4-phenylthiophenyl)-pyrazolo[1,5-a]pyrimidine

To a tetrahydrofuran suspension of 480 mg of 60% sodium hydride, 2 ml of ethyl formate and 1.0 g of ethyl methoxyacetate were added under nitrogen atmosphere, and the mixture was stirred for 16 hours at room temperature. In succession, adding 1.0 g of 3-amino-4-(4-phenylthiophenyl)pyrazole, the solution was stirred for 4 hours in reflux. After allowing to cool, water was added and the solution was neutralized with 10% hydrochloric acid. Removing water, ethyl acetate was added, and insoluble matter was filtered. The filtrate was washed in ethyl acetate and ether and dried, and the title compound was obtained (100 mg, 8%).

mp: 267°~272° C.

NMR (DMSO-d$_6$) δ: 8.24 (s, 1H), 7.70 (s, 1H), 7.63 (d, J=8.57 Hz, 2H), 7.40 (d, J=8.57 Hz, 2H), 7.35 (s, 5H), 3.78(s, 3H)

Example 22

7-Hydroxy-6-fluoro-3-(4-phenylthiophenyl)pyrazo1,5-a]pyrimidine

The title compound was obtained according to the procedure of Example 21.

mp: 278°~281° C.

NMR (DMSO-d$_6$) δ: 8.32 (d, J=5.0 Hz, 1H), 8.30 (s, 1H), 7.63 (d, J=8.35 Hz, 2H), 7.40 (d, J=8.35 Hz, 2H), 7.36 (s, 5H)

Example 23

7-Hydroxy-6-phenyl-3-(4-phenylthiophenyl)-pyrazolo[1,5-a]pyrimidine

To tetrahydrofuran suspension of 480 mg of 60% sodium hydride, 2 ml of ethyl formate and 1.64 g of ethyl phenylacetate were added in nitrogen atmosphere, and stirred for 19 hours at room temperature. Adding 1.0 g of 3-amino-4-(4-phenylthiophenyl)-pyrazole, the mixture was stirred for 4 hours under reflux. After allowing to cool, water and 10% hydrochloric acid was added. The solution obtained was extracted with ethyl acetate. After washing with water, the organic layer was dried over anhydrous sodium sulfate, and the solvent is distilled off. The residue was dissolved in 5 ml of acetic acid, and the mixture was heated and stirred for 2 to 20 hours at 120° C. After allowing to cool, ethyl acetate was added, and the precipitate was filtered. The filtrate was washed with ethyl acetate and ether and dried, and the title compound was obtained (270 mg, 18%).

mp: >300° C.

NMR (DMSO-d$_6$) δ: 8.28 (s, 1H), 7.97 (s, 1H), 7.60~7.80 (m, 4H), 7.20~7.57 (m, 10H)

Example 24

7-Hydroxy-6-methyl-3-(4-phenylthiophenyl)-pyrazolo[1,5-a]pyrimidine

The title compound was obtained according to the procedure of Example 23.

mp: 270°~275° C.

NMR (DMSO-d$_6$) δ: 8.22 (s, 1H), 7.75 (s, 1H), 7.51 (d, J=8.35 Hz, 2H), 7.40 (d, J=8.35 Hz, 2H), 7.35 (s, 5H), 2.04(s, 3H)

Example 25

7-Hydroxy-6-ethyl -3-(4-phenylthiophenyl)-pyrazolo[1,5-a]pyrimidine

The title compound was obtained according to the procedure of Example 23.

mp: 268°~272° C.

NMR (DMSO-d$_6$) δ: 8.18 (s, 1H), 7.80 (d, J=8.35 Hz, 2H), 7.72 (s, 1H), 7.37 (d, J=8.35 Hz, 2H), 7.31 (s, 5H), 2.50 (q, J=7.10 Hz, 2H), 1.14 (t, J=7.10 Hz, 3H)

Example 26

7-Hydroxy-6-isopropyl-3-(4-phenylthiophenyl)-pyrazolo[1,5-a]pyrimidine

The title compound was obtained according to the procedure of Example 23.

mp: 238°~242° C.

NMR (DMSO-d$_6$) δ: 8.22 (s, 1H), 7.88 (s, 1H), 7.66 (d, J=8.57 Hz, 2H), 7.39 (d, J=8.57 Hz, 2H), 7.36 (s, 5H), 2.80~3.30 (m, 1H), 1.21 (d, J=6.82 Hz, 6H

Example 27

7-Hydroxy-6-cyclohexyl-3-(4-phenylthiophenyl)-pyrazolo[1,5-a]pyrimidine

The title compound was obtained according to the procedure of Example 23.

mp: 213°~216° C.

NMR (DMSO-d$_6$) δ: 8.19 (s, 1H), 7.65 (d, J=8.07 Hz, 2H), 7.52 (s, 1H), 7.39 (d, J=8.10 Hz, 2H), 7.34 (s, 5H), 1.00~2.00 (m, 11H)

Example 28

7-Hydroxy-6-phenethyl-3-(4-phenylthiophenyl)-pyrazolo[1,5-a]pyrimidine

The title compound was obtained according to the procedure of Example 23.

mp: 278°~285° C.

NMR (DMSO-d$_6$) δ: 8.21 (s, 1H), 7.60 (d, J=8.36 Hz, 2H), 7.59 (s, 1H), 7.39 (d, J=8.36 Hz, 2H), 7.35 (s, 5H), 7.24 (s, 5H), 2.60~3.00 (m, 4H)

Example 29

7-Hydroxy-6-benzyl-3-(4-phenylthiophenyl)-prazolo[1,5-a]pyrimidine

The title compound was obtained according to the procedure of Example 23.

mp: 254°~256° C.

NMR (DMSO-d$_6$) δ: 8.21 (s, 1H), 7.79 (s, 1H), 7.61 (d, J=8.35 Hz, 2H), 7.39 (d, J=8.35 Hz, 2H), 7.36 (s, 5H), 7.20~7.40 (m, 5H), 3.81 (s, 2H)

Example 30

7-Hydroxy-6-(2-methoxyphenylmethyl)-3-(4-phenylthiophenyl)pyrazolo[1,5-a]pyrimidine The title compound was obtained according to the procedure of Example 23.

mp: 219°~221° C.

NMR (DMSO-d$_6$) δ: 8.24 (s, 1H), 7.70 (d, J=8.35 Hz, 2H), 7.57 (s, 1H), 7.37 (d, J=8.35 Hz, 2H), 7.35 (s, 5H), 6.85~7.32 (m, 4H), 3.81 (s, 3H), 3.75 (s, 2H)

Example 31

7-Hydroxy-6-(3-methoxyphenylmethyl)-3-(4-phenylthiophenyl)pyrazolo[1,5-a]pyrimidine The title compound was obtained according to the procedure of Example 23.

mp: 240°~242° C.

NRN (DMSO-d$_6$) δ: 8.21 (s, 1H), 7.74 (s, 1H), 7.61 (d, J=8.57 Hz, 2H), 7.39 (d, J=8.57 Hz, 2H), 7.35 (s, 5H), 7.14 (d, J=7.91 Hz, 1H), 6.79~7.00 (m, 3H), 3.77 (s, 2H), 3.72 (s, 3H)

Example 32

7-Hydroxy-6-(4-methoxyphenylmethyl)-3-(4-phenylthiophenyl)pyrazolo[1,5-a]pyrimidine The title compound was obtained according to the procedure of Example 23.

mp: 271°~273° C.

NMR (DMSO-d$_6$) δ: 8.20 (s, 1H), 7.73 (s, 1H), 7.59 (d, J=8.14 Hz, 2H), 7.39 (d, J=8.14 Hz, 2H), 7.35 (s, 5H), 7.23 (d, J=8.35 Hz, 2H), 6.83 (d, J=8.35 Hz, 2H), 3.73 (s, 2H), 3.71 (s, 3H)

Example 33

7-Hydroxy-6-ethoxycarbonylmethyl-3-(4-phenylthiophenyl)pyrazolo[1,5-a]pyrimidine The title compound was obtained according to the procedure of Example 23.

mp: 240°~243° C.

NMR (DMSO-d$_6$) δ: 8.22 (s, 1H), 7.87 (s, 1H), 7.61 (d, J=8.13 Hz, 2H), 7.40 (d, J=8.13 Hz, 2H), 7.35 (s, 5H), 4.09 (d, J=7.25 Hz, 2H), 3.52 (s, 2H), 1.20 (t, J=7.25 Hz, 3H)

Example 34

7-Hydroxy-6-ethoxycarbonylmethyl-3-(4-phenylthiophenyl)pyrazolo[1,5-a]pyrimidine The title compound was obtained according to the procedure of Example 23.

mp: 212°~216° C.

NMR (DMSO-d$_6$) δ: 8.21 (s, 1H), 7.73 (d, J=5.49 Hz, 1H), 7.61 (d, J=8.35 Hz, 2H), 7.38 (d, J=8.35 Hz, 2H), 7.35 (s, 5H), 4.05 (q, J=7.03 Hz, 2H), 2.47~2.73(m, 4H), 1.16 (t, J=7.03 Hz, 3H)

Example 35

7-Hydroxy-6-bromo-3-(4-phenylthiophenyl)-pyrazolo[1,5a]pyrimidine

To a 2-ml solution of dimethylformamide of 320 mg of 7-hydroxy-3-(4-phenylthiophenyl)pyrazolo[1,5-a]pyrimidine, 200 mg of N-bromosuccinimide was added, and stirred for 3 hours at room temperature. Adding water, the precipitate was filtered, washed with water and ether, and dried, and the title compound was obtained (370 mg, 93%).

mp: >300° C.

NMR (DMSO-d$_6$) δ: 8.25 (s, 2H), 7.63 (d, J=8.35 Hz, 2H), 7.40 (d, J=8.35 Hz, 2H), 7.36 (s, 5H)

Example 36

7-Hydroxy-6-chloro-3-(4-phenylthiophenyl)-pyrazolo[1,5-a]pyrimidine

The title compound was obtained according to the procedure of Example 35.

mp: 180°~195° C. (decomposed)

NMR (DMSO-d$_6$) δ: 8.28 (s, 1H), 8.22 (s, 1H), 7.20~7.65 (m, 9H)

Example 37

7-hydroxy-6-chloro-5-methyl-3-(4-phenylthiophenyl)-pyrazolo[1,5-a]pyrimidine

The title compound was obtained according to the procedure of Example 5.

mp: 259°~261° C. (decomposed)

NMR (CD$_3$OD-CDCl$_3$) δ: 7.90 (s, 1H), 7.27~7.38 (m, 9H), 2.57 (s, 3H)

Example 38

7-Hydroxy-6-carboxy-3-(4-phenylthiophenyl)-pyrazolo[1,5-a]pyrimidine

A mixture of 10.30 g of 7-hydroxy-6-ethoxycarbonyl-3-(4-phenylthiophenyl)pyrazolo[1,5-a]pyrimidine, 6.59 g of sodium hydroxide, 300 ml of ethanol and 300 ml of water was heated and stirred for 2 hours. To the reaction mixture, 400 ml of water was added, and hydrochloric acid was also added while ice-cooling to adjust the pH to 1 to 2, and after stirring for 30 minutes, the precipitate was filtered, washed in water, and dried, thereby obtaining the title compound ( 9.42 g ).

NMR (DMSO-$d_6$) δ: 8.46 (s, 1H), 8.36 (s, 1H), 7.76 (d, J=8.35 Hz, 2H), 7.40 (d, J=8.35 Hz, 2H), 7.35 (s, 5H)

Example 39

7-Hydroxy-6-carboxyethyl-3-(4-phenylthiophenyl)-pyrazolo[1,5-a]pyrimidine

To methanol suspension of 200 mg of 7-hydroxy-6-ethoxycarbonylethyl-3-(4-phenylthiophenyl)-pyrazolo[1,5a-]pyrimidine, 2 ml of 2N sodium hydroxide was added, and the mixture was stirred for 3 days at room temperature. The reaction solution was turned acidic by adding 10% hydrochloric acid, and the precipitate was filtered, washed with water and dried, and the title compound was obtained (quantitatively).

mp 250°~253° C.

NMR (DMSO-$d_6$) δ: 8.21 (s, 1H), 7.72 (s, 1H), 7.61 (d, J=8.35 Hz, 2H), 7.39 (d, J=8.35 Hz, 2H), 7.35 (s, 5H), 3.27 (s, 2H), 2.4 6~2.70 (m, 4H)

Example 40

7-Hydroxy-6-carboxymethyl-3-(4-phenylthiophenyl)-pyrazolo[1,5-a]pyrimidine

The title compound was obtained according to the procedure of Example 39.

mp: 244~246° C.

NMR (DMSO-$d_6$) δ: 8.23 (s, 1H), 7.85 (s, 1H), 7.62 (d, J=8.57 Hz, 2H), 7.41 (d, J=8.57 Hz, 2H), 7.36 (s, 5H), 3.45 (s, 2H)

Example 41

7-Hydroxy-3-(3-methoxy-4-phenylthiophenyl)-pyrazolo[1,5-a]pyrimidine

To 340 mg of 7-hydroxy-6-ethoxycarbonyl-3-(3-methoxy-4-phenylthiophenyl)pyrazolo[1,5-a]pyrimidine, 15 ml of dioxane and 2 ml of aqueous solution of 2N sodium hydroxide were added, and heated and refluxed for 1 hour. The reaction mixture was concentrated in vacuo, and 30 ml of water was added to the residue, which was neutralized with acetic acid. The precipitate was filtered, washed with water and dried, and the title compound was obtained (260 mg)

mp: 234°~236° C.

NMR (DMSO-$d_6$) δ: 8.46 (s, 1H), 8.41 (s, 1H) , 7.17°~7.89 (m, 8H), 3.90 (s, 3H)

Example 42

7-Hydroxy-6-(N-phenylcarbamoyl)-3-(4-phenylthiophenyl)pyrazolo[1,5-a]pyrimidine

Dissolving 280 mg of 7-hydroxy-6-ethoxycarbonyl-3-(4-phenylthiophenyl)pyrazolo[1,5-a]pyrimidine in 3 ml of aniline, the mixture was stirred for 3 hours at 180° C. After allowing to cool, 10% hydrochloric acid was added, the precipitate was filtered, washed with water and dried, and the title compound was obtained (220 mg, 68%).

mp: >300° C.

NMR (DMSO-$d_6$) δ: 8.57 (s, 1H), 8.40 (s, 1H), 7.00~7.80 (m, 14H)

Example 43

6-Carbamoyl-7-hydroxy-3-(4-phenylthiophenyl)-pyrazolo1,5a-]pyrimidine

To 120 mg of 7-hydroxy-6-carboxy-3-(4-phenylthiophenyl)pyrazolo[1,5-a]pyrimidine, 0.5 ml of thionyl chloride was added while ice-cooling, and stirred for 1 hour. By concentrating in vacuo, 6-chloroformyl-7-hydrxy-3-(4-phenylthiophenyl)pyrazolo[1,5-a]pyrimidine was obtained. The obtained compound was stirred while ice-cooling, and was added to the mixed solution of 0.3 ml of 28% ammonia water and 2 ml of pyridine. After letting stand for 30 minutes, the reaction mixture was concentrated in vacuo, and the residue was washed in water and dried, and the title compound was obtained (97 mg).

mp 262°~273° C.

NMR (DMSO-d,) δ: 8.42 (s, 1H), 8.31 (s, 1H), 7.33~7.89 (m, 9H)

Example 44

6-Carbamoyl-7-hydroxy-3-(3-methoxy-4-phenylthiophenyl)pyrazolo[1,5-a]pyrimidine

The title compound was obtained according to the procedure of Example 43.

NMR (DMSO-$d_6$) δ: 8.47 (s, 1H), 8.37 (s, 1H), 7.00~7.38 (m, 8H), 3.91, (s, 3H)

Example 45

7-Hydroxy-3-(4-phenylthiophenyl)-6-(N-3,4,5-trichlorophenyl)carbamoylpyrazolo[1,5-a]pyrimidine The title compound was obtained according to the procedure of Example 43.

mp 272°~285° C.

NMR (DMSO-$d_6$) δ: 11.31 (s, 1H), 8.55 (s, 1H), 8.39 (s, 1H), 8.05 (s, 2H), 7.37~7.78 (m, 9H)

Example 46

7-Hydroxy-3-(4-phenylthiophenyl)-6-(N-t-butyl)carbamoylpyrazolo[1,5-a]pyrimidine The title compound was obtained according to the procedure of Example 43.

mp: 222°~250° C.

NMR (DMSO-$d_6$) δ: 9.41 (s, 1H), 8.54 (d, J=5.49 Hz, 1H), 8.34 (d, J=13.85 Hz, 1H), 7.26~8.21 (m, 9H), 1.15~1.38 (m, 9H)

Example 47

7-Hydroxy-6-cyano-3,(4-phenylthiophenyl)-pyrazolo[1,5-a]pyrimidine

Dissolving 36 mg of 7-hydroxy-6-carbamoyl-3-(4-phenylthiophenyl)pyrazolo[1,5-a]pyrimidine in dimethylformamide, and stirring in ice-cooling, 0.05 ml of thionyl chloride was added. The ice bath was removed 30 minutes later. Ice water was added 17 hours later, and the precipitate was filtered, washed with water, dried, and isolated and refined in preparative silica gel plate (using a developing solvent mixing chloroform: methanol:acetic acid at 80:25:2), and the title compound was obtained (13 mg).

mp: >300° C.

NMR (DMSO-$d_6$) δ: 8.55 (s, 1H), 8.34 (s, 1H), 7.36~7.73 (m, 9H)

Example 48

7-Hydroxy-3-(4-phenylthiophenyl)pyrazolo[1,5-a]pyrimidine

A mixture of 9.32 g of 7-hydroxy-6-carboxy-3-(4-phenylthiophenyl)pyrazolo[1,5-a]pyrimidine and 68 ml of aniline was heated and stirred at 80° C. for 1.5 hours to react. To the reaction mixture, 300 ml of water was added, and while ice-cooling, hydrochloric acid was added to adjust the pH to 1 to 2. Adding 100 ml of methanol, the mixture was stirred for 30 minutes while ice-cooling, and the precipitate was filtered, washed in cold water-methanol (3:1), and dried, and the title compound was obtained (8.17 g).

NMR (CDCl$_3$) δ: 8.22 (s, 1H), 7.80 (d, J=7.47 Hz, 1H), 7.60 (d, J=8.13 Hz, 2H), 7.40 (d, J=8.13 Hz, 2H), 7.36 (s, 5H), 5.79 (d, J=7.47 Hz, 1H)

Example 49

3-(4-phenylthiophenyl)pyrazolo[1,5-a]pyrimidine

A mixture of 0.26 g of 3-amino-4-(phenylthiophenyl)-pyrazole and 3 ml of malondialdehyde tetramethyl acetal was heated and stirred for 30 hours at 120° C. to react. After concentrating in vacuo, the residue was refined by silicagel column (chloroform), and the title compound was obtained (0.17 g).

mp: 72°~72.5° C.

NMR (CDCl$_3$) δ: 8.67 (dd, J=1.76 Hz, 7.04 Hz, 1H), 8.54 (dd, J=1.76 Hz, 4.17 Hz, 1H), 8.42 (s, 1H), 8.00 (d, J=8.57 Hz, 2H), 7.45 (d, J=8.57 Hz, 2H), 7.18~7.37 (m, 5H), 6.83 (dd, J=4.17 Hz, 7.03 Hz, 1H)

Example 50

7-Hydroxy-6-methyl-3-(4-phenylthiophenyl)-pyrazolo[1,5-a]pyrimidine

To a benzene suspension of 480 mg of 60% sodium hydride, 2 ml of ehtyl formate and 1.2 ml of ethyl propionate were added in nitrogen atmosphere, and stirred for 16 hours at room temperature. After distilling away the benzene in vacuo, 5 ml of acetic acid was added to the residue, and 1.0 g of 3-amino-4-(4-phenylthiophenyl)pyrazole was added, and the mixture was heated and stirred for 5 hours at 120° C. After allowing to cool, ethyl acetate was added, and the precipitate was filtered, washed in ethyl acetate and water, and dried, thereby obtaining the title compound (1.0 g, 81%).

The melting point and NMR of this compound were almost same as those of Example 24.

Example 51

7-Hydroxy-6-(4-methylphenyl)-3-(4-phenylthiophenyl)-pyrazolo[1,5-a]pyrimidine

The title compound was obtained according to the procedure of Example 50.

mp: >300° C.

NMR (DMSO-d$_6$) δ: 8.26 (s, 1H)-7.91 (s, 1H), 7.64 (d, J=8.1 Hz, 2H), 7.36~7.60 (m, 4H), 7.36 (s, 5H), 7.22 (d, J=8.1 Hz, 2H), 2.34 (s, 3H)

Example 52

7-Hydroxy-6-(4-methoxyphenyl)-3-(4-phenylthiophenyl)pyrazolo[1,5-a]pyrimidine

To a benzene suspension of 480 mg of 60% sodium hydride, 2 ml of ethyl formate and 2.0 g of ethyl 4-methoxyphenylacetate were added under nitrogen atmosphere, and stirred for 16 hours at room temperature. Adding 1.0 g of 3-amino-4-(4-phehylthiophenyl)-pyrazole, the mixture was stirred for 4 hours under reflux. After allowing to cool, water and 10% hydrochloric acid were added to neutralize, and the mixture was extracted with ethyl acetate, washed with water, and the organic layer was dried over anhydrous sodium sulfate, and the solvent was distilled off. The residue was dissolved in 5 ml of acetic acid, and was heated and stirred for 6 hours at 120° C. After allowing to cool, ethyl acetate was added, the precipitate was filtered, washed with ethyl acetate and ether, dried, and the title compound was obtained (400 mg, 25%).

mp: >300° C.

NMR (DMSO-d$_6$) δ: 8.27 (s, 1H), 7.89 (s, 1H), 7.65 (d, J=8.6 Hz, 2H), 7.60 (d, J=8.8 Hz, 2H), 7.44 (d, J=8.6 Hz, 2H), 7.87 (s, 5H), 6.99 (d, J=8.8 Hz, 2H), 3.79 (s, 3H)

Example 53

7-Hydroxy-6-(2-methoxyphenyl)-3-(4-phenylthiophenyl)pyrazolo[1,5-a]pyrimidine

The title compound was obtained according to the procedure of Example 52.

mp: >300° C.

NMR (DMSO-d$_6$) δ: 8.25 (s, 1H), 7.77 (s, 1H), 7.67 (d, J=8.4 Hz, 2H), 7.41 (d, J=8.4 Hz, 2H), 7.36 (s, 5H), 7.26~7.52 (m, 3H), 6.85~7.12 (m, 1H), 3.75 (s, 3H)

Example 54

7-Hydroxy-6-(3-methoxyphenyl)-3-(4-phenylthiophenyl)pyrazolo[1,5-a]pyrimidine

The title compound was obtained according to the procedure of Example 52.

mp: >300° C.

NMR (DMSO-d$_6$) δ: 8.27 (s, 1H), 7.97 (s, 1H), 7.64 (d, J=8.6 Hz, 2H), 7.41 (d, J=8.6 Hz, 2H), 7.36 (s, 5H), 7.20~7.34 (m, 3H), 6.83~6.96 (m, 1H), 3.80 (s, 3H)

Example 55

7-Hydroxy, 6-(4-fluorophenyl)-3-(4-phenylthiophenyl)-pyrazolo[1,5-a]pyrimidine

The title compound was obtained according to the procedure of Example 52.

mp: >300° C.

NMR (DMSO-d$_6$) δ: 8.27 (s, 1H), 7.97 (s, 1H) , 7.65 (d, J=8.8 Hz, 2H), 7.55~7.69 (m, 1H), 7.41 (d, J=8.8 Hz, 2H), 7.87 (s, 5H), 7.18 (d, J=9.0 Hz, 2H)

Example 56

7-Hydroxy-6-(3-fluorohepyl)-3-(4-phenylthiophenyl)-pyrazolo[1,5-a]pyrimidine

The title compound was obtained according to the procedure of Example 52.

mp: >300° C.

NMR (DMSO-d$_6$) δ: 8.29 (s, 1H), 8.07 (s, 1H), 7.65 (d, J=8.4 Hz, 2H), 7.42 (d, J=8.4 Hz, 2H), 7.37 (s, 5H), 7.02~7.78 (m, 4H)

Example 57

7-Hydroxy-6-(2-fluorophenyl)-3-(4-phenylthiophenyl)-pyrazolo[1,5-a]pyrimidine

The title compound was obtained according to the procedure of Example 52.

mp: >300° C.

NMR (DMSO-d$_6$) δ: 8.29 (s, 1H), 7.94 (s, 1H), 7.10~7.80 (m, 13H)

Example 58

7-Hydroxy-3,6-bis(4-phenylthiophenyl)pyrazolo[1,5-a]pyrimidine

The title compound was obtained according to the procedure of Example 52.

mp: 278°~280° C.

NMR (DMSO-d₆) δ: 8.27 (s, 1H), 8.00 (s, 1H), 7.71 (d, J=8.4 Hz, 2H), 7.64 (d, J=8.4 Hz, 2H), 7.41 (d, J=8.4 Hz, 2H), 7.37 (d, J=8.4 Hz, 2H), 7.32~7.39 (m, 10 H)

Example 59

6-(2-Acetoxyethyl)-7-hydroxy-3-(4-phenylthiophenyl)-pyrazolo[1,5-a]pyrimidine

To a benzene suspension of 1.0 g of 60% sodium hydride, 4 ml of ethyl formate and 1.6 ml of γ-butyrolactone were added under nitrogen atmosphere, and stirred for 24 hours at room temperature. After adding water, the solution was neutralized with 10% hydrochloric acid, and extracted with ethyl acetate, washed with water, dried in anhydrous sodium sulfate, and the solvent was distilled away. The residue was dissolved in 10 ml of acetic acid, and 2.0 g of 3-amino-4-(4-phenylthiophenyl)pyrazole was added, and the mixture was heated and stirred for 6 hours at 120° C. After allowing to cool, ethyl acetate was added, the filtrate was filtered, washed with ethyl acetate and ether, dried, and the title compound was obtained (400 mg, 13%).

mp: 265°~270° C.

NMR (DMSO-d₆) δ: 8.22 (s, 1H), 7.78 (s, 1H), 7.61 (d, J=38.6 Hz, 2H), 7.40 (d, J=8.6 Hz, 2H), 7.36 (s, 5H), 4.20 (t, J=6.6 Hz, 2H), 2.78 (t, J=6.6 Hz, 2H), 1.99 (s, 3H)

Example 60

7-Hydroxy-6-(2-hydroxyethyl)-3-(4-phenylthiophenyl)-pyrazolo[1,5-a]pyrimidine

To a methanol suspension of 180 mg of 6-(2-acetoxyethyl)-7-hydroxy-3-(4-phenylthiophenyl)pyrazolo[1,5-a]pyrimidine, 2 ml of 2N sodium hydroxide was added, and stirred for 21 hours at room temperature. Turning acidic with 10% hydrochloric acid, the precipitate was filtered, washed with-water, dried, and the title compound was obtained (150 mg, 93%).

mp: 244°~247° C.

NMR (DMSO-d₆) δ: 8.20 (s, 1H), 7.68 (s, 1H), 7.60 (d, J=8.6 Hz, 2H), 7.40 (d, J=8.6 Hz, 2H), 7.35 (s, 5H), 3.56 (t, J=6.8 Hz, 2H), 2.61 (t, J=6.4 Hz, 2H)

Example 61

7-Hydroxy-6-(2-hydroxyphenylmethyl)-3-(4-phenylthiophenyl)pyrazolo[1,5-a]pyrimidine To a dichloroethane suspension of 150 m₉ of 7-hydroxy-6-(2-methoxyphenylmethyl)-3-(4-phenylthiophenyl)[1,5-a]pyrimidine, 0.1 ml of boron tribromide was added while ice-cooling, and was stirred for 18 hours at room temperature. Adding water to the reaction solution, it was stirred for 1 hour. The precipitate was filtered, washed with water and methanol, dried, and the title compound was obtained (70 mg, 48%).

mp: 283°~287° C.

NMR (DMSO-d₆) δ: 9.42 (s, 1H), 8.22 (s, 1H), 7.60 (d, J=8.6 Hz, 2H), 7.56 (s, 1H), 7.39 (d, J=8.6 Hz, 2H), 7.35 (s, 5H), 6.95~7.20 (m, 2H), 6.71~6.84 (m, 2H), 3.71 (s, 2H)

Example 62

7-Hydroxy-6-(3-hydroxyphenylmethyl)-3-(4-phenylthiophenyl)pyrazolo[1,5-a]pyrimidine The title compound was obtained according to the procedure of Example 61.

mp: 235°~237° C.

NMR (DMSO-d₆) δ: 9.17 (bs, 1H), 8.21 (s, 1H), 7.70 (d, J=1.1 Hz, 1H), 7.60 (d, J=8.6 Hz, 2H), 7.39 (d, J=8.6 Hz, 2H), 7.35 (s, 5H), 7.06 (t, J=8.0 Hz, 1H), 6.51~6.75 (m, 3H), 3.71 (s, 2H)

Example 63

7-Hydroxy-6-(4-hydroxyphenylmethyl)-3-(4-phenylthiophenyl)pyrazolo[1,5-a]pyrimidine The title compound was obtained according to the procedure of Example 61.

mp: 287°~293° C.

NMR (DMSO-d₆) δ: 9.10 (bs, 1H), 8.20 (s, 1H), 7.65 (s, 1H), 7.60 (d, J=8.6 Hz, 2H), 7.39 (d, J=8.6 Hz, 2H) 7.35 (s, 5H), 7.10 (d, J=8.4 Hz, 2H), 6.66 (d, J=8.4 Hz, 2H), 3.68 (s, 2H)

Example 64

7-Hydroxy-6-(2-hydroxyphenyl)-3-(4-phenylthiophenyl)pyrazolo[1,5-a]pyrimidine

The title compound was obtained according to the procedure of Example 61.

mp: >300° C.

NMR (DMSO-d₆) δ: 9.32 (bs, 1H), 8.26 (s, 1H), 7.83 (s, 1H), 7.65 (d, J=8.4 Hz, 2H), 7.42 (d, J=8.4 Hz, 2H) 7.37 (s, 5H), 7.10~7.52 (m, 2H), 6.76~6.94 (m, 2H)

Example 65

7-Hydroxy-6-(3-hydroxyphenyl)-3-(4-phenylthiophenyl)pyrazolo[1,5-a]pyrimidine

The title compound was obtained according to the procedure of Example 61.

mp: >300° C.

NMR (DMSO -d₆) δ: 9.37 (bs, 1H), 8.26 (s, 1H), 7.69 (s, 1H), 7.63 (d, J=8.6 Hz, 2H), 7.41 (d, J=8.6 Hz, 2H) 7.36 (s, 5H), 7.00~7.22 (m, 3H), 6.66~6.80 (m, 1H)

Example 66

7-Hydroxy-6-(4-hydroxyphenyl)-3-(4-phenylthiophenyl)pyrazolo[1,5-a]pyrimidine

The title compound was obtained according to the procedure of Example 61.

mp: >300° C.

NMR (DMSO-d₆) δ: 9.42 (s, 1H), 8.26 (s, 1H), 7.83 (s, 1H), 7.64 (d, J=8.4 Hz, 2H), 7.42 (d, J=8.4 Hz, 2H), 7.47 (d, J=8.4 Hz, 2H), 7.36 (s, 5H), 6.81(d J=8.4 Hz, 2H)

Example 67

7-Hydroxy-6-acetyl-3-(4-phenylthiophenyl)-pyrazolo[1,5-a]pyrimidine

A mixture of 534 mg of 3-amino-4-(4-phenylthiophenyl)pyrazole, 484 mg of ethyl ethoxymethyleneacetoacetate, and 15 ml of acetic acid was stirred at room temperature. The precipitate was filtered 30 minutes later, and washed with n-hexane. The mixture of the obtained precipitate, 290 mg of sodium methoxide and 50 ml of toluene was concentrated in vacuo, and 2N hydrochloric acid, methylene chloride and ethyl acetate were added to the residue, and after separating, the organic layer was dried with over anhydrous magnesium sulfate, and concentrated in vacuo. The residue was recrystallized in methylene chloride-ethyl acetate (=1:1), and the title compound was obtained (350 mg)

mp: 275°~283° C.

NMR (DMSO-d₆) δ: 8.32 (s, 1H), 8.31(s, 1H), 7.38~7.69 (m, 9H), 2.60 (s, 3H)

Example 68

7-Hydroxy-6-benzoyl-3-(4-phenylthiophenyl)-pyrazolo[1,5-a]pyrimidine

The title compound was obtained according to the procedure of Example 67.

mp: 277°~290° C.

NMR (DMSO-$d_6$) δ: 8.32 (s, 1H), 8.18 (s, 1H), 7.38°~7.84 (m, 14H)

Example 69

7-Hydroxy-6-trifluoroacetyl-3-(4-phenylthiophenyl)-pyrazolo[1,5-a]pyrimidine

The title compound was obtained according to the procedure of Example 67, except that ethanol was used instead of toluene.

mp: 265°~286° C.

NMR (DMSO-$d_6$) δ: 8.46 (s, 1H), 8.31 (s, 1H), 8.12 (d, J=8.13 Hz, 2H), 7.39 (d, J=8.13 Hz, 2H), 7.29 (s, 5H)

Example 70

7-Hydroxy-6-(1-hydroxyethyl)-3-(4-phenylthiophenyl)-pyrazolo[1,5-a]pyrimidine

A mixture of 108 mg of 7-hydroxy-6-acetyl-3-(4-phenylthiophenyl)pyrazolo[1,5-a]pyrimidine, 46 mg of sodium borohydride, 2.3 ml of aqueous solution of 2N sodium hydroxide and 5 ml of ethanol was heated and refluxed. One hour later, the reaction mixture was concentrated in vacuo, 4 ml of water was added to the residue, and the mixture was neutralized with 2N hydrochloric acid. The precipitate was filtered, washed in water, dried, and the title compound was obtained (87 mg).

mp: 262°~285° C.

NMR (DMSO-$d_6$) δ: 8.24 (s, 1H), 7.29~7.67 (m, 10H), 4. 84 (q, J=6.37 Hz, 1H), 1.3.6 (d, J=6.15 Hz,

Example 71

7-Hydroxy-6-(α-hydroxybenzyl)-3-(4-phenylthiophenyl)pyrazolo[1,5-a]pyrimidine

The title compound was obtained according to the procedure of Example 70.

mp: 192°~198° C.

NMR (DMSO-$d_6$) δ: 8.20 (s, 1H), 8.17 (d, J=8.35 Hz, 2H), 7.88 (s, 1H), 7.19~7.61 (m, 12H), 5.96 (d, J=4.83 Hz, 1H), 5.49 (d, J=5.05 Hz, 1H)

Example 72

7-Hydroxy-6-(1-hydroxy-2,2,2-trifluoroethyl)-3-(4-phenylthiophenyl)pyrazolo[1,5-a]pyrimidine The title compound was obtained according to the procedure of Example 70.

mp: 265°~290° C.

NMR (DMSO-$d_6$) δ: 8.28 (s, 1H), 7.85 (s, 1H), 7.37~7.71 (m, 9H), 6.89 (d, J=6.15 Hz, 1H), 5.17~5.47 (m, 1H)

Example 73

6-(3-bromo-4-methoxyphenyl)-7-hydroxy-3-(4-phenylthiophenyl)pyrazolo[1,5-a]pyrimidine To a 2-ml nitrobenzene suspension of 420 mg of 7-hydroxy-6-(4-methoxyphenyl)-3-(4-phenylthiophenyl)-pyrazolo[1,5-a]pyrimidine, 0.1 ml of bromine was added and stirred for 1 hour at room temperature, and water and ether were added, and the precipitate was filtered. It was washed with water, methanol, ethyl acetate and ether, dried, and the title compound was obtained (270 mg, 54%).

mp: >300° C.

NMR (DMSO-$d_6$) δ: 8.29 (s, 3H), 7.10~8.00 (m, 12H), 3.89 (s, 3H)

Example 74

6-Ethoxycarbonyl-7-Hydroxy-3-(3-methyl-4-phenylthiophenyl)pyrazolo[1,5-a]pyrimidine The title compound was obtained according to the procedure of Example 1.

NMR (DMSO-$d_6$) δ: 8.37 (s, 1H), 8.28 (s, 1H), 7.22~7.5 9 (m, 8H), 4.28 (q, J=7.03 Hz, 2H), 2.39 (s, 3H), 1.29 (t, J=7.03 Hz, 3H)

Example 75

6-Carboxy-7-hydroxy-3-(3-methyl-4-phenylthiophenyl)pyrazolo[1,5-a]pyrimidine

The title compound was obtained according to the procedure of Example 38.

NMR (DMSO-$d_6$) δ: 8.48 (s, 1H), 8.39 (s, 1H), 7.24~7.75 (m, 8H), 2.38 (s, 3H)

Example 76

7-Hydroxy-3-(3-methyl-4-phenylthiophenyl)-pyrazolo[1,5-a]pyrimidine

The title compound was obtained according to the procedure of Example 48.

mp: 267°~27° C. (decomposed)

NMR (DMSO-$d_6$) δ: 8.23 (s, 1H), 7.77~7.87 (br, 1H), 2.28~8.0 (m, 8H), 5.79 (d, J=7.47 Hz, 1H), 2.38 (s, 3H)

Reference Example 8

1) In a nitrogen stream, a mixture of 241.88 g of 4-chlor-3-nitrobenzoic acid, 100.80 g of sodium hydrogencarbonate, and 900 ml of 50% water-containing methanol was stirred at room temperature, and 128.35 ml of thiophenyl, and 200 ml solution of 50% water-containing methatnol in which 49.6 g of sodium hydroxide was dissolved were sequentially added. The mixture was refluxed for 1 hour under nitrogen atmosphere. After reaction, the reaction mixture was cooled in ice water, and concentrated hydrochloric acid was added to adjust to pH 2 to 3, and a yellow precipitate was filtered, washed with water, and 3-nitro-4-phenylthiobenzoic acid was obtained. This was directly used in the following reaction.

2) To a mixture of 3-nitro-4-phenylthiobenzoic acid obtained above, 201.0 of iron powder and 800 ml of 50% water-containing ethanol, 40 ml ethanol solution of 20ml of concentrated hydrochloric acid was gradually added while stirring in reflux. After refluxing for 15 hours while stirring, the reaction mixture was cooled, and the precipitate was filtered and washed in water. To the obtained precipitate, 50 g of sodium hydroxide and 1.95 liters of water were added, and the mixture was heated and dissolved, and the insoluble matter was filtered away, and diluted sulfuric acid was added to the filtrate while ice-cooling to adjust to pH 2 to 3. The precipitate was filtered, washed in water, and dried, and 218.28 g of 3-amino-4-phenylthiobenzoic acid was obtained.

3) Adding 110.27 g of 3-amino-4-phenylthiobenzoic acid to 400 ml heated water solution of concentrated sulfuric acid (81 ml), the mixture was heated and stirred for 2 hours, and cooled with ice-salt bath to −5° C. To this solution, a 80 ml water solution of 36.25 g of sodium nitride which was ice-cooled was added in about 1 hour. Further stirring for 30 minutes at 0° to 5° C., 2 g of urea was added and stirred for 30 minutes, and the unreacted nitrous acid was decomposed, the obtained mixture was gradually added to a mixture of 121 ml of concentrated sulfuric acid, 168 g of anhydrous sodium sulfate and 112 ml of water, while stirring, in 75 minutes at 100° to 110° C. After addition, the mixture was further stirred for 1 hour at the same temperature. The reaction mixture was cooled, and precipitating brown granules were filtered, washed with water, and dried overnight at 50° C. The obtained product was added to the mixture of 1.4 liters of methanol and 70 ml of concentrated sulfuric acid, and the mixture was refluxed for 2 hours while stirring. After termination of reaction, the reaction mixture was concentrated in vacuo, and 1.5 liters of water was added to the residue, and the product was extracted with ethyl acetate (500 ml×3). The extract was dried in anhydrous sodium sulfate, and concentrated in vacuo. The residue was extracted in 4.2 liters of hot hexane, and cooled, and precipitating yellow matter was filtered, and 49.37 g of methyl 3-hydroxy-4-phenylthiobenzoate was obtained.

NMR (CDCl$_3$) δ: 7.13~7.71 (m, 8H), 6.47 (bs, 1H), 3.92(s, 3H)

Reference Example 9

To a mixture of 49.11 g of methyl 3-hydroxy-4-phenylthiobenzoate, 27.33 g of potassium carbonate and 627 ml of acetone, 17.85 ml of dimethyl sulfate was added, and the mixture was refluxed for 6 hours while stirring. The reaction mixture was cooled, and the precipitate was filtered and washed with acetone. The filtrate and washing liquid were combined, and concentrated in vacuo, and methyl 3-methoxy-4-phenylthiobenzoate was obtained.

NMR (CDCl$_3$) δ: 7.35~7.51(m, 7H), 6.79 (d, J=8.57 Hz, 1H), 3.96 (s, 3H), 3.88 (s, 3H)

Reference Example 10

1) To a 744-ml dry diethylether solution of 30.67 g of methyl 3-methoxy-4-phenylthiobenzoate, while ice-cooling and stirring, 4.32 g of lithium aluminium hydride was gradually added. After stirring for 1 hour, ethyl acetate, methanol and water were added to the reaction mixture, and the unreacted lithium aluminium hydride was decomposed. After separating the organic layer, the water layer was extracted with ethyl acetate (300 ml×2). The extract was combined with the organic layer, and washed with saturated brine (300 ml×2), and dried in anhydrous sodium sulfate, and concentrated in vacuo, thereby obtaining 1-hydroxymethyl-3-methoxy-4-phenylthiobenzene.

NMR (CDCl$_3$) δ: 7.20~7.37 (m, 5H), 7.04 (d, J=7.69 Hz, 1H), 6.95 (bs, 1H), 6.84 (bd, J=7.91 Hz, 1H), 4.68 (s, 2H), 3.87 (s, 3H)

2) Thus obtained 1-hydroxymethyl-3-methoxy-4-phenylthiobenzene was dissolved in 372 ml of methylene chloride, and 9.12 ml of thionyl chloride was added while stirring in ice-cooling. After stirring for 1 hour, the reaction mixture was washed with ice water (500 ml×2), and 500 ml of ethyl acetate was added. The mixture was sequentially washed with 20 ml of aqueous solution of 5% sodium hydrogencarbonate, 200 ml of water and 200 ml×2 of saturated brine, and dried in anhydrous sodium sulfate, and concentrated in vacuo, thereby obtaining 1-chloromethyl-3-methoxy-4-phenylthiobenzene.

NMR (CDCl$_3$) δ: 7.25~7.32 (m, 5H), 6.89~6.94 (m, 3H), 4.55 (s, 2H), 3.89 (s, 3H)

3) Thus obtained 1-chloromethyl-3-methoxy-4-phenylthiobenzene was dissolved in 200 ml of N,N-dimethylformamide, and 7.34 g of finely ground sodium cyanide was added and stirred for 14 hours at 30° C. To the reaction mixture, 300 ml of saturated brine and 300 ml of ice water were added, and the mixture was extracted with ethyl acetate (300 ml×3). The extract was washed with saturated brine (200 ml×3), and dried with anhydrous sodium sulfate, and 1-cyanomethyl-3-methoxy-4-phenylthiobenzene was obtained.

NMR (CDCl$_3$) δ: 7.25~7.41 (m, 5H), 7.01 (d, J=7.70, 1H), 6.83 (s, 1H), 6.79 (d, J=7.4 7 Hz, 1H), 3.89 (s, 3H), 3. 72 (s, 2H)

Reference Example 11

A solution of 70 ml of N,N-dimethylacetamide in which 20.86 g of potassium hydroxide was dissolved was heated to 150° C., and 19.52 ml of thiophenol and 25.47 g of 4-bromobenzoic acid were added under nitrogen atmosphere while stirring at the same temperature. After reflux for 20 hours under nitrogen atmosphere, the reaction mixture was poured into 400 ml of ice water, and 400 ml of benzene was added to wash, and the water layer was separated. The benzene layer was extracted with 2.5N sodium hydroxide (100 ml×4). The extract was combined with the water layer and the pH was adjusted to 1 to 2 with concentrated hydrochloric acid, and the precipitate was filtered, washed in water, dried, and 4-phenylthiobenzoic acid was obtained (26.29 g).

NMR (DMSO-d$_6$) δ: 7.95 (d, J=8.57 Hz, 2H), 7.34~7.48 (m, 5H), 7.20 (d, J=8.57 Hz, 2H)

Reference Example 12

A mixture of 26.29 g of 4-phenylthiobenzoic acid, 5 ml of concentrates sulfuric acid, and 400 ml of methanol was refluxed for 10 hours while stirring. After reaction, the reaction mixture was concentrated in vacuo, and 400 ml of ethyl acetate was added to the residue, and the mixture was washed with saturated brine (200 ml×3), and dried in anhydrous magnesium sulfate, concentrated in vacuo, and methyl 4phenylthiobenzoate was obtained (27.44 g).

NMR (CDCl$_3$) δ: 7.89 (d, J=8.58 Hz, 2H), 7.32~7.53 (m, 5H), 7.20 (d, J=8.79 Hz, 2H), 3.88 (s, 3H)

Reference Example 13

1) To a solution of 500 ml of dry diethylether in which 27 g of methyl 4-phenylthiobenzoate was dissolved, 2.5 g of lithium aluminium hydride was gradually added in ice-cooling, while stirring. After stirring for 1 hour, ethyl acetate and water were sequentially added to the reaction mixture, and the unreacted lithium aluminium hydride was decomposed. After separating the organic layer, the water layer was extrated with ethyl acetate (100 ml×2). The extract was combined with the organic layer, and washed with saturated brine (100 ml×2), and dried with anhydrous sodium sulfate, concentrated in vacuo, and 1-hydroxymethyl-4-phenylthiobenzene was obtained (25 g ).

NMR (CDCl$_3$) δ: 7.19~7.40 (m, 9H), 4.67 (s, 2H)

2) Dissolving 3.0 g of 1-hydroxymethyl-4-phenylthiobenzene in 15 ml of methylene chloride, 1.5 ml of thionyl chloride was added while stirring in ice-cooling. After stirring for 1 hour, the reaction mixture was washed in ice water (10 ml×3), and 50 ml of methylene chloride was added. The mixture was sequentially washed with aqueous solution of 5% sodium hydrogencarbonate (5 ml×3) and saturated brine (30 ml×2), and dried with anhydrous sodium sulfate, and concentrated in vacuo, thereby obtaining 1-chloromethyl-4-phenylthiobenzene (3.0 g).

NMR (CDCl$_3$) δ: 7.25~7.35 (m, 9H), 4.54 (s, 2H)

3) Dissolving 3.0 g of 1-chloromethyl-4-phenylthiobenzene (3.0 g) in 15 ml of N,N-dimethylformamide, 1.0 g of finely ground sodium cyanide was added and stirred for 17 hours at room temperature. To the reaction mixture, 50 ml of saturated brine and 50 ml of ice water were added, and the mixture was extracted with ethyl acetate (100 ml×3). The extract was washed with saturated brine (50 ml×3), and dried with anhydrous sodium sulfate, and concentrated in vacuo, and 1-cyanomethyl-4-phenylthiobenzene was obtained (2.9 g).

NMR (CDCl$_3$) δ: 7.29~7.38 (m, 9 H) , 3.7 1 (s, 2H)

Reference Example 14

Dissolving 1.368 g of potassium hydroxide in 20 ml of N,N-dimethylacetamide in heated state, and 1.16 ml of thiophenol was added in a nitrogen stream. In succession, 4-chloro-3-methylbenzoic acid was added, and the mixture was refluxed for 2 days under nitrogen atmosphere. After reaction, the reaction mixture was cooled, and poured into about 100 ml of ice water, and washed in 50 ml of benzene, and the water layer was separated. The benzene layer was further extracted with 50 ml of aqueous solution of 5% sodium hydroxide, and the extract and water layer were combined and the pH was adjusted to 2 to 3 with hydrochloric acid, and the precipitate was filtered, washed in water, dried, and 3-methyl-4-phenylthiobenzoic acid was obtained (1.55 g).

Reference Example 15

A mixture was 85 g of 3-methyl-4-phenylthiobenzoic acid, 20 ml of concentrated sulfuric acid, and 1.2 liters of methanol was refluxed for 4 hours while stirring. After reaction, the reaction mixture was concentrated in vacuo, and 1.5 liters of ethyl acetate was added to the residue, and the mixture was washed with saturated brine (400 ml×3), and dried with anhydrous sodium sulfate, concentrated in vacuo, and methyl 3-methyl-4-phenylthiobenzoate was obtained (80.33 g).

NMR (CDCl$_3$) δ: 7.85 (bs, 1H), 7.70 (bd, J=8.13 Hz, 1H), 7.37 (bs, 5H) 7.00 (d, J=8.13 Hz, 1H)

Reference Example 16

1) To a 900-ml dry diethylether solution of 80.33 g of methyl 3-methyl-4-phenylthiobenzoate, 7.08 g of lithium aluminium hydride was gradually added while ice-cooling and stirring. After stirring for 1 hour, ethyl acetate, methanol and water were sequentially added to the reaction mixture, and the unreacted lithium aluminium hydride was decomposed. After separating the organic layer, the water layer was extracted with ethyl acetate (300 ml×2), and the extract was combined with organic layer, and the mixture was washed with saturated brine (300 ml×2), and dried with anhydrous sodium sulfate, concentrated in vacuo, and 1-hydroxymethyl-3-methyl-4-phenylthiobenzene was obtained.

NMR (CDCl$_3$) δ: 7.04~7.36 (m, 8H), 4.62 (s, 2H), 2.37 (s, 3H)

2) Thus obtained 1-hydroxymethyl-3-methyl-4-phenylthiobenzene was dissolved in 100 ml of methylene chloride, and 23.34 ml of thionyl chloride was added while ice-cooling and stirring. After stirring for 1 hour, the reaction mixture was washed with ice water (100 ml×3), and 500 ml of ethyl acetate was added. The mixture was sequentially washed with 5% aqueous solution of sodium hydrogencarbonate (50 ml×4) and saturated brine (100 ml×2), and dried with anhydrous sodium sulfate, concentrated in vacuo, and 1-chloromethyl-3-methyl-4-phenylthiobenzene was obtained.

NMR (CDCl$_3$) δ: 7.16~7.2 5 (m, 8H), 4.53 (s, 2H), 2.87 (s, 3H)

3) Thus obtained 1-chloromethyl-3-methyl-4-phenylthiobenzene was dissolved in 56 ml of N,N-dimethylformamide, and 18.16 g of finely ground sodium cyanide was added, and the mixture was stirred overnight at room temperature. After adding 300 ml of saturated brine and 300 ml of ice water to the reaction mixture, it was extracted with ethyl acetate (300 ml×3). The extract was washed with saturated brine (200 ml×3), and dried with anhydrous sodium sulfate, concentrated in vacuo, and 1-cyanomethyl-3-methyl-4-phenylthiobenzene was obtained (45.95 g).

NMR (CDCl$_3$) δ: 7.10~7.37 (m, 8H), 8.69 (s, 2H), 2.38 (s, 3H)

Example 77

20 4-Hydroxy-8-(4-phenylthiophenyl)pyrazolo[1,5-a]-1,3,5-triazine

A mixture of 124.15 g of 3-amino-2-carbamoyl-(4-phenylthiophenyl)pyrazole, 80 ml of ethyl orthoformate, and 100 ml of N,N-dimethylformamide was heated and stirred for 40 minutes at 100 ° to 110° C., and methanol or ethyl acetate was added, and the precipitate was filtered, washed with methanol or ethyl acetate, dried, and the title compound was obtained (93.46 g).

mp: 297°~298° C.

NMR (DMSO-d$_6$) δ: 8.58 (s, 1H), 8.12 (s, 1H), 8.04 (d, J=8.4 Hz, 2H), 7.41 (d, J=8.5 Hz, 2H), 7.34 (s, 5H)

Thereafter, in the same manner as in Example 77, using proper starting materials, the compounds of Examples 78 to 87 were obtained.

Example 78

4-Hydroxy-8-[4-(2-methylphenylthio)phenyl]-pyrazolo[1,5-a]-1,3,5-triazine mp:>300° C.

NMR (DMSO-d$_6$) δ: 8.55 (s, 1H), 8.10 (s, 1H), 8.00 (d, J=8.35 Hz, 2H) , 7.27 (d, J=8.35HZ, 2H) , 7.20~8.29 (m, 4H)

Example 79

8-(4-Benzylthio-3-methylphenyl)-4-hydroxypyrazolo[1,5-a]-1,3,5-triazine.

mp: 234°~236° C.

NMR (DMSO-d$_6$) δ: 8.55 (s, 1H), 8.10 (s, 1H), 7.86 (s, 1H), 7.82 (dd, J=8.0 or 1.7 Hz, 1H) 7.20~7.45 (m, 6H), 4.21 (s, 2H),2.28 (s, 3H)

Example 80

4-Hydroxy-8-[4-(4-methylphenylthio)phenyl]-pyrazolo[1,5-a]-1,3,5-triazine
mp:>300° C.
NMR (DMSO-d$_6$) δ: 8.56 (s, 1H), 8.11 (s, 1H), 7.99 (d, J=8.6 Hz, 2H), 7.32 (d, J=8.6 Hz, 2H), 7.30 (d, J=8.8 Hz, 2H), 7.18 (d, J=8.8 Hz, 2H), 2.31 (s, 3H)

Example 81

4-Hydroxy-8-(3-methyl-4-phenylthiophenyl)-pyrazolo[1,5-a]-1,3,5-triazine
mp: 274°~276° C.
NMR (DMSO-d$_6$) δ: 8.59 (s, 1H), 8.13 (s, 1H), 8.01 (bs, 1H), 7.89 (dd, J=8.1 or 1.5 Hz, 1H), 7.36 (d, J=8.0 Hz, 1H), 7.11~7.42 (m, 5H), 2.36(s, 3H)

Example 82

4-Hydroxy-8-[3-methyl-4-(2-methylphenylthio)-phenyl]pyrazolo[1,5-a]-1,3,5-triazine
mp: 246°~251° C. (decomposed)
NMR (DMSO-d$_6$) δ: 8.56 (s, 1H), 8.11 (s, 1H), 7.98 (bs, 1H), 7.84 (bd, J=8.13 Hz, 1H), 6.9~7.4 (m, 5H), 2.36 (s, 3H), 2.33 (s, 3H)

Example 83

4-Hydroxy-8-[3-methyl-4-(3-methylphenylthio)-phenyl]pyrazolo[1,5-a]-1,3,5-triazine
mp: 270°~278° C.
NMR (DMSO-d$_6$) δ: 8.59 (s, 1H), 8.13 (s, 1H), 7.99 (s, 1H), 7.87 (dd, J=7.9 or 1.7 Hz, 1H) 7.32 (d, J=8.0 Hz, 1H), 6.90~7.40 (m, 4H), 2.36 (s, 3H), 2.26 (s, 3H)

Example 84

4-Hydroxy-8-[3-methyl-4-(4-methylphenylthio)-phenyl]pyrazolo[1,5-a]-1,3,5-triazine
mp: 287°~290° C.
NMR (DMSO-d$_6$) δ: 8.56 (s, 1H), 8.12 (s, 1H), 7.97 (d, J=1.5 Hz, 1H), 7.82 (dd, J=9.3 or 2.0 Hz, 1H), 7.23 (d, J=9.3 Hz, 1H), 7.15 (s, 4H), 2.35 (s, 3H), 2.28 (s, 3H)

Example 85

4-Hydroxy-8-[4-(3-methoxyphenylthio)-3-methyl]-phenylpyrazolo[1,5-a]-1,3,5-triazine
mp: 245°~249° C.
NMR (DMSO-d$_6$) δ: 8.60 (s, 1H), 8.13 (s, 1H), 8.02 (bs, 1H), 7.91 (dd, J=7.9 or 1.6 Hz, 1H), 7.39 (d, J=8.4 Hz, 1H), 7.20 (d, J=8.1 Hz, 1H), 6.67~6.85 (m, 3H), 3.70 (s, 3H), 2.36 (s, 3H)

Example 86

4-Hydroxy-8-[4-(4-methoxyphenylthio)-3-methyl]-phenylpyrazolo[1,5-a]-1,3,5-triazine
mp: 283°~287° C.
NMR (DMSO-d$_6$) δ: 8.53 (s, 1H), 8.10 (s, 1H), 7.92 (d, J=1.5 Hz 1H), 7.77 (dd, J=8.1 or 1.7 Hz, 1H), 7.31 (d, J=9.0 Hz, 2H), 7.03 (d, J=8.1 Hz, 1H), 6.97 (d, J=9.0 Hz, 2H), 3.77 (s, 3H), 2.36 (s, 3H)

Example 87

4-Hydroxy-8-(4-phenylaminosulfonylphenyl)-pyrazolo[1,5-a]-1,3,5-triazine

A mixture of 420 mg of 4-hydroxy-8-phenyl-pyrazolo[1,5-a]-1,3,5-triazine and 3ml of chlorosulfonic acid was heated and stirred at 80° C. One hour later, water was added to the reaction solution, the precipitate was filtered, washed with water and dried. To the filtered material, 10 ml of aniline was added, and the mixture was heated and stirred at 80° C. Two hours later, 2N hydrochloric acid was added to make the reaction solution acidic, and the precipitate was filtered, washed with water and dried, and the title compound was obtained (420 mg).
mp 274°~277° C.
NMR (DMSO-d$_6$) δ: 10.21 (s, 1H), 8.62 (s, 1H), 8.17 (d, J=8.6 Hz, 2H), 8.16 (s, 1H), 7.78 (d, J=8.6 Hz, 2H), 6.92~7.34 (m, 5H)

Thereafter, in the same manner as in Example 87, by using proper starting materials, the compounds of Examples 88 to 100 were obtained.

Example 88

4-Hydroxy-8-[4-(4-methylphenylaminosulfonyl)-phenyl]pyrazolo[1,5-a]-1,3,5-triazine
mp: 262°~265° C.
NMR (DMSO-d$_6$) δ: 10.05(s, 1H), 8.63(s, 1H), 8.17 (d, J=8.6 Hz, 2H), 8.16 (s, 1H), 7.76 (d, J=8.6 Hz, 2H), 7.01 (s, 4H), 2.18 (s, 3H)

Example 89

8-[4-(4-Ethylphenylaminosulfonyl)phenyl]-4-hydroxypyrazlo[1,5-a]-1,3,5-triazine
mp: 285°~290° C.
NMR (DMSO-d$_6$) δ: 10.09 (s, 1H), 8.63 (s, 1H), 8.17 (s, 1H), 8.17 (d, J=8.6 Hz, 2H), 7.78 (d, J=8.6 Hz, 2H), 7.04 (s, 4H), 2.25 (q, J=7.3 Hz, 2H), 1.17 (t, J=7.3 Hz, 3H)

Example 90

8-[4-(3-ethylphenylaminosulfonyl)phenyl]-4-hydroxypyrazolo[1,5-a]-1,3,5-triazine
mp: 240°~248° C.
NMR (DMSO-d$_6$) δ: 10.15 (s, 1H), 8.68 (s, 1H), 8.18(d, J=8.6 Hz, 2H), 8.16(s, 1H), 7.79(d, J=8.6 Hz, 2H), 6.70~7.50 (m, 4H), 2.20~2.60 (m, 2H), 1.08 ( t, J=7.2 Hz, 3H)

Example 91

8-[4-(2-ethylphenylaminosulfonyl)phenyl]-4-hydroxypoyrazolo[1,5-a]-1,3,5-triazine
mp: 250°~254° C.
NMR (DMSO-d$_6$) δ: 9.51(s, 1H), 8.67 (s, 1H), 8.21 (d, J=8.6 Hz, 2H), 8.18 (s, 1H), 7.71 (d, J=8.6 Hz, 2H), 7.07~7.25 (m, 4H), 2.46~2.57 (m, 2H), 0.97 (t, J=7.7 Hz, 3H)

Example 92

4-Hydroxy-8-[4-(4-isopropylphenylaminosulfonyl)-phenyl]pyrazolo[1,5-a]-1,3,5-triazine
mp: 290°~295° C.
NMR (DMSO-d$_6$) δ: 10.10 (s, 1H), 8.63 (s, 1H), 8.18 (d,J=8.6 Hz, 2H) , 8.16 (s, 1 H), 7.78 (d,J=8.6 Hz, 2H) , 7.00~7.2 0m, 4H), 2.46~2.52 (m, 1H), 1.11 (d, J=6.8 Hz, 6H)

Example 93

8-[4-(4-t-butylphenylaminosulfonyl)phenyl]-4-hydroxypyrazolo[1,5-a]-1,3,5-triazine
mp: 275°~279° C.
NMR (DMSO-d$_6$) δ: 10.13 (s, 1H), 8.63 (s, 1H), 8.18 (d, J=8.6 Hz, 2H), 8.17 (s, 1H), 7.80 (d, J=8.6 Hz, 2H), 7.25 (d, J=8.8 Hz, 2H), 7.02 (d, J=8.8 Hz, 2H), 1.19 (s, 9H)

Example 94

8-[4-(4-cyanophenylaminosulfonyl)phenyl]-4-hydroxypyrazolo[1,5-a]-1,3,5-triazine
mp: 272°~274° C.

NMR (DMSO-d$_6$) δ: 11.01 (s, 1H), 8.64 (s, 1H), 8.22 (d, J=8.6 Hz, 2H), 8.18 (s, 1H), 7.88 (d, J=8.6 Hz, 2H), 7.70 (d, J=9.0 Hz, 2H), 7.28 (d, J=9.0 Hz, 2H)

Example 95

8-[4-(4-chlorophenylaminosulfonyl)phenyl]-4-hydroxypyrazolo[1,5-a]-1,3,5-triazine
mp 189°~193° C.

NMR (DMSO-d$_6$) δ: 10.38 (s, 1H), 8.64 (s, 1H), 8.20 (d, J=8.6 Hz, 2H), 8.17(s, 1H), 7.79 (d, J=8.6 Hz, 2H), 7.31 (d, J=9.0 Hz, 2H), 7.12 (d, J=9.0 Hz, 2H)

Example 96

4-Hydroxy-8-[4-(3,4,5-trichlorophenylaminosulfonyl)-phenylpyrazolo[1,5-a]-1,3,5-triazine
mp: 280°~283° C.

NMR (DMSO-d$_6$) δ: 10.91 (bs, 1H), 8.66 (s, 1H), 8.25 (d, J=8.8 Hz, 2H), 8.19 (s, 1 H) , 7.87 (d, J=8.8 Hz, 2H), 7.32 (s, 2H)

Example 97

4-Hydroxy-8-[4-(3-pyridylaminosulfonyl)phenyl]-pyrazolo[1,5-a]-1,3,5-triazine
mp: >300° C.

NMR (DMSO-d$_6$) δ: 8.64 (s, 1H), 8.20 (d, J=8.6 Hz, 2H), 8.17 (s, 1H), 8.14 ~8.33 (m, 2H), 7.30~7.50 (m, 4H)

Example 98

8-(4-cyclohexylaminosulfonylphenyl)-4-hydroxypyrazolo[1,5-a]-1,3,5-triazine mp:>300° C.

NMR (DMSO-d$_6$) δ: 8.68 (s, 1H), 8.23 (d, J=8.6 Hz, 2H), 8.18 (s, 1H), 7.86 (d, J=8.6 Hz, 2H), 7.59 (d, J=7.0 Hz, 1H), 2.70~3.00 (m, 1H), 1.00~1.62 (m, 10H)

Example 99

4-Hydroxy-8-[4-(4-t-butylphenylaminosulfonyl)-3-methylphenyl]pyrazolo[1,5-a]-1,3,5-triazine
mp: 258°~260° C.

NMR (DMSO-d$_6$) δ: 10.24 (s, 1H), 8.63 (s, 1H), 8.17 (s, 1H), 7.99 (bs, 3H), 7.23 (d, J=8.8 Hz, 2H), 7.00 (d, J=8.8 Hz, 2H), 2.50 (s, 3H), 1.18(s, 9H)

Example 100

8-[4-(4-bromophenylthio)-3-methylphenyl]-4-hydroxypyrazolo[1,5-a]-1,3,5-triazine
mp:>300° C.

NMR (DMSO-d$_6$) δ: 8.61 (s, 1H), 8.14 (s, 1H), 8.03 (d, J=2.0 Hz, 1H), 7.93 (dd, J=8.1 or 2.0 Hz, 1H), 7.50 (d, J=8.8 Hz, 2H), 7.43 (d, J=8.1 Hz, 1H), 7.10 (d, J=8.6 Hz, 2H), 2.36 (s, 3H)

Example 101

1.0    4-Hydroxy-8-(3-methoxy-4-phenylthiophenyl)-pyrazolo [1,5-a]-1,3,5-triazine The title compound was obtained by using a proper starting material in the same manner as in Example 77.
mp: 247°~248° C.

NMR (DMSO-d$_6$) δ: 8.64 (s, 1H), 8.13 (s, 1H), 7.74 (d, J=1.75 Hz, 1H), 7.63 (dd, J=7.91 or 1.75 Hz, 1H), 7.22~7.35 (m, 5H), 7.15 (d, J=7.91 Hz, 1H)

Example 102

8-(3-chloro-4-phenylthiophenyl)-4-hydroxypyrazolo[1,5-a]-1,3,5-triazine

The title compound was obtained by using a proper starting material in the same manner as in Example 77.
mp: 290°~293° C.

NMR (DMSO-d$_6$) δ: 8.62 (s, 1H), 8.27 (d, J=2.0 Hz, 1H), 8.15 (s, 1H), 7.92 (dd, J=8.4 or 2.0 Hz, 1H) 7.41 (s, 5H), 7.16 (d, J=8.4 Hz, 1H)

Example 103

4-Hydroxy-8-(3-methyl-4-phenylaminosulfonylphenyl)-pyrazolo[1,5-a]-1,3,5-triazine The title compound was obtained by using a proper starting material in the same manner as in Example 87.
mp: 273°~275° C.

NMR (DMSO-d$_6$) δ: 10.36 (s, 1H), 8.61 (s, 1H), 8.17 (s, 1H), 7.77~8.29 (m, 3H), 6.74~7.35 (m, 5H), 2.64 (s, 3H)

Pharmaceutical examples are shown below.

Pharmaceutical Example 1

| | |
|---|---|
| 6-Ethoxycarbonyl-7-hydroxy-3-(4-phenylthiophenyl)-pyrazolo[1,5-a]pyrimidine | 100 g |
| Avicel (trademark, Asahi Chemical Industry Co., Ltd.) | 40 g |
| Corn starch | 30 g |
| Magnesium stearate | 2 g |
| TC-5 (trademark, Shin-Etsu Chemical Co., Ltd.; hydroxypropyl methylcellulose) | 10 g |
| Polyethylene glycol 6000 | 3 g |
| Castor oil | 40 g |
| Ethanol | 40 g |

After kneading 6-ethoxycarbonyl-7-hydrlxy-3-(4-phenylthiophenyl)-pyrazolo[1,5-a]pyrimidine, Avicel, corn starch, and magnesium stearate, tablets were prepared by using tableting machine for sugar coated tablet R10 mm. The obtained tablets were coated with film composed of polyethylene glycol 6000, castor oil and ethanol, and the film coated tablets in the composition specified above were manufactured.

Pharmaceutical Example 2

In the same manner as in Pharmaceutical example 1, the film coated tablets of the following composition were manufactured.

| | |
|---|---|
| 4-Hydroxy-8-[4-(4-methylphenylthio)-phenyl] pyrazolo[1,5-a]-1,3,5-trizine | 100 g |
| Avicel (trademark, Asahi Chemical Industry Co., Ltd.) | 40 g |
| Corn starch | 30 g |
| Magnesium stearate | 2 g |
| TC-5 (trademark, Shin-Etsu Chemical Co., Ltd.; hydroxypropyl methylcellulose) | 10 g |
| Polyethylene glycol 6000 | 3 g |
| Castor oil | 40 g |
| Ethanol | 40 g |

The compounds obtained in Examples were evaluated in the following pharmacological studies A and B. The pharmacological study A was conducted in conformity with J.B.C. 256 (15) 7998–8005, 1981.

A. Measurement of inhibitory activity on binding of $^3$H-5α-hydrotestosterone ($^3$H-5α,-DHT) on rat prostate androgen receptor (1) Preparation of cytosol from rat prostate The rat was sacrificed 24 hours after castration, and the ventral lobe of prostate was removed, and was gently homogenized, on ice water bath, by using a Potter homogenizer in three-fold amount of 0.25M sucrose-TME buffer solution (50 mM tris-HCl (pH 7.4), 0.5 mM mercaptoethanol, and 0.1 mM EDTA-2 Na). The homogenate was filtrated through double gauze, and ultra-centrifuged at 105000×g for 60 minutes, and the supernatant was used as androgen receptor.

(2) Measurement of $^3$H-5α-DHT specific binding on prostate cytoplasmic androgen receptor To the cytosol obtained in (1), $^3$H-5α-DHT (47.8 Ci/mmol) was added, so that a final concentration is adjusted to 1 nM, and 0.25 M sucrose-TME buffer was added to adjust the final volume to 0.5 ml, and the reaction mixture was incubated for about 20 hours at 0° C. An ammonium sulfate solution dissolved in 0.25 M sucrose-TME buffer was mixed to be 35% saturation, and after standing for 90 minutes at 0° C., the mixture was centrifuged at 10000×g for 10 minutes at 4° C., and the precipitate was obtained.

This precipitate was suspended again in 0.8 ml of the above buffer solution, and furthermore in order to remove the free type $^3$H-5α-DHT, 0.2 ml of dextran-carbon powder suspension (4% activated carbon, 0.1% dextran T-70, and 0.1% gelatin dissolved in the above buffer solution) was added and mixed, and the mixture was let stand for 10 minutes at 0° C. At 4° C., in succession, the mixture was centrifuged at 3000×g for 10 minutes, and 0.5 ml of the supernatant was transferred into a vial, and 10 ml of aquasol-2 was added, and radioactivity was measured, and the total binding amount of $^3$H-5α-DHT on the prostate cytoplasma androgen receptor was determined. The nonspecific binding amount was similarly determined by adding a non-radioactive ligand (5α-DHT) to the reaction solution to a final concentration of 1 μM. The difference between the total binding amount and nonspecific binding amount was determined as the specific binding amount on the androgen receptor.

(3) Inhibitory activity of sample compounds on $^3$H-5α-DHT specific binding

The compounds obtained in Examples were incubated with $^3$H-5α-DHT at several concentrations same as in (2), and the specific binding amount of $^3$H-5α-DHT on the androgen receptor was determined. Comparing the obtained value with the value of (2), the IC$_{50}$ value of the test compounds on $^3$H-5α-DHT specific binding was determined. The results are shown in Table 2. The following compounds were used as the positive controls.

Comparison 1: Flutamide
Comparison 2: Hydroxyflutamide

TABLE 2

| Test compound (Example No.) | Inhibitory activity on 5α-DHT specific binding [IC$_{50}$(M)] |
|---|---|
| 1 | $2.0 \times 10^{-6}$ |
| 3 | $8.5 \times 10^{-7}$ |
| 5 | $5.0 \times 10^{-7}$ |
| 77 | $9.6 \times 10^{-7}$ |
| 79 | $1.1 \times 10^{-7}$ |
| 81 | $1.5 \times 10^{-7}$ |
| 82 | $1.1 \times 10^{-6}$ |
| 83 | $1.3 \times 10^{-7}$ |
| 84 | $1.5 \times 10^{-6}$ |
| 85 | $1.6 \times 10^{-7}$ |
| 86 | $1.2 \times 10^{-7}$ |
| 87 | $1.3 \times 10^{-7}$ |
| 88 | $<5 \times 10^{-6}$ |
| 89 | $<5 \times 10^{-6}$ |
| 90 | $<5 \times 10^{-6}$ |

TABLE 2-continued

| Test compound (Example No.) | Inhibitory activity on 5α-DHT specific binding [IC$_{50}$(M)] |
|---|---|
| 91 | $<5 \times 10^{-6}$ |
| 92 | $<5 \times 10^{-6}$ |
| 94 | $6.0 \times 10^{-7}$ |
| 95 | $1.2 \times 10^{-6}$ |
| 97 | $5 \times 10^{-6}$ |
| 98 | $3.6 \times 10^{-7}$ |
| 100 | $4.0 \times 10^{-7}$ |
| 101 | $3.0 \times 10^{-7}$ |
| 102 | $2.2 \times 10^{-6}$ |
| 103 | $2.5 \times 10^{-7}$ |
| Comparison 1 | $>>1 \times 10^{-5}$ |
| Comparison 2 | $>5 \times 10^{-6}$ |

B. Measurement of inhibitory activity on binding of $^3$H-mibolerone on rat prostate androgen receptor (1) Preparation of cytosol from rat prostate The rat was sacrificed 24 hours after castration, and the ventral lobe of prostate was removed, and was gently homogenized, in ice-cooling water bath, at first by using Polytron and then using Potter type homogenizer, in three-fold amount of buffer solution A (1.5 mM EDTA, 2 mM dithiothreitol, 10 mM molybdate sodium, 10 % by volume of glycerol, 10 mM NaF, 25 mM phosphate sodium, pH 7.2). The obtained homogenate was filtrated through double gauze, and centrifuged at 105000×g for 60 minutes at 4° C., and the supernatant was obtained as cytoplasm fraction.

(2) Measurement of specific binding of $^3$H-mibolerone on prostate cytoplasm androgen receptor To the cytoplasm fraction obtained in (1), $^3$H-mibolerone (87.0 Ci/mmol) was added, so that a final concentration is adjusted to 1 nM, and at the same time, in order to inhibit binding of $^3$H-mibolerone to progestin receptor, triamsinolone acetonide was added to a final concentration of 5 μM, and the final volume was adjusted to 0.4 ml with buffer solution A, and the reaction mixture was incubated for 20 hours at 0° C. After incubation, 0.5 ml of 60% hydroxylapatite slurry (washed and equilibrate with a buffer solution B: 10 mM NaH$_2$P$_{04}$, 20 mM tris-hydrochloric acid, pH 7.2) was added, and incubated for 10 minutes at 0° C., the solution was transferred onto a glass fiber filter, and washed five times with 5 ml portions of buffer solution B containing 0.1% (weight/volume) of Triton X-100, to remove free $^3$H-mibolerone. This glass fiber was transferred into vial, and 10 ml of aquasol-2 was added, and the radioactivity was measured, and the total binding amount of $^3$H-mibolerone on prostate cytoplasm androgen receptor was determined.

The nonspecific binding amount was determined similarly by adding an unlabeled 5α-DHT in the reaction solution to a final concentration of 1 μM. The difference between the total binding amount and nonspecific binding amount was determined as the specific binding amount on the androgen receptor.

(3) Inhibitory activity of sample compounds on $^3$H-mibolerone specific binding The compounds obtained in the experiments were added simultaneously with $^3$H-mibolerone at different concentrations to incubate same as in (2), and the specific binding amount of 3H-mibolerone on androgen receptor was determined. Comparing this value with the value obtained in (2), the IC$_{50}$ value of inhibitory activity of the compounds on $^3$H-mibolerone specific binding was determined. The results are shown in Table 3.

Comparison 1: Flutamide
Comparison 2: Hydroxyflutamide

TABLE 3

| Test compound (Example No.) | Inhibitory activity on mibolerone specific binding [$IC_{50}(M)$] |
|---|---|
| 1 | $2.0 \times 10^{-7}$ |
| 3 | $9.0 \times 10^{-8}$ |
| 5 | $5.0 \times 10^{-7}$ |
| 6 | $9.0 \times 10^{-7}$ |
| 7 | $1.3 \times 10^{-5}$ |
| 8 | $1.7 \times 10^{-6}$ |
| 9 | $3.1 \times 10^{-5}$ |
| 10 | $>5.0 \times 10^{-6}$ |
| 11 | $4.2 \times 10^{-7}$ |
| 12 | $>5.0 \times 10^{-6}$ |
| 13 | $2.0 \times 10^{-6}$ |
| 14 | $2.0 \times 10^{-7}$ |
| 15 | $1.5 \times 10^{-7}$ |
| 18 | $1.2 \times 10^{-6}$ |
| 19 | $>5.0 \times 10^{-6}$ |
| 21 | $1.65 \times 10^{-7}$ |
| 22 | $5.2 \times 10^{-8}$ |
| 23 | $5.8 \times 10^{-8}$ |
| 24 | $6.4 \times 10^{-8}$ |
| 25 | $1.6 \times 10^{-7}$ |
| 26 | $1.8 \times 10^{-7}$ |
| 27 | $1.3 \times 10^{-7}$ |
| 28 | $>5.0 \times 10^{-6}$ |
| 29 | $2.5 \times 10^{-8}$ |
| 30 | $3.2 \times 10^{-7}$ |
| 33 | $2.8 \times 10^{-7}$ |
| 34 | $2.9 \times 10^{-7}$ |
| 35 | $8.8 \times 10^{-8}$ |
| 36 | $1.3 \times 10^{-7}$ |
| 37 | $5.8 \times 10^{-7}$ |
| 38 | $5.8 \times 10^{-8}$ |
| 39 | $1.3 \times 10^{-7}$ |
| 40 | $2.2 \times 10^{-8}$ |
| 42 | $3.0 \times 10^{-6}$ |
| 43 | $7.6 \times 10^{-8}$ |
| 44 | $7.7 \times 10^{-8}$ |
| 45 | $4.0 \times 10^{-7}$ |
| 46 | $1.7 \times 10^{-7}$ |
| 47 | $5.0 \times 10^{-8}$ |
| 49 | $>5.0 \times 10^{-6}$ |
| 50 | $6.4 \times 10^{-8}$ |
| 51 | $3.4 \times 10^{-7}$ |
| 52 | $2.3 \times 10^{-7}$ |
| 53 | $3.0 \times 10^{-7}$ |
| 54 | $7.6 \times 10^{-7}$ |
| 55 | $6.6 \times 10^{-8}$ |
| 56 | $1.2 \times 10^{-7}$ |
| 57 | $1.45 \times 10^{-7}$ |
| 58 | $>5 \times 10^{-6}$ |
| 59 | $1.65 \times 10^{-7}$ |
| 60 | $3.9 \times 10^{-8}$ |
| 61 | $1.6 \times 10^{-7}$ |
| 62 | $1.2 \times 10^{-7}$ |
| 63 | $>5 \times 10^{-6}$ |
| 64 | $7.4 \times 10^{-7}$ |
| 65 | $1.4 \times 10^{-7}$ |
| 66 | $1.6 \times 10^{-7}$ |
| 67 | $3.4 \times 10^{-8}$ |
| 68 | $1.3 \times 10^{-6}$ |
| 69 | $8.8 \times 10^{-8}$ |
| 70 | $1.55 \times 10^{-7}$ |
| 71 | $4.6 \times 10^{-7}$ |
| 72 | $1.6 \times 10^{-7}$ |
| 73 | $>5.0 \times 10^{-6}$ |
| 76 | $2.3 \times 10^{-8}$ |
| 77 | $4.6 \times 10^{-7}$ |
| 87 | $4.0 \times 10^{-8}$ |
| 101 | $1.5 \times 10^{-7}$ |
| Comparison 1 | $>>>5 \times 10^{-6}$ |
| Comparison 2 | $2.0 \times 10^{-6}$ |

What is claimed is:

1. A pyrimidine derivative expressed in Formula [I]:

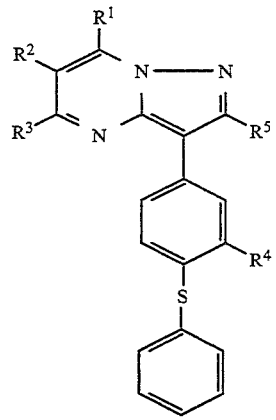

where $R^1$ denotes a hydrogen atom or hydroxyl group, $R^2$ denotes a hydrogen atom, lower alkoxycarbonyl group, lower alkoxy group, halogen atom, lower alkyl group, cycloalkyl group with 3 to 8 carbon atoms, lower alkoxycarbonyl lower alkyl group, carboxyl group, carboxy lower alkyl group, group: —CONHR$^6$ (R$^6$ represents a hydrogen atom, phenyl group which may possess halogen atom, or lower alkyl group), cyano group, phenyl group which may possess a group selected from the group consisting of hydroxyl group, halogen atom, lower alkyl group, lower alkoxy group and phenylthio group as a substituent, phenyl lower alkyl group which may possess a group selected from the group consisting of hydroxyl group and lower alkoxy group as a substituent on a phenyl ring, lower alkanoyloxy lower alkyl group, benzoyl group, lower alkanoyl group which may possess a halogen atom, or hydroxy lower alkyl group which may possess a group selected from the group consisting of phenyl group and halogen atom as a substituent, R$^3$ denotes a hydrogen atom, hydroxyl group, lower alkyl group, cycloalkyl group with 3 to 8 carbon atoms, halogen lower alkyl group, or phenyl group, R$^4$ denotes a hydrogen atom, lower alkyl group, or lower alkoxy group, and R$^5$ denotes a hydrogen atom, lower alkyl group, lower alkoxy lower alkyl group, or halogen lower alkyl group; provided that R$^2$ and R$^3$ may be bonded to each other to form a lower alkylene group with 3 to 5 carbon atoms, or its pharmaceutically available salt.

2. A pyrimidine derivative or its pharmaceutically available salt of claim 1, wherein, in Formula [I], R$^1$ denotes a hydrogen atom or hydroxyl group, R$^2$ denotes a hydrogen atom, $C_1$–$C_6$ alkoxycarbonyl group, $C_1$–$C_6$ alkoxy group, halogen atom, $C_1$–$C_6$ alkyl group, $C_3$–$C_8$ cycloalkyl group, $C_1$–$C_6$ alkoxycarbonyl $C_1$–$C_6$ alkyl group, carboxyl group, carboxy $C_1$–$C_6$ alkyl group, group: —CONHR$^6$ (R$^6$ represents a hydrogen atom, a phenyl group which may possess halogen atom, or $C_1$–$C_6$-alkyl group), cyano group, phenyl group which may possess 1 to 3 groups selected from the group consisting of hydroxyl group, halogen atom, $C_1$–$C_6$ alkyl group, $C_1$–$C_6$ alkoxy group and phenylthio group as substituent, phenyl $C_1$–$C_6$ alkyl group which may possess 1 to 3 groups selected from the group consisting of hydroxyl group and $C_1$–$C_6$ alkoxy group as substituent on phenyl ring, $C_2$–$C_6$ alkanoyloxy $C_1$–$C_6$ alkyl group, benzoyl group, $C_2$–$C_6$ alkanoyl group which may possess 1 to 3 halogen atoms, or hydroxy $C_1$–$C_6$ alkyl group which may possess 1 to 3 groups selected from the group consisting of phenyl group and halogen group as substituent, $R^3$ denotes a hydrogen atom, hydroxyl group, $C_1$–$C_6$ alkyl group, $C_3$–$C_8$ cycloalkyl group, halogen $C_1$–$C_6$ alkyl group, or phenyl group, $R^4$ denotes a hydrogen atom, $C_1$–$C_6$ alkyl group, or $C_1$–$C_6$ alkoxy group, and $R^5$ denotes a hydrogen atom, $C_1$–$C_6$ alkyl group, $C_1$–$C_6$ alkoxy $C_1$–$C_6$ alkyl group, or halogen $C_1$–$C_6$ alkyl group; provided that $R^2$ and $R^3$ may be bonded to each other to form a $C_3$–$C_5$ alkylene group.

3. A pyrimidine derivative or its pharmaceutically available salt of claim 2, wherein $R^1$ is a hydroxyl group.

4. A pyrimidine derivative or its pharmaceutically available salt of claim 2, wherein $R^1$ is a hydrogen atom.

5. A pyrimidine derivative or its pharmaceutically available salt of claim 3, wherein $R^5$ is a hydrogen atom.

6. A pyrimidine derivative or its pharmaceutically available salt of claim 3, wherein $R^5$ is $C_1$–$C_6$ alkyl group, $C_1$–$C_6$ alkoxy $C_1$–$C_6$ alkyl group or halogen $C_1$–$C_6$ alkyl group.

7. A pyrimidine derivative or its pharmaceutically available salt of claim 5, wherein $R^3$ is a hydrogen atom.

8. A pyrimidine derivative or its pharmaceutically available salt of claim 5, wherein $R^2$ and $R^3$ are bonded to form $C_3$–$C_5$ alkylene group.

9. A pyrimidine derivative or its pharmaceutically available salt of claim 5, wherein $R^3$ is hydroxyl group, $C_1$–$C_6$ alkyl group, $C_3$–$C_8$ cycloalkyl group, halogen $C_1$–$C_6$ alkyl group or phenyl group.

10. A pyrimidine derivative or its pharmaceutically available salt of claim 7 wherein $R^4$ is a hydrogen atom.

11. A pyrimidine derivative or its pharmaceutically available salt of claim 7, wherein $R^4$ is $C_1$–$C_6$ alkyl group or $C_1$–$C_6$ alkoxy group.

12. A pyrimidine derivative or its pharmaceutically available salt of claim 10, wherein $R^2$ is hydrogen atom, halogen atom, $C_1$–$C_6$ alkyl group, or $C_1$–$C_6$ alkoxy group.

13. A pyrimidine derivative or its pharmaceutically acceptable salt of claim 10, wherein $R^2$ is phenyl group which may possess 1 to 3 groups selected from the group consisting of hydroxyl group, halogen atom, $C_1$–$C_6$ alkyl group, $C_1$–$C_6$ alkoxy group and phenylthio group as substituent, phenyl $C_1$–$C_6$ alkyl group which may possess 1 to 3 groups selected from the group consisting of hydroxyl group and $C_1$–$C_6$ alkoxy group as substituent on phenyl ring, $C_2$–$C_6$ alkanoyl group which may possess 1 to 3 halogen atoms, or hydroxy $C_1$–$C_6$ alkyl group which may possess 1 to 3 groups selected from the group consisting of phenol group and halogen group as substituent.

14. A pyrimidine derivative or its pharmaceutically available salt of claim 10, wherein $R^2$ is $C_1$–$C_6$ alkoxycarbonyl group, $C_3$–$C_8$ cycloalkyl group, $C_1$–$C_6$ alkoxycarbonyl $C_1$–$C_6$ alkyl group, carboxyl group, carboxy $C_1$–$C_6$ alkyl group, group: —CONHR$^6$ (R$^6$ represents hydrogen atom, phenyl group which may possess halogen atom, or $C_1$–$C_6$ alkyl group), cyano group, $C_2$–$C_6$ alkanoyloxy $C_1$–$C_6$ alkyl group, or benzoyl group.

15. A pyrimidine derivative or its pharmaceutically available salt of claim 13, wherein $R^2$ is phenyl group, benzyl group, $C_2$–$C_6$ alkanoyl group, or hydroxy $C_1$–$C_6$ alkyl group.

16. A pyrimidine derivative being 7-hydroxy-3-(4-phenylthiophenyl) pyrazolo[1,5-a]pyrimidine, 7-hydroxy-3-(3-methoxy-4-phenylthiophenyl) pyrazolo[1,5-a]pyrimidine, 7-hydroxy-6-methoxy-3-(4-phenylthiophenyl) pyrazolo[1,5-a]pyrimidine, 7-hydroxy-6-fluoro-3-(4-phenylthiophenyl)pyrazolo[1,5-a]pyrimidine, 7-hydroxy-6-phenyl -3-(4-phenylthiophenyl)-pyrazolo[1,5-a]pyrimidine, 7-hydroxy-6-methyl-3-(4-phenylthiophenyl)pyrazolo [1,5-a]pyrimidine, 7-hydroxy-6-benzyl-3-(4-phenylthiophenyl) pyrazolo[1,5-a]pyrimidine, 7-hydroxy-6-bromo-3-(4-phenylthiophenyl)pyrazolo[1,5-a]pyrimidine, 7-hydroxy-6-chloro-3-(4-phenylthiophenyl)pyrazolo[1,5-α]pyrimidine, 7-hydroxy-6-acetyl-3-(4-phenylthiophenyl)pyrazolo[1,5-a]pyrimidine, 7-hydroxy-6-(1-hydroxyethyl)-3-(4-phenylthiophenyl)pyrazolo[1,5-a]pyrimidine, or 7-hydroxy-6-(α-hydroxybenzyl)-3-(4-phenylthiophenyl)-pyrazolo[1,5-a]pyrimidine, 7-hydroxy-3-(3-methyl-4-phenylthiomethyl)pyrazolo[1,5-a]pyrimidine or 7-hydroxy-6-fluoro-3-(4-phenylthiophenyl) pyrazolo[1,5-a]pyrimidine, or its pharmaceutically available salt.

17. A therapeutic method for inhibiting androgens comprising internal administration or external application of a pharmaceutical preparation comprising (1) a compound represented by formula (II):

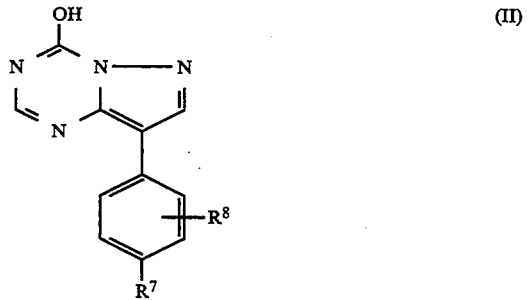

wherein $R^7$ is selected from the group consisting of:
(a) a phenylthio group, wherein the phenyl of said group may have 1 to 3 substituents selected from the group consisting of a halogen atom, a lower alkyl group, and a lower alkoxy group;
(b) a phenyl lower alkylthio group, wherein the phenyl of said group may have 1 to 3 substituents selected from the group consisting of a halogen atom, a lower alkyl group, and a lower alkoxy group; and
(c) a group represented by the formula —SO$_2$NHR$^9$, wherein R$^9$ represents a cycloalkyl group, a pyridyl group, or a phenyl group, wherein the phenyl of said group may have 1 to 3 substituents selected from the group consisting of a halogen atom, a cyano group, and a lower alkyl group;

and R$^8$ is selected from the group consisting of a hydrogen atom, a lower alkoxy group, a lower alkyl group, and a halogen atom, and (2) a pharmaceutically acceptable carrier.

18. A pharmaceutical composition to be used as an androgen inhibitor comprising a therapeutically effective amount of a pyrimidine derivative expressed in Formula [I] of claim 1 or its pharmaceutically available salt, and a pharmaceutically available carrier.

* * * * *